(12) United States Patent
ElShamy

(10) Patent No.: US 9,075,071 B1
(45) Date of Patent: Jul. 7, 2015

(54) METHODS FOR DIAGNOSIS AND TREATMENT OF CANCER

(71) Applicant: University of Mississippi Medical Center, Jackson, MS (US)

(72) Inventor: Wael M. ElShamy, Madison, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 13/717,304

(22) Filed: Dec. 17, 2012

(51) Int. Cl.
*C07K 16/18* (2006.01)
*G01N 33/68* (2006.01)

(52) U.S. Cl.
CPC .................................. *G01N 33/6893* (2013.01)

(58) Field of Classification Search
None
See application file for complete search history.

(56) References Cited

U.S. PATENT DOCUMENTS 7,811,778 B2 * 10/2010 Goldenring ................... 435/7.23

OTHER PUBLICATIONS

Nishihara et al. (Oncology Reports, 21: 1189-1195, 2009).*
Barilá et al. (EMBO, 19(2): 273-281, 2000).*
Storchova Z, Pellman D. From polyploidy to aneuploidy, genome instability and cancer. Nat Rev Mol Cell Biol. 2004; 5: 45-54.
Eggert U, Mitchison T, Field C. Animal cytokinesis: from parts list to mechanisms. Ann Rev Biochem. 2006; 75: 543-566.
Wohlschlegel J, Dwyer B, Dhar S, Cvetic C, Walter J, Dutta A. Inhibition of eukaryotic DNA replication by geminin binding to Cdt1. Science. 2000; 290: 2309-2312.
McGarry T, Kirschner M. Geminin, an inhibitor of DNA replication, is degraded during mitosis. Cell. 1998; 93(6): 1043-5321.
Del Bene F, Tessmar-Raible K, Wittbrodt J. Direct interaction of geminin and Six3 in eye development. Nature. 2004; 427(6976): 745-749.
Luo L, Yang X, Takihara Y, Knoetgen H, Kessel M. The cell-cycle regulator geminin inhibits Hox function through direct and Polycomb mediated interactions. Nature. 2004; 427(6976): 749-753.
Seo S, Herr A, Lim J, Richardson G, Richardson H, Kroll K. Geminin regulates neuronal differentiation by antagonizing Brg1 activity. Genes Dev. 2005; 19(14): 1723-1734.
McGarry T. Geminin deficiency causes a Chk1-dependent G2 arrest in Xenopus. Mol Biol Cell. 2002; 13(10): 3662-3671.
Nakuci E, Xu M, Pujana M, Valls J, ElShamy WM. Geminin is bound to chromatin in G2/M phase to promote proper cytokinesis. Int J Biochem Cell Biol. 2006; 38(7): 1207-1220.
Gardner L, Malik R, Shimizu Y, ElShamy, WM. Geminin overexpression prevents the completion of topoisomerase IIα chromosome decatenation leading to aneuploidy in human mammary epithelial cells. Breast Cancer Res. 2011; 13(53).
Montanari M, Boninsegna A, Faraglia B, Coco C, Giordano A, Cittadini A, Sgambato A. Increased expression of geminin stimulates the growth of mammary epithelial cells and is a frequent event in human tumors. J Cell Physiol. 2005; 202(1): 215-22.
Gonzalez M, Tachibana K, Chin S, Callagy G, Madine M, Vowler S, Pinder S, Laskey R, Coleman N. Geminin predicts adverse clinical outcome in breast cancer by reflecting cell-cycle progression. J Pathol. 2004; 204(2): 121-130.
Wohlschlegel J, Kutok J, Weng A, Dutta A. Expression of geminin as a marker of cell proliferation in normal tissues and malignancies. Am J Pathol. 2002; 161(1): 267-273.
Aoyama K, Fukumoto Y, Ishibashi K, Kubota S, Morinaga T, Horiike Y et al. (2011). Nuclear c¬-Abl-mediated tyrosine phosphorylation induces chromatin structural changes through histone modifications that include H4K16 hypoacetylation. Exp Cell Res 317: 2874-2903.
Baskaran R, Wood L, Whitaker L, Canman C, Morgan S, Xu Yet al. (1997). Ataxia telangiectasia mutant protein activates c-Abl tyrosine kinase in response to ionizing radiation. Nature 387: 516-519.
Blanchard Z, Malik R, Mullins N, Maric C, Luk H, Norio D et al. (2011). Geminin overexpression induces mammary tumors via suppressing cytokinesis. Oncotarget 2(12): 1011-1027.
Colicelli J. (2010). ABL tyrosine kinases: evolution of function, regulation, and specificity. Sci Signal 3(139): re6.
DeMatteo RP. Nanoneoadjuvant therapy of gastrointestinal stromal tumor (GIST). (2009). Ann Surg Oncol 16: 799-800.
Druker BJ, Talpaz M, Resta DJ, Peng B, Buchdunger E, Ford J et al. (2001). Efficacy and safety of a specific inhibitor of the BCR-ABL tyrosine kinase in chronic myeloid leukemia. N Engl J Med 344: 1031-1037.
Ganguly S, Fiore L, Sims L, Friend J, Srinivasan D, Thacker M et al. (2012). c-Abl and Arg are activated in human primary melanomas, promote melanoma cell invasion via distinct pathways, and drive metastatic progression. Oncogene 31(14): 1804-1816.
Kroll K, Salic A, Evans L, Kirschner M. (1998). Geminin, a neutralizing molecule that demarcates the future neural plate at the onset of gastrulation. Development 125: 3247-3258.
Lin J, Arlinghaus R. (2008). Activated c-Abl tyrosine kinase in malignant solid tumors. Oncogene 27: 4385-4391.
Mancini M, Veljkovic N, Corradi V, Zuffa E, Corrado P. et al. (2009). 14-3-3 ligand prevents nuclear import of c-ABL protein in chronic myeloid leukemia. Traffic 10(6): 637-647.
Nakuci E, Xu M, Pujana M, Valls J, ElShamy WM. (2006). Geminin is bound to chromatin in G2/M phase to promote proper cytokinesis. Int J Biochem Cell Biol 38(7): 1207-1220.

(Continued)

*Primary Examiner* — Brad Duffy
*Assistant Examiner* — Nelson B Moseley, II
(74) *Attorney, Agent, or Firm* — Stites & Harbison PLLC; Terry L. Wright

(57) ABSTRACT

Methods for diagnosis and treatment of a cancer treatable with a c-Abl inhibitor are provided. Methods for diagnosing a cancer treatable with a c-Abl inhibitor include providing a biological sample from subject, determining an amount in the sample of geminin, c-Abl, or both, and comparing the amount of geminin, c-Abl, or both, if present, to a control level to thereby diagnose a subject as having a cancer treatable with a c-Abl inhibitor if there is a measurable difference in the amount of geminin, c-Abl, or both in the sample as compared to the control level. Methods for treating a cancer include identifying a subject as having a cancer treatable with a c-Abl inhibitor by determining an amount of geminin, c-Abl, or both, and then administering an effective amount of a c-Abl inhibitor to the subject. Screening methods for identifying compounds useful for inhibiting c-Abl are also provided.

20 Claims, 36 Drawing Sheets

(56) References Cited

OTHER PUBLICATIONS

Plattner R, Kadlec L, DeMali K, Kazlauskas A, Pendergast A. (1999). c-Abl is activated by growth factors and Src family kinases and has a role in the cellular response to PDGF. Genes Dev 13: 2400-2411.

Shaul Y, Ben-Yehoyada M. (2005). Role of c-Abl in the DNA damage stress response. Cell Res 15: 33-35.

Sirvent A, Benistant C, Roche S. (2008). Cytoplasmic signaling by the c-Abl tyrosine kinase in normal and cancer cells. Biol Cell 100: 617-631.

Srinivasan D, Plattner P. (2006). Activation of Abl tyrosine kinases promotes invasion of aggressive breast cancer cells. Cancer Res 66: 5648-5655.

Srinivasan D, Kaetzel DM, Plattner R. (2009). Reciprocal regulation of Abl and receptor tyrosine kinases. Cell Signal 21: 1143-1150.

Taagepera S, McDonald D, Loeb J, Whitaker L, McElroy A, Wang J et al. (1998). Nuclear-cytoplasmic shuttling of c-Abl tyrosine kinase. Proc Natl Acad Sci USA 95: 7457-7462.

Thépaut M, Maiorano D, Guichou JF, Augé MT, Dumas C, Méchali M et al. (2004). Crystal structure of the coiled-coil dimerization motif of geminin: structural and functional insights on DNA replication regulation. J Mol Biol 342(1): 275-287.

* cited by examiner

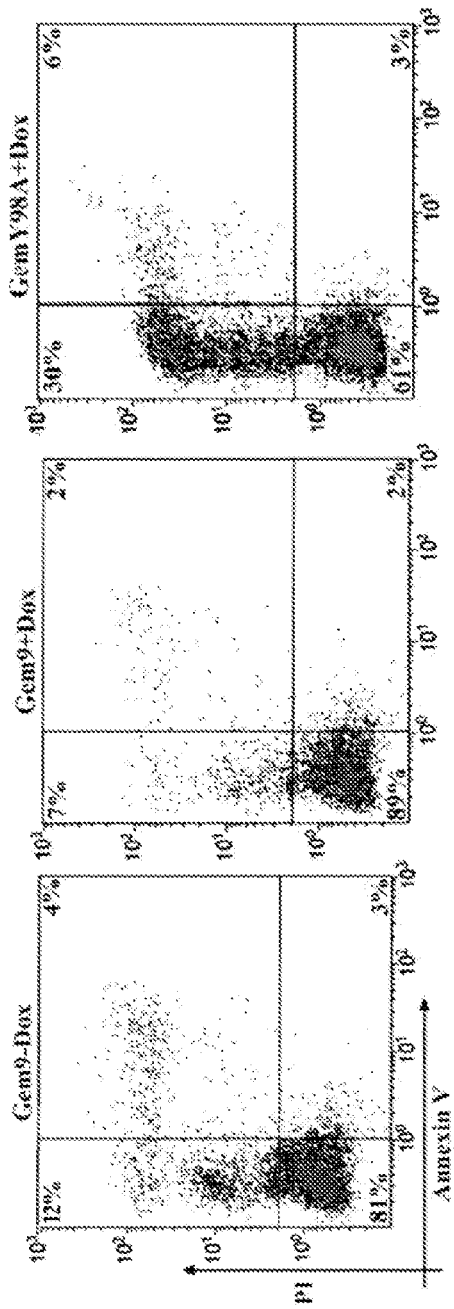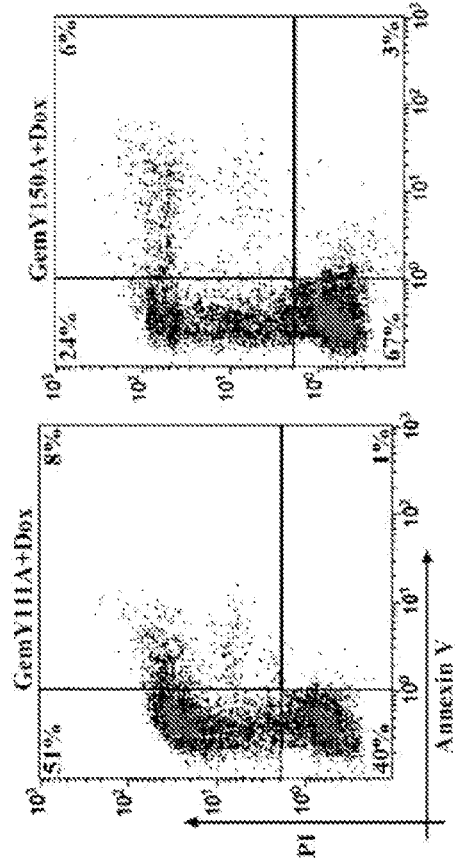

METHODS FOR DIAGNOSIS AND TREATMENT OF CANCER

TECHNICAL FIELD

The presently-disclosed subject matter relates to methods for the diagnosis and treatment of cancer. In particular, the presently-disclosed subject matter relates to methods for the diagnosis and treatment of cancers treatable with a c-Abl inhibitor that are based on a determination of an amount of geminin, c-Abl, or both in a biological sample obtained from a subject.

BACKGROUND

Cancer continues to be a leading cause of death with over 1.6 million new cases of cancer being diagnosed in 2012 and over 500,000 people dying from cancer in the United States alone in 2012. For example, in the United States, breast cancer affects over 250,000 women every year, and represents the most common form of cancer in females. Indeed, it has been found that 1 out of every 8 women in the United States will develop invasive breast cancer during their lifetime and that almost 40,000 women die of breast cancer each year.

Despite efforts to improve treatment and detection of cancer, cancer survival has still not improved significantly over the past two decades for a number of cancer types due, at least in part, to the numerous subtypes of certain cancers and due to the various mechanisms responsible for the development of those cancer subtypes. In this regard, future therapies for cancer will likely be based on a combination of diagnostic and prognostic indicators or biomarkers. The identification of such biomarkers suitable for early diagnosis and detection of cancer holds great promise in not only allowing for a more comprehensive screening of populations, but also in selecting an appropriate treatment that is directed specifically toward a particular cancer subtype or its respective mechanism of action.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter a method for diagnosing a cancer treatable with a c-Abl inhibitor in a subject is provided, which comprises providing a biological sample from the subject; determining an amount in the sample of geminin, c-Abl, or both; and comparing the amount of geminin, c-Abl, or both in the sample, if present, to a control level of geminin, c-Abl, or both, wherein the subject is diagnosed as having a cancer treatable with a c-Abl inhibitor, or a risk thereof, if there is a measurable difference in the amount of geminin, c-Abl, or both in the sample as compared to the control level. In some embodiments, determining an amount of geminin, c-Abl, or both in the sample comprises detecting the expression of geminin, c-Abl, or both in a cell of a subject. In some embodiments, determining an amount in the sample of geminin, c-Abl, or both comprises determining an amount of both geminin and c-Abl, such as, in some embodiments, nuclear c-Abl.

In some embodiments of the method, the cancer can be selected from breast cancer, liver cancer, ovarian cancer, colon cancer, brain cancer, lung cancer, and prostate cancer. In some embodiments, the cancer is breast cancer, such as human epidermal growth factor receptor 2-positive (HER2$^+$) breast cancer or triple negative breast cancer. In some embodiments, the subject has a cancer treatable with a c-Abl inhibitor. In some embodiments, the subject is human.

The biological sample that is provided can be, for example, a tissue biopsy that includes one or more cancer cells or cells that are suspected of being cancerous. In some embodiments the amount of geminin, c-Abl, or both in the biological sample is determined using an immunoassay analysis. In some embodiments, the methods further include the step of providing a probe for selectively binding and for determining an amount of the geminin, c-Abl, or both in a particular sample. In some embodiments, an apparatus is further provided that is capable of affecting detection of geminin, c-Abl, or both.

In some embodiments of the presently-disclosed subject matter, a method for determining whether to initiate or continue prophylaxis or treatment of a cancer treatable with a c-Abl inhibitor in a subject is provided, which comprises providing a series of biological samples over a time period from the subject; analyzing the series of biological samples to determine an amount in each of the biological samples of geminin, c-Abl, or both; and comparing any measurable change in the amounts of geminin, c-Abl, or both in each of the biological samples to thereby determine whether to initiate or continue the prophylaxis or therapy of the cancer. In some embodiments, the series of biological samples comprises a first biological sample collected prior to initiation of the prophylaxis or treatment for the cancer that is treatable is a c-Abl inhibitor and a second biological sample collected after initiation of the prophylaxis or treatment. In some embodiments, the series of biological samples comprises a first biological sample collected prior to onset of the cancer treatable with a c-Abl inhibitor and a second biological sample collected after the onset of the cancer.

Further provided, in some embodiments of the presently-disclosed subject matter, are methods for treating a cancer. In some embodiments, a method for treating a cancer is provided that comprises: identifying a subject as having a cancer treatable with a c-Abl inhibitor if there is a measurable difference in the amount of geminin, c-Abl, or both in a biological sample obtained from the subject; and then administering an effective amount of a c-Abl inhibitor to the subject. In some embodiments, administering an effective amount of the c-Abl inhibitor comprises orally administering the c-Abl inhibitor. In some embodiments, the c-Abl inhibitor is imatinib or nilotinib.

Still further provided by the presently-disclosed subject matter are methods for identifying compounds that inhibit c-Abl. In some embodiments, a method for identifying a compound that inhibits c-Abl is provided that comprises the steps of providing a cell that expresses geminin, contacting the cell with a test compound, and then determining whether phosphorylation of geminin is decreased in the presence of the test compound, such that a decrease in phosphorylation of geminin identifies the compound as useful for inhibiting c-Abl. In some embodiments, determining whether phosphorylation of geminin is decreased comprises determining whether phosphorylation of geminin is decreased at tyrosine 150. In some embodiments of the screening methods, the screening methods further comprise the step of determining an amount of geminin in the cell subsequent to contacting the cell with a test compound, such that a decrease in the amount of geminin in the cell as compared to a control level identifies the compound as useful for inhibiting c-Abl.

In still further embodiments of the screening methods of the presently-disclosed subject matter, the step of providing a cell expressing geminin comprises providing a cell that overexpresses geminin. In such embodiments, the screening methods can further comprise the step of determining a number of chromosomes in the geminin-overexpressing cell such that a reduction in aneuploidy in the geminin-overexpressing cell can then be used to identify a test compound as one that is useful for inhibiting c-Abl. In other embodiments that make use of geminin-overexpressing cells, the screening methods further comprise the step of determining an amount of apoptosis in the cell that overexpresses geminin subsequent to contacting the cell with the test compound, such that an increase in apoptosis can be used to identify a compound as one that is useful for inhibiting c-Abl.

Further advantages of the presently-disclosed subject matter will become evident to those of ordinary skill in the art after a study of the description, Figures, and non-limiting Examples in this document.

BRIEF DESCRIPTION OF THE DRAWINGS

FIGS. 8A-8E are graphs showing the results of FACS experiments used to analyze the extent to which a tyrosine mutation converts geminin into a cell death inducer protein when overexpressed, where HME and induced (48 h) Gem9, GemY98A, GemY111A and GemY150A cells were used, where the cells were harvested and after FITC-annexin-V binding and PI staining were analyzed by FACS, and where the lower left quadrants show viable cells (V$^-$/PI$^-$), the lower right quadrants show early apoptotic cells (V$^+$/PI$^-$), the upper left quadrants show necrotic cells (V$^-$/PI$^+$), and the upper right quadrants show non-viable late apoptotic/necrotic cells (V$^+$/PI$^+$);

(FIG. 12B); a schematic representation of the role of geminin in normal versus abnormal cell division (FIG. 12C); a graph showing the results of an experiment where HME or Gem9 cells were either transfected with control or si-c-Abl (for 72 hr) or treated with 10 µM of imatinib (during the last 24 h) in the presence or absence of doxycycline (72 h), and where cells from all cultures were collected labeled with a FITC-conjugated anti-p-(S10)-H3 antibody and analyzed by FACS (FIG. 12D); images of Gem9 cells that were treated or not with 10 µM of imatinib (during the last 24 h) in the presence or absence of doxycycline (72 h) (FIG. 12E); and graphs showing the results of a FACS analysis of Gem9 cells that were treated or not with 10 µM of imatinib (during the last 24 h) in the presence or absence of doxycycline (72 h) (FIG. 12F);

DESCRIPTION OF EXEMPLARY EMBODIMENTS

Figure 1A:
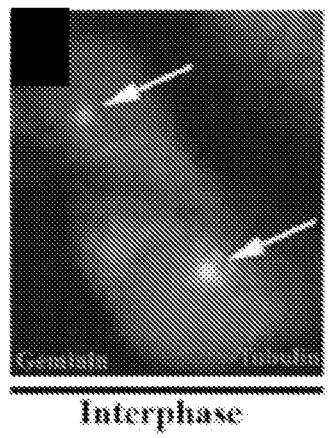
FIGS. 1A-1F are images showing geminin localization and expression in human mammary epithelial (HME) cells, including images showing the localization of geminin and γ-tubulin in interphase (FIG. 1A), metaphase (FIG. 1B) and in cytokinesis (FIG. 1C) in HME cells; an image of a western blot showing expression of Myc-tagged WT or Y-to-A geminin variants in HME cells (FIG. 1D); an image of a western blot showing the expression of His-tagged WT (Gem9) or Y-to-A mutant geminin variants in nuclear soluble or chromatin HME cells fractions (FIG. 1E); and images showing the localization of endogenous geminin and Myc-tagged exogenous geminin variants in HME cells (FIG. 1F)

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry) is intended to encompass the fragment as well as the full-length peptide. As such, determining an amount of a biomarker in a sample can include determining an amount of the full-length biomarker polypeptide, modified variants, and/or fragments thereof.

Initiation of DNA replication in S phase starts by the sequential binding of the component of the pre-replication complex (pre-RC), origin recognition complex (ORC), Cdc6 and Cdt1. However, binding of the mini-chromosomal maintenance proteins (MCM2-7) to Cdt1 at the origin of replication (ORI) is the rate-limiting step in DNA replication initiation. In association with that rate-limiting step, geminin (see, e.g., GENBANK® Nos. NP 056979 and NM 015895) is a coiled-coil protein, without sequence homology to any known protein, that inhibits re-initiation of replication in a single cell cycle by binding to Cdt1 at ORIs and preventing MCM complex binding to maintain chromosomal integrity. Additionally, recent work has also identified other critical roles for geminin in the regulation of several developmental processes. For instance, in *Drosophila*, geminin regulates neural cell fate determination and in the mouse, geminin regulates cellular differentiation by binding to and antagonizing Six3 or Hox transcriptional activity.

In mediating its various cellular roles, geminin translocates from the nuclear soluble fraction to insoluble areas, such as to chromatin and centrosomes, at the end of S phase, which perhaps saves, at least some of cellular geminin from anaphase-promoting complex (APC)-dependent degradation. Additionally, in mediating its roles, geminin is serine/threonine phosphorylated in S phase, but tyrosine phosphorylated during $G_2$/M/early $G_1$ phase. Moreover, it has been found that geminin overexpression induces aneuploidy by prematurely inhibiting topoisomerase II alpha (TopoII$\alpha$) normal decatenation function, or prematurely inhibiting Aurora B activation and its mitotic functions. Indeed, geminin-overexpressing cells have been found to completely lack histone H3 (S10) phosphorylation and chromosome condensation events induced by Aurora B kinase. Finally, geminin carries 3 tyrosine residues, at positions 98, 111 and 150, and it has been found that overexpression of any single tyrosine mutant geminin restored histone H3-(S10) phosphorylation, chromosome condensation/segregation and triggered apoptosis instead of aneuploidy.

In connection with the actions of geminin, the proto-oncogene c-Abl (see, e.g., GENBANK® Nos. NP 009297 and NM 007313) is a tightly regulated, ubiquitously expressed multifunctional non-receptor protein tyrosine kinase. c-Abl contains a catalytic domain, SH2 and SH3 protein-protein interactions domains, a DNA binding domain, three nuclear localization signals, a nuclear export signal and F- and G-actin binding domains. c-Abl can be localized to the plasma membrane, cytoplasm and nucleus and affects a variety of cellular functions and activities. Cytoplasmic c-Abl plays important roles in cell proliferation, differentiation, and migration, whereas nuclear translocation of c-Abl activated by ATM upon DNA damage and oxidative stress is involved in induction of apoptosis and DNA damage repair. Recently, other important function for nuclear c-Abl, such as phosphorylation of heterochromatic histones, a modification involved in chromatin dynamics has also been identified.

The role of BCR-Abl (an oncogenic form of c-Abl) in chronic myelogenous leukemia (CML) is appreciated, but c-Abl is also activated in many solid tumors, such as glioblastoma, melanoma, non-small-cell lung cancer, breast and gastric carcinomas. In this regard, imatinib mesylate, which is also known as Gleevec® or STI571 (Novartis AG Corporation, Basel Switzerland) is a small molecule inhibitor that targets the ATP-binding site in the c-Abl kinase domain and has been successful in treating CML, but has efficacies in solid tumors expression mutant c-Kit, or overexpressing $\alpha$-, or $\beta$-platelet-derived growth factor receptors, such as gastrointestinal stroma tumors expressing. In this regard, it has now been observed that inhibiting geminin phosphorylation (such as inhibiting geminin Y150 phosphorylation) by inhibiting c-Abl expression or activity: destabilized endogenous as well as overexpressed geminin protein; caused a reduction in aneuploidy; and led to an increase in cell death that can be induced specifically in geminin overexpressing cells. More specifically, it has been observed that in certain cells c-Abl was nuclear in geminin overexpression-induced subcutaneous or orthotopic mammary tumors samples, and that c-Abl inhibitors, such as imatinib, were as effective as doxorubicin in killing geminin overexpression-induced tumors.

The presently-disclosed subject matter thus provides methods for the diagnosis and treatment of cancer and, in particular, methods for the diagnosis and treatment of cancers treatable with a c-Abl inhibitor that are based on a determination of an amount of geminin, c-Abl, or both in a biological sample obtained from a subject. In some embodiments, the presently-disclosed subject matter includes methods for diagnosing a cancer treatable with a c-Abl inhibitor in a subject in a subject, and for determining whether to initiate or continue prophylaxis or treatment of such a cancer in a subject, by identifying an amount of biomarker selected from geminin, c-Abl, or both in a biological sample from a subject.

The term "cancer," as used herein refers to all types of cancer or neoplasm or malignant tumors found in animals, including leukemias, carcinomas, melanoma, and sarcomas. Examples of cancers are cancer of the brain, bladder, breast, cervix, colon, head and neck, kidney, lung, non-small cell lung, mesothelioma, ovary, prostate, sarcoma, stomach, uterus and Medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer.

The phrase "cancer treatable with a c-Abl inhibitor" is used herein to refer cancers wherein inhibition or reduction in the activity of c-Abl is effective in "treating" the cancer as defined herein below. Such cancers include, but are not limited to leukemia (CML) as well as many solid tumors, such as glioblastoma, melanoma, non-small-cell lung cancer, breast, liver, and gastric carcinomas. In some embodiments, the cancer treatable with a c-Abl inhibitor is selected breast cancer, liver cancer, ovarian cancer, colon cancer, brain cancer, lung cancer, and prostate cancer. In some embodiments, the cancer is a breast cancer, such as, in some embodiments, a human epidermal growth factor receptor 2-positive (HER2+) breast cancer. In some embodiments, the cancer is a breast cancer such as a triple negative breast cancer or, in other words, a breast cancer that is estrogen receptor-negative (ER−), progesterone receptor-negative (PR−) and human epidermal growth factor receptor 2-negative (HER2−). In other embodiments, the cancer is a liver cancer, such as, in some embodiments, a hepatocellular carcinoma.

Turning now to the geminin and c-Abl biomarkers used in accordance with the presently-disclosed subject matter, in some embodiments, the geminin and c-Abl biomarkers are human geminin and c-Abl protein or mRNA biomarkers. However, these exemplary human biomarkers are not intended to limit the present subject matter to human polypeptide biomarkers or mRNA biomarkers only. Rather, the present subject matter encompasses biomarkers across animal species that are associated with cancers that are treatable with a c-Abl inhibitor. In addition, standard gene/protein nomenclature guidelines generally stipulate human gene name abbreviations are capitalized and italicized and protein name abbreviations are capitalized, but not italicized. Further, standard gene/protein nomenclature guidelines generally stipulate mouse, rat, and chicken gene name abbreviations italicized with the first letter only capitalized and protein name abbreviations capitalized, but not italicized. In contrast, the gene/protein nomenclature used herein when referencing specific biomarkers uses all capital letters for the biomarker abbreviation, but is intended to be inclusive of genes (including mRNAs and cDNAs) and proteins across animal species.

A "biomarker" is a molecule useful as an indicator of a biologic state in a subject. With reference to the present subject matter, the biomarkers disclosed herein can be polypeptides that exhibit a change in expression or state, which can be correlated with the risk of developing, the presence of, or the progression of a cancer treatable with a c-Abl inhibitor in a subject. In addition, the biomarkers disclosed herein are inclusive of messenger RNAs (mRNAs) encoding the biomarker polypeptides, as measurement of a change in expression of an mRNA can be correlated with changes in expression of the polypeptide encoded by the mRNA. As such, determining an amount of a biomarker in a biological sample is inclusive of determining an amount of a polypeptide biomarker and/or an amount of an mRNA encoding the polypeptide biomarker either by direct or indirect (e.g., by measure of a complementary DNA (cDNA) synthesized from the mRNA) measure of the mRNA.

In some embodiments of the presently-disclosed subject matter, a method for diagnosing a cancer treatable with a c-Abl inhibitor in a subject is provided. The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a marker, the amount (including presence or absence) of which is indicative of the presence, severity, or absence of the condition.

Along with diagnosis, clinical cancer prognosis is also an area of great concern and interest. It is important to know the aggressiveness of the cancer cells and the likelihood of tumor recurrence in order to plan the most effective therapy. If a more accurate prognosis can be made, appropriate therapy, and in some instances less severe therapy for the patient can be chosen. Measurement of biomarker levels disclosed herein (e.g., geminin, c-Abl, or both) can be useful in order to categorize subjects according to advancement of a cancer treatable with a c-Abl inhibitor who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic biomarker levels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to suffer from a cancer treatable with a c-Abl inhibitor than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments of the presently-disclosed subject matter, a threshold degree of change in the level of a prognostic or diagnostic biomarker can be established, and the degree of change in the level of the indicator in a biological sample can simply be compared to the threshold degree of change in the level. A preferred threshold change in the level for markers of the presently-disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently disclosed subject matter, multiple determinations of one or more diagnostic or prognostic peptide biomarkers can be made, and a temporal change in the biomarker can be used to monitor the progression of disease and/or efficacy of appropriate therapies directed against the disease. In such an embodiment, for example, one might expect to see a decrease or an increase in the biomarker(s) over time during the course of effective therapy. Thus, the presently-disclosed subject matter provides in some embodiments a method for determining treatment efficacy and/or progression of a cancer treatable with a c-Abl inhibitor in a subject. In some embodiments, the method comprises determining an amount of at least one peptide biomarker associated with a cancer treatable with a c-Abl inhibitor, such as for example geminin, c-Abl, or both in biological samples collected from the subject at a plurality of different time points and comparing the amounts of geminin, c-Abl, or both in the samples collected at different time points. For example, a first time point can be selected prior to initiation of a treatment and a second time point can be selected at some time after initiation of the treatment. One or more biomarker levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from, or known to be at risk of, a given condition (e.g., a cancer treatable with a c-Abl inhibitor); or in subjects known to be free of a given condition, i.e. "normal individuals". For example, a biomarker level in a biological sample can be compared to a level known to be associated with a specific type of cancer that is treatable with a c-Abl inhibitor. The sample's biomarker level is said to have been correlated with a diagnosis; that is, the skilled artisan can use the biomarker level to determine whether the subject suffers from a specific type of cancer, and respond accordingly. Alternatively, the sample's biomarker level can be compared to a control marker level known to be associated with a good outcome (e.g., the absence of cancer), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determination of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type of cancer, or a given prognosis. Likewise, a decrease in the marker from the initial time to the second time can be indicative of a particular type of cancer, or a given prognosis. Furthermore, the degree of change of one or more markers can be related to the severity of cancer and future adverse events.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

In some embodiments, a method for diagnosing a cancer treatable with a c-Abl inhibitor in a subject is provided that comprises providing a biological sample from the subject; determining an amount of geminin, c-Abl, or both; and identifying the subject as having a cancer treatable with a c-Abl inhibitor, or a risk thereof, if there is a measurable difference in the amount of geminin, c-Abl, or both in the sample as compared to a control level. In some embodiments, determining an amount in the sample of geminin, c-Abl, or both comprises detecting the expression of geminin, c-Abl, or both in a cell of a subject. In some embodiments, determining an amount in the sample of geminin, c-Abl, or both comprises determining an amount of both geminin and c-Abl. In some embodiments, the c-Abl is nuclear c-Abl or, in other words, c-Abl that is localized to the nucleus of a cell.

With regard to the step of providing a biological sample from the subject, the term "biological sample" as used herein refers to any body fluid or tissue potentially comprising the presently-disclosed biomarkers, including geminin, c-Abl, or both. In some embodiments, for example, the biological sample can be a blood sample, a serum sample, a plasma sample, or sub-fractions thereof. In some embodiments, the biological sample is a tissue biopsy, such as a tissue biopsy containing cancerous cells or cells suspected to be cancerous.

Turning now to the step of identifying one or more markers in the biological sample, various methods known to those skilled in the art can be used to identify the one or more markers in the provided biological sample. In some embodiments, determining the amount of biomarkers in samples comprises using an RNA measuring assay to measure mRNA encoding biomarker polypeptides in the sample and/or using a protein measuring assay to measure amounts of biomarker polypeptides in the sample.

In certain embodiments, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for geminin, c-Abl, or both can be immobilized on a substrate and provided for use in practicing a method in accordance with the present subject matter.

With regard to determining amounts of biomarker polypeptides in samples, in some embodiments, mass spectrometry and/or immunoassay devices and methods can be used to measure biomarker polypeptides in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the marker peptides are analyzed using an immunoassay. The presence or amount of a marker (e.g., geminin, c-Abl, or both) can be determined using antibodies or fragments thereof specific for each marker and detecting specific binding. For example, in some embodiments, the antibody specifically binds geminin, which is inclusive of antibodies that bind the full-length peptide, fragments thereof, or phosphorylated forms thereof. In some embodiments, the antibody is a monoclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments of the presently-disclosed methods that require the location of one or more of the biomarkers to be determined, various immunohistochemistry techniques known to those of ordinary skill in the art can be utilized to determine the location of a biomarker in the cell of a subject (e.g., in the nucleus of a cell). Furthermore, it is contemplated that, in some embodiments, the nucleus of one or more cells present in a biological sample obtained from a subject can be isolated from the remainder of the cells, such as by centrifugation, and the amount of a biomarker can be determined directly in a nuclear fraction using any of the methodologies described herein.

In some embodiments, mass spectrometry (MS) analysis can be used alone or in combination with other methods (e.g., immunoassays) to determine the presence and/or quantity of the one or more biomarkers of interest (e.g., geminin, c-Abl, or both) in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

Although certain embodiments of the method only call for a qualitative assessment of the presence or absence of the one or more markers in the biological sample, other embodiments of the method call for a quantitative assessment of the amount of each of the one or more markers in the biological sample. Such quantitative assessments can be made, for example, using one of the above mentioned methods, as will be understood by those skilled in the art.

In certain embodiments of the method, a subject is identified having a cancer treatable with a c-Abl inhibitor upon identifying in a biological sample obtained from the subject one or more markers selected from geminin, c-Abl, or both. In other embodiments of the method, the identification of one or more of such markers in a biological sample obtained from the subject results in the subject being identified as having a risk of a cancer treatable with a c-Abl inhibitor.

In certain embodiments of the method, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of protein marker as a function of assay units, i.e., fluorescent signal intensity, if a fluorescent signal is used. Using samples taken from multiple donors, standard curves can be provided for control levels of the one or more markers in normal tissue.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of markers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments the subject is identified as having a cancer treatable with a c-Abl inhibitor or a risk thereof if there is a measurable difference in the amount of geminin, c-Abl, or both in the sample as compared to a control level. Conversely, when no probed marker is identified in the biological sample, the subject can be identified as not having a cancer treatable with a c-Abl inhibitor, or a risk thereof, or as having a low risk of a cancer treatable with a c-Abl inhibitor.

As mentioned above, depending on the embodiment of the method, identification of the one or more markers can be a qualitative determination of the presence or absence of the markers, or it can be a quantitative determination of the concentration of the markers. In this regard, in some embodiments, the step of identifying the subject as having a cancer treatable with a c-Abl inhibitor or a risk thereof requires that certain threshold measurements are made, i.e., the levels of the one or more markers in the biological sample exceed control level. In certain embodiments of the method, the control level is any detectable level of the marker. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

In some embodiments of the presently-disclosed subject matter, a system for diagnosing a cancer treatable with a c-Abl inhibitor in a subject is provided, or a system for determining whether to initiate or continue prophylaxis or treatment of a cancer treatable with a c-Abl inhibitor in a subject is provided. Such systems can be provided, for example, as commercial kits that can be used to test a biological sample, or series of biological samples, from a subject. In some embodiments, the system includes probes for selectively binding each of one or more markers selected from geminin and c-Abl; and means for detecting the binding of said probes to said one or more markers. The system can also include certain samples for use as controls. The system can further include one or more standard curves providing levels of markers as a function of assay units.

In some embodiments, a system for the analysis of biomarkers is provided that comprises antibodies having specificity for one or more markers associated with a cancer treatable with a c-Abl inhibitor, including geminin and c-Abl. Such a system can comprise devices and reagents for the analysis of at least one test sample. The system can further comprise instructions for using the system and conducting the analysis.

Optionally the systems can contain one or more reagents or devices for converting a marker level to a diagnosis or prognosis of the subject.

Further provided, in some embodiments of the presently-disclosed subject matter, are methods for treating a cancer. In some embodiments, a method for treating a cancer is provided that comprises the steps of: identifying a subject as having a cancer treatable with a c-Abl inhibitor if there is a measurable difference in the amount of geminin, c-Abl, or both in a biological sample obtained from the subject; and administering an effective amount of a c-Abl inhibitor to the subject. In some embodiments, the c-Abl inhibitor is imatinab or nilotinib.

In some embodiments of the presently-disclosed therapeutic method, the c-Abl inhibitor is an siRNA molecule specific for silencing c-Abl or geminin. The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. One skilled in the art will recognize that any number of suitable common techniques can be used to introduce the siRNAs into a target cell, including nanoparticles, recombinant viruses, and liposomes. In some embodiments, a vector encoding the RNA is introduced to the target cell or tissue to treat a cancer treatable with a c-Abl inhibitor.

As used herein, the terms "treatment" or "treating" relate to any treatment of a condition of interest (e.g., a cancer treatable with a c-Abl inhibitor), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

For administration of a therapeutic composition as disclosed herein (e.g., a c-Abl inhibitor), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m2.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently-disclosed subject matter are typically administered in amount effective to achieve the desired response. As such, the term "effective amount" is used herein to refer to an amount of the therapeutic composition (e.g., a c-Abl inhibitor) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

Still further provided, in some embodiments of the presently-disclosed subject matter, are methods for identifying a compound that inhibits c-Abl. In some embodiments, a method for identifying a compound that inhibits c-Abl is provided that comprises the steps of providing a cell that expresses geminin, contacting the cell with a test compound, and then determining whether phosphorylation of geminin is decreased in the presence of the test compound, such that a decrease in phosphorylation of geminin identifies the compound as useful for inhibiting c-Abl. In some embodiments, determining whether phosphorylation of geminin is decreased comprises determining whether phosphorylation of geminin is decreased at tyrosine 150. In some embodiments of the screening methods, the screening methods further comprise the step of determining an amount of geminin in the cell subsequent to contacting the cell with a test compound, such that a decrease in the amount of geminin in the cell as compared to a control level identifies the compound as useful for inhibiting c-Abl.

In still further embodiments of the screening methods of the presently-disclosed subject matter, the step of providing a cell expressing geminin comprises providing a cell that overexpresses geminin. In such embodiments, the screening methods can further comprise the step of determining a number of chromosomes in the geminin-overexpressing cell such that a reduction in aneuploidy in the geminin-overexpressing cell can then be used to identify a test compound as one that is useful for inhibiting c-Abl. In other embodiments that make use of geminin-overexpressing cells, the screening methods further comprise the step of determining an amount of apoptosis in the cell that overexpresses geminin subsequent to contacting the cell with the test compound, such that an increase in apoptosis can be used to identify a compound as one that is useful for inhibiting c-Abl.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods

Cell Culture and Drug Treatment.

Breast cancer cell lines were maintained in RPMI medium (Invitrogen, Carlsbad, Calif.) supplemented with 10% FBS and antibiotics. Maintenance of HME cells was performed as described previously [20,22]. Cells were treated with 5 µM ZM477493 (Toronto Research Chemicals Inc., North York, ON), 100 ng/ml colcemid (Sigma, St. Louis, Mo.), 250 ng/ml Nocodazole (Sigma), 10 µM Taxol (Sigma). PI or FITC-conjugated anti-BrdU FACS analysis was performed as in [20]. Annexin-V was performed according to manufacturer's instructions (BD Biosciences, 556547, San Jose, Calif.).

Antibodies.

The antibody against geminin is a monoclonal produced previously [20], rabbit anti-gamma-tubulin (Abcam, ab11320, Cambridge, Mass.), mouse anti-myc-tag (Santa Cruz Biotechnology Inc., 9e10, sc-40, Santa Cruz, Calif.), mouse anti-actin (Calbiochem, cat. No. cp01-1e2, San Diego, Calif.), mouse anti-his (Invitrogen, 46-0284), rabbit anti-p-(s10)-h3 (d2c8, Abcam, ab3465), rabbit anti aurora b (Abcam, ab2254), rabbit anti-p-t232-aurora b (Abcam, ab61074), rabbit anti-incenp (Abcam, ab12183), anti-cd34 [mec 14.7]—hematopoietic stem cell marker (ab8158), mouse anti-cytokeratin 5/6 (Abcam, ab17133) and rat anti-f 4/80 (Abcam, ab6640), rabbit igg isotype control (Abcam, ab 4340).

Transit and Stable Transfection.

Twenty µg of pcDNA3.1-Myc-wild type, Y98A, Y111A or Y150A geminin variants were transfected into 50% confluence HME cells using Lipofectamine™ PLUS reagent (Invitrogen) in 8 chambers slides. Clontech kit Rev-Tre/Tet-ON inducible system was used (Clontech, Palo Alto, Calif.). Wild type geminin cDNA was amplified from HME total RNA using primers that amplify the whole cDNA including portions from the 5'- and the 3'-UTRs. Using site-directed mutagenesis kit (NEB, Beverly, Mass.) and suitable primers, the Rev-Tre-GemY98A, Y111A or Y150A were generated. GST-H3 expression plasmid was also generated using PCR technique in the pGEX-4T2.

Virus and Protein Expression.

Retroviruses production was done using standard protocols. After infection 10 hygromycin selected clones were tested for the expression of the exogenous geminin using anti-His Western blot. The GST-fused H3 was expressed in competent bacteria "One shot BL-21 star (DE3) pLysS" (Invitrogen), induced with IPTG and purified on Glutathione Sepharose™ 4B beads (GSSH), and eluted from the beads using 10 mM of Glutathione in 50 mM Tris-HCl pH 8.0.

Real Time RT/PCR Assays.

Total RNA was isolated after treatments using TRIzol reagent (Invitrogen) and treated with a DNA-free kit (Ambion, Austin, Tex.) to eliminate genomic DNA contamination. Quantitative RT/PCR analyses were performed according to standard protocols using iQ SYBR® Green Supermix (Bio-Rad Laboratories, Hercules, Calif.) using primers. Triplicate $C_T$ values were analyzed in Microsoft Excel using the comparative $C_T$ ($\Delta\Delta C_T$) method as described by the manufacturer (Applied Biosystems, Foster City, Calif.). The amount of target ($2^{-\Delta\Delta C_T}$) was obtained by normalization to an endogenous reference (18S RNA) and relative to a calibrator. Chromatin and soluble nuclear extracts purification and immunoprecipitation were performed using a previous protocol [20].

Metaphase Spread.

100 ng/ml colcemid was added directly to culture dish and dish was swirled, incubated for 1 hr. Cells were then trypsinized and washed and gently resuspended in PBS. 10 ml of 0.075M KCl was drop wise added and the cells were incubated at 37° C. (in a water bath) for 5-10 mins. Cells were then centrifuged at 900 rpm for 5 minutes and KCl was removed. 5 ml of freshly prepared fixative (3:1 Methanol/Acetic acid) was added drop wise to the cells and carefully mixed. Cells were centrifuged at 900 rpm for 5 minutes and the fixative was removed. This step was repeated 2 more times. Finally, all but 300 µl of the fixative media was removed and cells were dropped from approximately 18 inches onto an angled, humidified microscope slide. Slides were air-dry for at least 10 mins and cells were stained with propidium iodide (PI) or Giemsa.

RNA Interference Experiment.

Geminin siRNA that had been previously described was used [20,22], and transfection of siRNAs in HME cells was performed using Oligofectamine 2000 (Invitrogen) according to the manufacturer's instructions.

TUNEL Detection Protocol.

The Fluorescein FragEL™ DNA Fragmentation Detection kit (Calbiochem) was used according to the supplier's protocol.

Soft Agar Colony Formation Assay.

A mixture of equal volumes of the 1% Nobel agar (Difco, Houston, Tex.) and HME medium were layered on a 6 well plate and allowed to settle. 5,000 cells were mixed with 0.7% of the same agar prepared in pre-warmed (approximately 40° C.) HME medium, and were layered on the agar dishes and incubated at 37° C. in a humidified incubator for 2-3 weeks in the presence or absence of 2 µg/ml Dox. Cells were then stained with 0.5 ml of 0.005% Crystal Violet for more than 1 hour, and colonies were counted under a light microscope. HEK293T cells were used as a positive control and IMR90 cells as a negative control.

Tissue Samples and Immunohistochemical Analysis of Paraffin-Embedded Tumor Samples.

Tissue microarrays were purchased from Biomax (Rockville, Md.), or were constructed at the University of Hawaii Cancer Center using tissue from the SEER (Surveillance Epidemiology and End Results) collection. All human tumor samples experiments were approved by a University of Hawaii IRB committee. Form tumors generated in mice and embedded in paraffin 4 µm sections were also prepared. For all antibodies used in the study, the antigen retrieval technique used was carried out by microwave treatment of the slides in sodium citrate buffer (pH 6.0) for 20 min.

Subcutaneous and Mammary Tumorigenicity Assay.

All animal experiments were approved by the University of Hawaii IACUC committee and University of Mississippi Medical Center IACUC committee. Six- to eight-week-old anaesthetized immune-compromised athymic SCID (NOD.CB17-Prkdc$^{scid}$/J, Jackson Laboratory) mice were injected with human mammary epithelial (HME) cells ($5\times10^6$) resuspended in 200 µl of HME medium/matrigel (1:1) using a 25-gauge needle. Tumor initiation was defined as the time when tumors were 3 mm in diameter. Mice were sacrificed when the tumors grew to greater than 1.5 cm in diameter or after 12 wks of monitoring. Tumor volume was calculated with the formula $4/3\pi r^3$ (where r is the tumor radius). At the end of the experiments tumors were dissected out, weighed and then fixed in formalin, and subsequently cut at 4 µm for histological and immunohistochemical analysis.

In Vivo Measurement and Imaging of Subcutaneous or Mammary Tumors.

Tumor formation was analyzed with IVIS luciferase machine (Xenogen, Alameda, Calif.) weekly and tumor size was measured every third day by calipers. To analyze tumor formation using the in vivo system, mice were intraperitoneally injected using a 30G needle with 100 µl of D-luciferin solution (Xenogen) prepared at 15 mg/mL in PBS. Mice were then anesthetized using a mix of oxygen and isoflurane gas. Anesthetized animals were maintained in sleep during the imaging procedures by placing the animal right-side (injection side) up and its nose in a nose cone with a flow of anesthesia gas.

Imatinib and Doxorubicin Treatments.

Geminin overexpressing cells were injected subcutaneously or orthotopically (in mammary gland) in SCID mice as described above. When tumors reached 0.5-0.75 cm$^3$ in volume the treatments were initiated. Some mice received no treatment, some received 5 mg/kg/day doxorubicin, some received 50 mg/kg/day imatinib and yet another group received both drugs at the same concentrations. Mice were treated for 5 days and were rested for 2 days and tumor size was measured daily using calipers. At the end of the experiments tumors were dissected out, weighed and fixed in formalin, and cut at 4 µm for histological and immunohistochemical analysis.

Statistical Analysis.

Comparisons of treatment outcomes were tested for statistical differences using the Student t-test for paired data. The association of mRNA transcript expression with various clinico-pathologic parameters was also analyzed. Statistical significance was assumed at a p-value are *≤0.05, ≤0.01 and *≤0.001.

Example 1

Localization of Geminin During $G_2$/M/Early $G_1$ in HME Cells

Figure 1B:
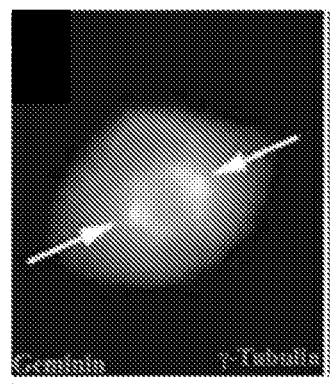
Figure 1C:
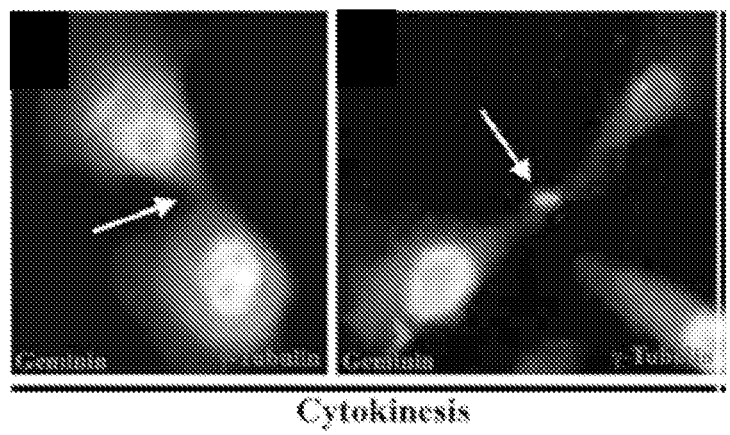

It is appreciated that geminin silencing in HME cells arrests cytokinesis with little effect on S phase progression. To expand these results, evidence of geminin localization was sought in $G_2$/M/early $G_1$ HME cells. Synchronized HME cells in different part of the cell cycle were immunostained with anti-γ-tubulin (red) and -geminin (green). It was found that geminin was localized with γ-tubulin to centrosomes in late interphase (FIG. 1A), to the spindle in metaphase (FIG. 1B), and to the cleavage furrow and midbody in cytokinesis (FIG. 1C).

Figure 1D:
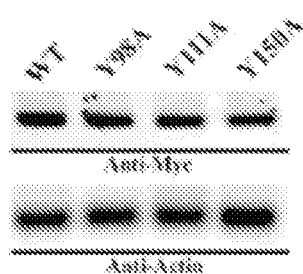
Figure 1E:
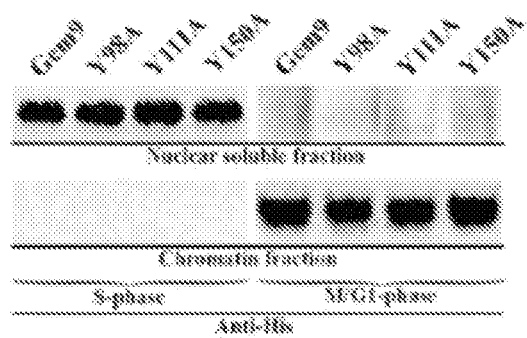

It is also appreciated that geminin is a serine/threonine (S/T) phosphorylated soluble protein in S-phase, and a tyrosine (Y) phosphorylated chromatin-bound protein in $G_2$/M/early $G_1$ phase, and that geminin contains three Y residues, at positions 98, 111 and 150. Using site directed mutagenesis, each Y was separately mutated to alanine (A) or phenylalanine (F). Wild type (WT) and mutant cDNAs were cloned into a vector that introduces a Myc tag upstream of each protein. Anti-Myc immunoblotting on sonicated extracts of transiently transfected (48 h) HME cells showed that all proteins were expressed at similar levels (FIG. 1D). WT and mutant cDNAs were also cloned into a vector that puts expression of all cDNAs under a doxycycline inducible promoter and introduces a His tag downstream of each protein. Inducible cell lines were generated (2 WT cell lines Gem9 and Gem10 were chosen to analyze further in this study). Anti-His immunoblotting on 72 h induced (with 2 µg/ml doxycycline, Dox) WT (hereafter Gem9), GemY98A, GemY111A or GemY150A cells showed that all proteins like endogenous geminin are located in the soluble nuclear fraction in S phase cells, while on the chromatin in M/G$_1$ phase cells (FIG. 1E).

Figure 1F:
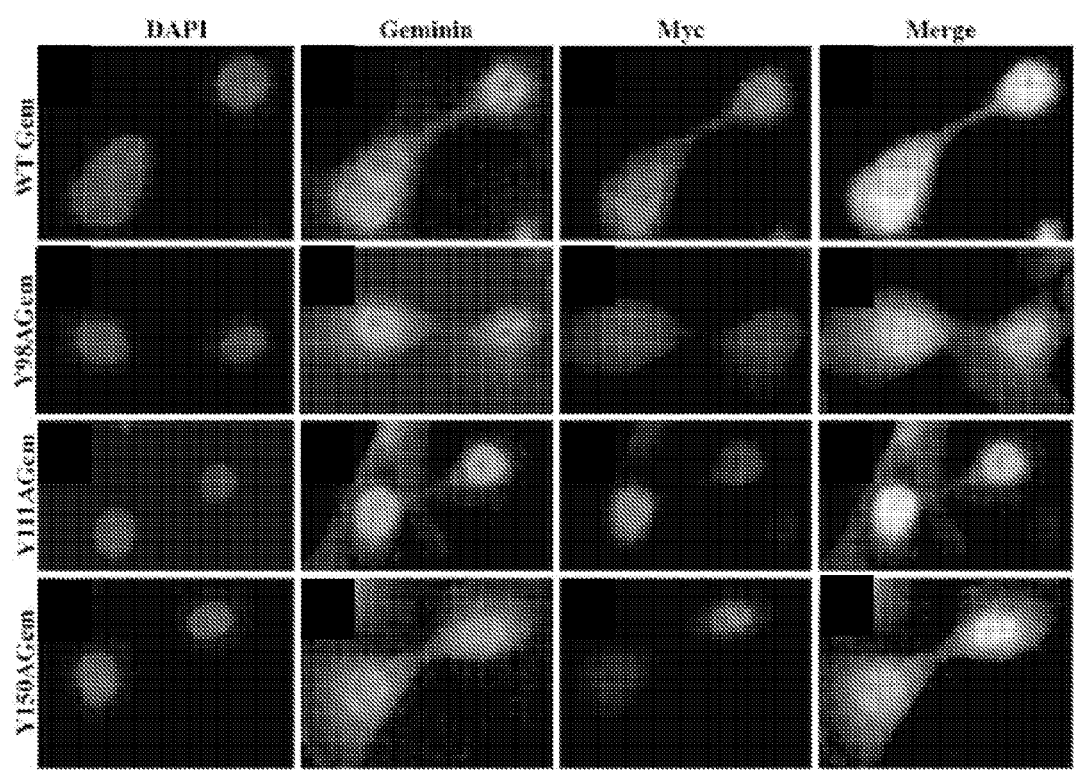

To study the effect of geminin Y phosphorylation on protein localization in G$_2$/M/early G$_1$ cells, HME cells were transiently transfected with Myc-tagged WT, Y98A, Y111A or Y150A cDNAs. Forty-eight hours later, cells were immunostained with anti-geminin (to detect endogenous protein) and anti-Myc (to detect exogenous proteins) antibodies. Exogenous WT and not Y98A, Y111A, or Y150A geminin (FIG. 1F) was co-localized with endogenous geminin at the cleavage furrow, centrosome, spindle and midbody localization. Taken together, these data indicated that while geminin phosphorylation on all tyrosine residues at the same time is not required for protein nuclear and chromatin localization, it is required for protein localization to the centrosome, spindle, cleavage furrow, and midbody in G$_2$/M/early G$_1$ cells. It is further possible that Y phosphorylation activates geminin proposed cytokinetic function.

Example 2

Figures 2A, 2B:
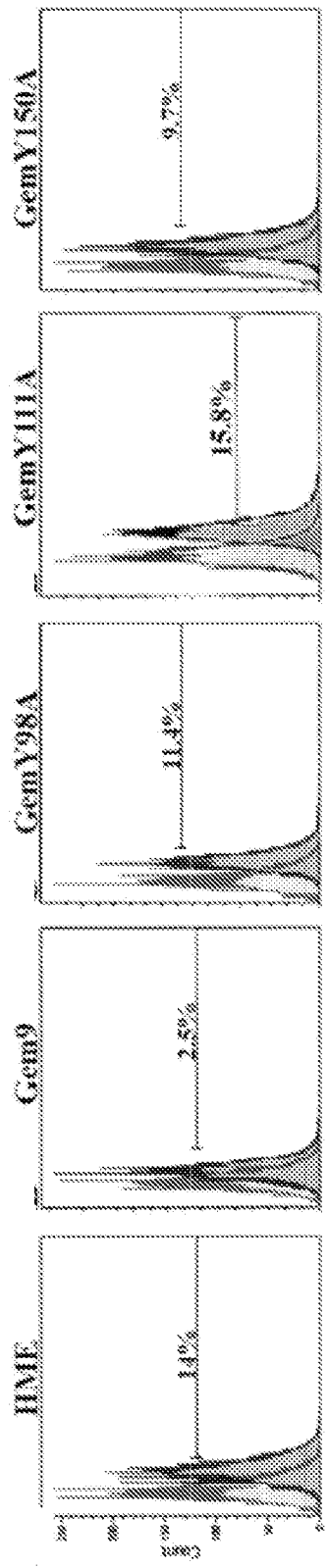
FIGS. 2A-2B include graphs showing the analysis of histone H3 phosphorylation and ploidy in HME cells overexpressing WT or Y-to-A geminin mutants, including: graphs showing p-(S10)-H3 expressing populations in HME cells, and induced (96 h) Gem9, GemY98A, GemY111A, and GemY150A cells as measured by fluorescence-activated cell sorting (FACS) (FIG. 2A); and graphs showing the cell cycle analysis of uninduced Gem9 or induced (96 h) Gem9, GemY98A, GemY111A and GemY150A cells, where percentages of tetraploid/aneuploid populations are shown and circled as measured by FACS (FIG. 2B, see circles), and where $R1=G_0/G_1$, $R3/R4/R5=$early/mid/late S, $R2=G_2/M$ and $R6=>4N$ cells.

Geminin Overexpression Suppresses H3-(S10) Phosphorylation and Promotes Tetraploidy/Aneuploidy in HME Cells The majority of geminin silenced cells were positive for the mitotic marker p-(S10)-H3 and arrested at cytokinesis. To examine the effect of Y phosphorylated/activated geminin overexpression on H3-(S10) phosphorylation, Gem9, GemY98A, GemY111A and GemY150A cells were first grown in the presence of 2 µg/ml Dox (hereafter induced) for 96 h. Aliquots were then labeled with FITC-p-H3(S10) antibody or FITC-IgG (same isotype) and analyzed by FACS. Control HME cells showed 14±2% p-(S10)-H3-positive cells (FIG. 2A). Induced Gem9 cells showed 2.5±0.5% (p-value=0.005), induced GemY98A showed 11.4±4% (p=0.4), induced GemY111A showed 15.6±2% (p=0.8) and induced GemY150A showed 9.7±5% (p=0.06) p-(S10)-H3-positive cells (FIG. 2A).

Second, to investigate the effect of overexpressing Y phosphorylated/activated geminin on ploidy, Gem9, GemY98A, GemY111A and GemY150A were induced for 48 hrs followed by addition of Aphidicoline (1 µg/ml, Aph) to cells for another 24 hrs. After washing off the Aph, cells were incubated with 20 µM of BrdU for an additional 24 hrs. Cells were then labeled with FITC anti-BrdU antibody and propidium iodine (PI) and analyzed by fluorescence activated cell sorting (FACS). Control uninduced Gem9 3±1% cells showed greater than 4N DNA content (FIG. 2B). In induced Gem9 35±5% (p=0.0014), in induced GemY98A 4±1% (p=0.3), in induced GemY111A 11±4% (p=0.4), and in induced GemY150A 5±2% (p=0.5) cells showed greater than 4N DNA content (FIG. 2B). Taken together, these data indicated that overexpression of Y phosphorylated/activated geminin suppresses phosphorylation of (S10)-H3 and triggers tetraploidy/aneuploidy in HME cells, in part, through promoting cytokinesis skipping.

Example 3

Tyrosine Mutant Geminin Induces Apoptosis Instead of Tetraploidy/Aneuploidy in HME Cells To confirm that the foregoing results were indeed geminin-dependent effects, HME, Gem9, GemY98A, GemY111A and GemY150A cells were grown in the presence of Dox for 96 hrs. HME and Gem9 cells were also transfected with luciferase (control) or geminin specific siRNA during the last 72 hrs. Aliquots of each culture were labeled with PI and cell cycle profile was measured using FACS. Gem9 cells growing in Dox expressed 3- to 4-fold geminin above endogenous level in HME cells growing in Dox, and geminin siRNA significantly suppressed geminin expression in both cell lines (FIG. 3A, inset).

Figure 3A:
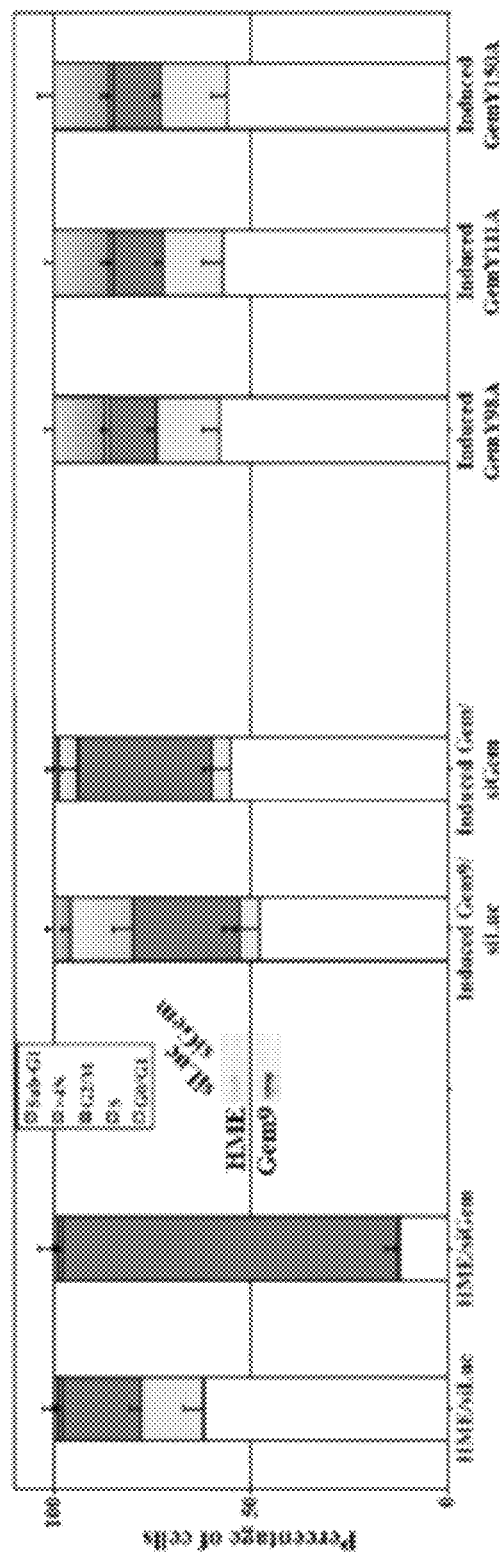
FIG. 3A-3E include images and graphs showing an analysis of tyrosine mutant geminin variants, including a graph showing a cell cycle analysis of HME and induced (96 h) Gem9, GemY98A, GemY111A and GemY150A cells, where HME and Gem9 cells were also transfected with luciferase or geminin shRNA during the last 72 h of the culture period and cell cycle profiles (percentages are shown) were measured by FACS, and where the inset image shows the knockdown effect of geminin shRNA in HME and induced Gem9 cells (FIG. 3A); images showing terminal deoxynucleotidyl transferase dUTP nick end labeling (TUNEL) analysis of HME and induced (96 h) Gem9, GemY98A, GemY111A and GemY150A cells (FIG. 3B); a graph showing the number of apoptotic cells (TUNEL-positive) per field measured in the cultures shown in FIG. 3B (FIG. 3C); an image of a western blot showing the expression of geminin and pro-survival proteins in sonicates (total cellular proteins) of HME and induced (96) Gem9, GemY98A, GemY111A and GemY150A (FIG. 3D); and phase contrast images of HME and induced (168 h) Gem9, GemY98A, GemY111A and GemY150A (FIG. 3E)

In line with previous data [20], geminin-silencing arrested HME cells in G$_2$/M phase (FIG. 3A, left). WT geminin overexpression accelerated the cell cycle instead and triggered formation of cells with greater than 4N DNA content (FIG. 3A, middle). Geminin silencing in induced Gem9 cells restored normal cell cycle progression and prevented the formation of cells with greater than 4N DNA content (FIG. 3A, middle). Meanwhile, induced GemY98A, GemY111A or GemY150A cells showed near normal cell cycle profile, and had low number of cells with greater than 4N DNA content, but showed high numbers of sub-G$_1$ (i.e. dying) cells (FIG. 3A, right). Taken together these data indicated that overexpression of Y phosphorylated/activated geminin induced tetraploidy/aneuploidy, whereas overexpression of tyrosine mutant geminin induced cell death.

To investigate further, induced (48 h) Gem9, GemY98A, GemY111A and GemY150A cells were labeled with annexin V/PI and analyzed by FACS. Control HME cells showed 81% live (i.e. PI$^-$/V$^-$), 12% necrotic (i.e. PI$^+$/V$^-$), and 7% apoptotic (i.e. PI$^-$/V$^+$+PI$^+$/V$^+$) cells (FIG. 8A). Induced Gem9 cells showed 89% PI$^-$/V$^-$ (p<0.05), 7% PI$^+$/V$^-$ (p<0.05), and 4% PI$^-$/V$^+$+PI$^+$/V$^+$ (p<0.5) cells (FIG. 8B). Meanwhile, induced GemY98A showed 61% PI$^-$/V$^-$ (p<0.05), 30% PI$^+$/V$^-$ (p<0.05) and 9% PI$^-$/V$^+$+PI$^+$/V$^+$ (p<0.05) cells (FIG. 8C), induced GemY111A showed 40% PI$^-$/V$^-$ (p<0.05), 51% PI$^+$/V$^-$ (p<0.05), and 9% PI$^-$/V$^+$+PI$^+$/V$^-$ (p<0.05) cells (FIG. 8D) and induced GemY150A showed 67% PI$^-$/V$^-$ (p<0.05), 24% PI$^+$/V$^-$ (p<0.05) and 9% PI$^-$/V$^+$+PI$^+$/V$^+$ (p<0.05) cells (FIG. 8E).

Figure 3B:
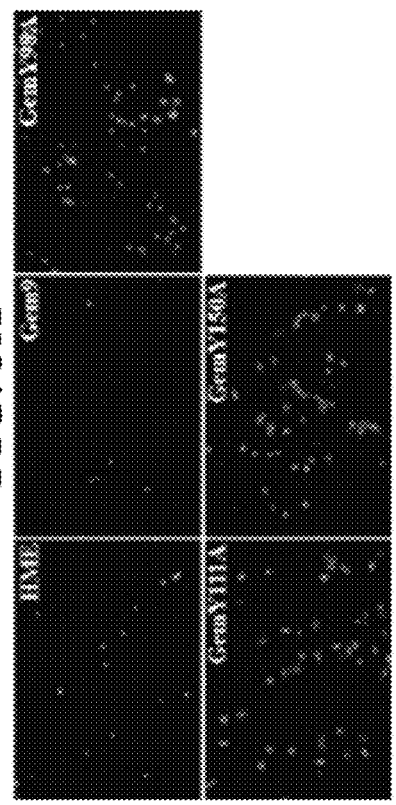
Figure 3C:
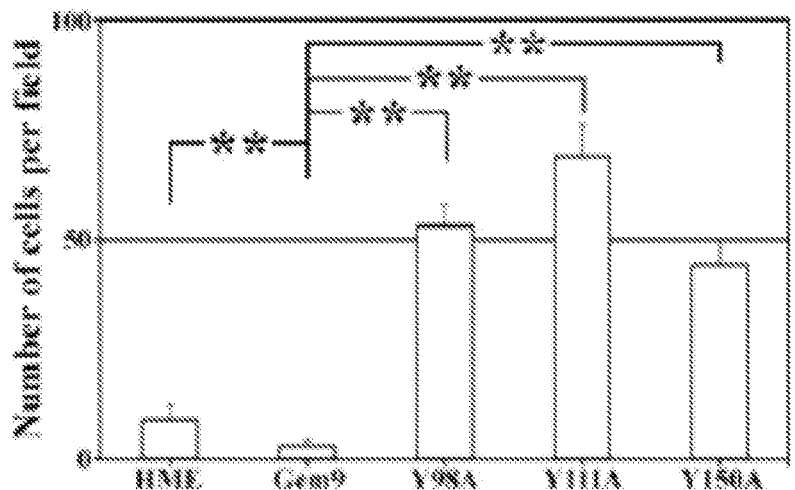

TUNEL analysis on induced (96 h) Gem9, GemY98A, GemY111A and GemY150A cells showed that compared to control HME cells that had 9±2 TUNEL-positive cells/filed, induced Gem9 cells had only 4±1 TUNEL-positive cells/field (p<0.05, FIGS. 3B and 3C). Meanwhile, induced GemY98A showed 53±5 (p<0.05), GemY111A 72±8 (p<0.05) and GemY150A 47±6 (p<0.05) TUNEL-positive cells/field (FIGS. 3B and 3C).

Figure 3D:
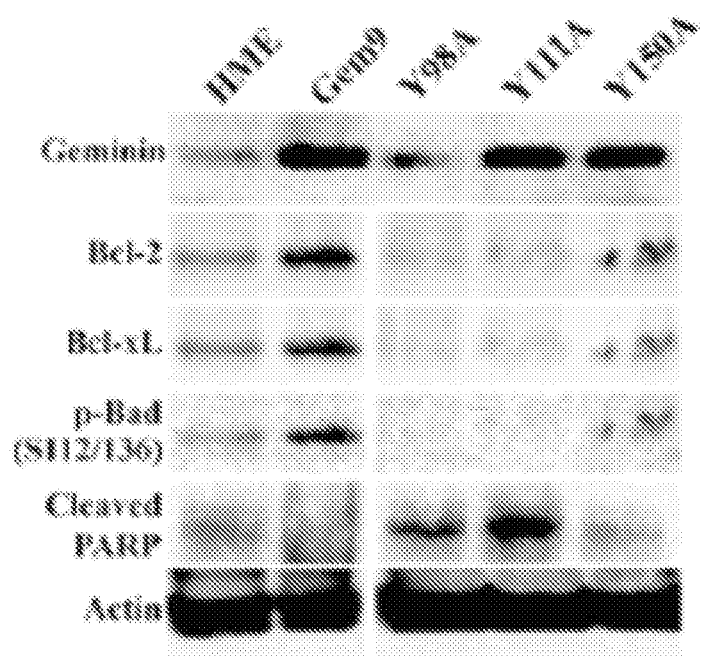

To analyze the findings on a molecular level, induced (96 h) Gem9, GemY98A, GemY111A and GemY150A cells were sonicated and whole cell extracts were analyzed for the expression of several pro-survival proteins by immunoblotting. Compared to control HME cells, high expression levels of the pro-survival proteins, Bcl-2, Bcl-xL and p-Bad were found in induced Gem9 cells, whereas lower expression (even below HME levels) of these proteins was detected in all mutant cell lines (FIG. 3D). Consistently, low but detectable levels of cleaved PARP (an early sign of apoptosis) was detected in HME cells, no such cleavage was detected in induced Gem9 cells, but high levels of cleaved PARP were detected in all mutant cell lines (FIG. 3D).

Figure 3E:
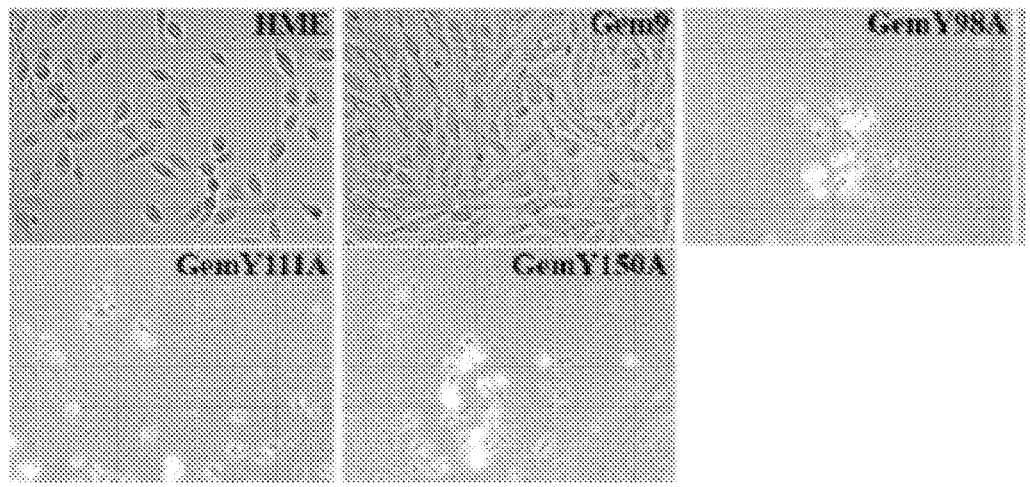

When 5000 Gem9, GemY98A, GemY111A or GemY150A cells were induced for 168 h, it was found that compared to HME (also plated at 5000 cells), prolonged overexpression of wild type geminin dramatically increased the number of cells (FIG. 3E). Meanwhile prolonged overexpression of any of the Y mutants virtually killed all the cells (FIG. 3E). Overall, these data indicated that overexpression of Y phosphorylated/activated geminin triggers formation and survival of tetraploid/aneuploid cells, and that mutating any of the three Y residues in geminin converts the overexpressed protein to a death-inducer protein.

Example 4

Figure 4A:
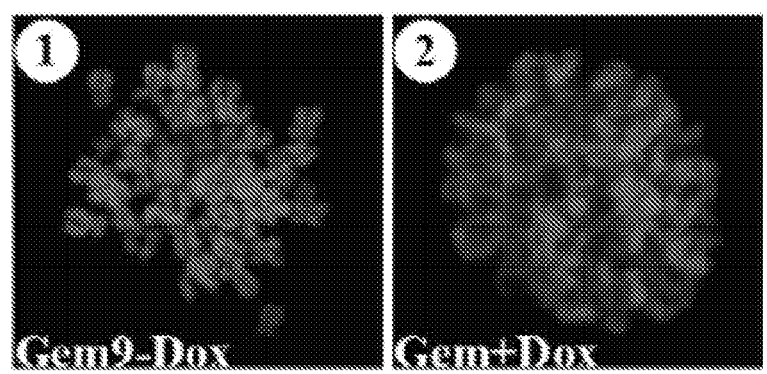
FIGS. 4A-4H include images and graphs showing the effect of geminin overexpression on chromosome condensation, centrosome number, cytokinesis, ploidy, and transformation in HME cells, in vitro, including images of propidium iodide (PI) stained metaphase spreads of uninduced (1) or induced (96 h, 2) Gem9 cells (FIG. 4A); images of γ-tubulin labeled cells of uninduced (1) or induced (96 h, 2) Gem9 cells, where the arrows show the number of centrosomes in each culture (FIG. 4B); images of γ-tubulin labeled cells in uninduced (1) or induced (96 h, 2) Gem9 cells (FIG. 4C), where the arrows show the number of nuclei in each cell; a graph showing the quantitative analysis of the percentage of cells showing multiple centrosomes, showing multi-nucleation, and aborting cytokinesis (FIG. 4D); images showing a time-lapse analysis of induced Gem9 cells (14 days), where cell "A" divided normally into 2 daughter cells, and where cells "1, 2 and 3" attempted to undergo cytokinesis, but failed and became tetraploid (FIG. 4E); images of giemsa-stained metaphase chromosomes of Gem9 grown in the absence (1 and 3) or presence (2 and 4) of 2 μg/ml of doxorubicin for 8 weeks (FIG. 4F); images of soft agar colony formation assays using uninduced (1) or induced Gem9 (2) cells (FIG. 4G); and a graph showing a quantitative analysis of the soft agar experiments shown in FIG. 4G (FIG. 4H)

Geminin Overexpression Induction of Chromosome Decondensation, Centrosome Multiplication, Multi-Nucleation and Aborted Cytokinesis It is appreciated that diminution of (S10)-H3 phosphorylation leads to chromosome condensation failure. To study whether overexpression of Y phosphorylated/activated geminin inhibits normal chromosome condensation, induced (96 h) Gem9, GemY98A, GemY111A and GemY150A cells were exposed to 10 μM of colcemid (a microtubules depolymerizing agent that arrests cells in metaphase) during the last 2 h, then were processed to metaphase-spread, PI labeled, and analyzed under a microscope. Chromosomes were condensed in HME and induced GemY98A, GemY111A or GemY150A cells by this treatment (FIG. 4A/1). In contrast, in induced Gem9 cells chromosomes were de-condensed (FIG. 4A/2), indicating that overexpression of Y phosphorylated/activated geminin suppresses chromosome condensation (i.e. induces G2 arrest) or promotes premature chromosome de-condensation (i.e. accelerates M-to-$G_1$ transition). Without wishing to be bound by any particular theory, however, it was beflived that the latter should be the favored explanation because close examination of the chromosomes in colcemid treated induced Gem9 cells revealed that they resemble $G_1$ and not $G_2/M$ chromosomes (FIG. 4A/2).

Figure 4B:
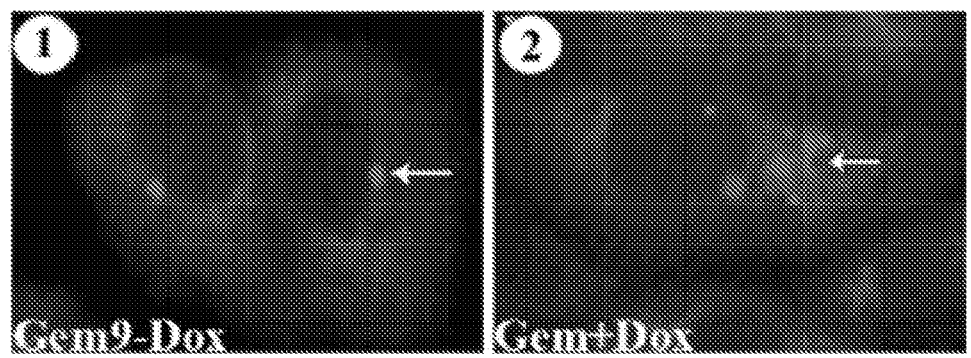
Figure 4C:
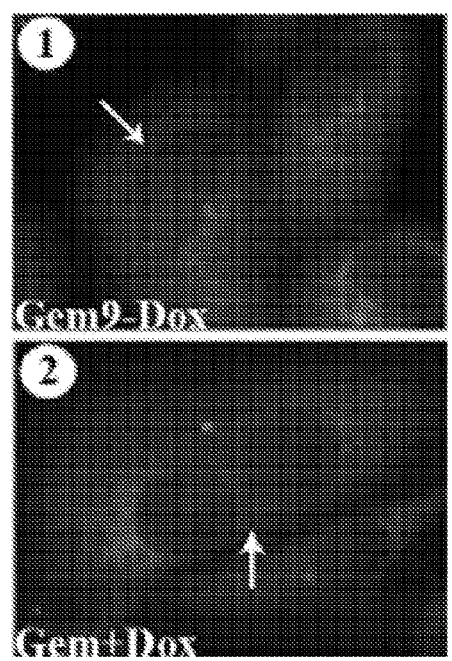
Figure 4D:
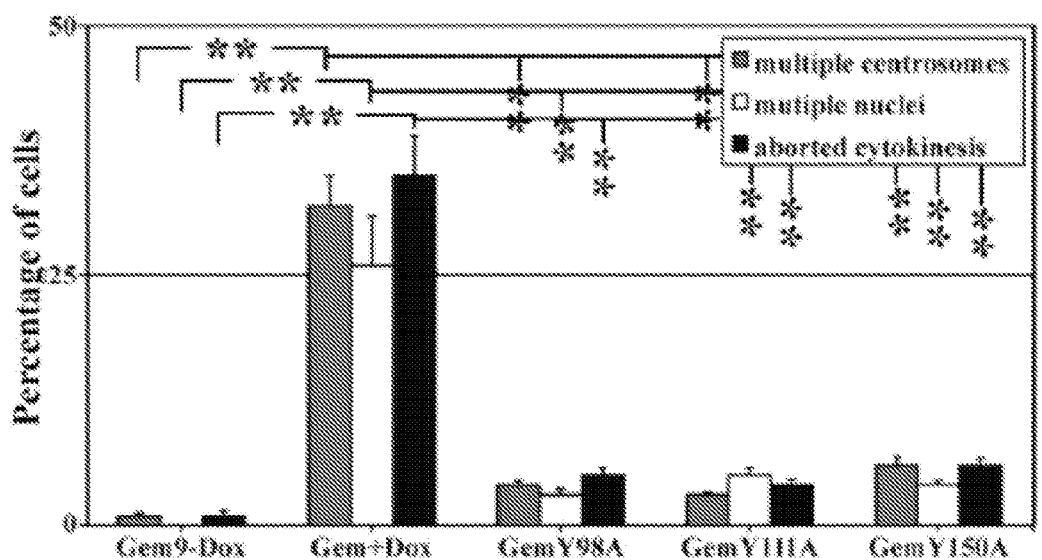

Aneuploidy is usually associated with centrosome multiplication and leads to multi-nucleation. To test whether overexpression of Y phosphorylated/activated geminin promotes centrosome multiplication and/or multi-nucleation, induced (96 h) Gem9, GemY98A, GemY111A and GemY150A were immunostained with anti-γ-tubulin (a centrosome and cell body marker) then analyzed under microscope. Compared to interphase HME (i.e. Gem9−Dox) cells that contained a single centrosome (FIG. 4B/1), induced Gem9 cells contained multiple (2-8) centrosomes (FIG. 4B/2). No such centrosome multiplication was detected in induced GemY98A, GemY111A or GemY150A cells. Quantitatively, 1±0.5% control, 32±3% ($p<0.01$) induced Gem9, 4±0.5% ($p<0.01$) GemY98A, 3±0.5% ($p<0.01$) GemY111A and 6±0.5% ($p<0.01$) GemY150A interphase cells had multiple centrosomes (FIG. 4D). Moreover, none of control cells (FIGS. 4C/1 and 4D), 26±5% induced Gem9 cells ($p<0.01$, FIGS. 4C/2 and 4D), 3±0.5% induced GemY98A cells ($p<0.01$), 5±0.5% induced GemY111A cells ($p<0.01$) and 4±0.5% induced GemY150A cells ($p<0.01$) interphase cells were multi-nucleated (FIG. 4D).

Figure 4E:
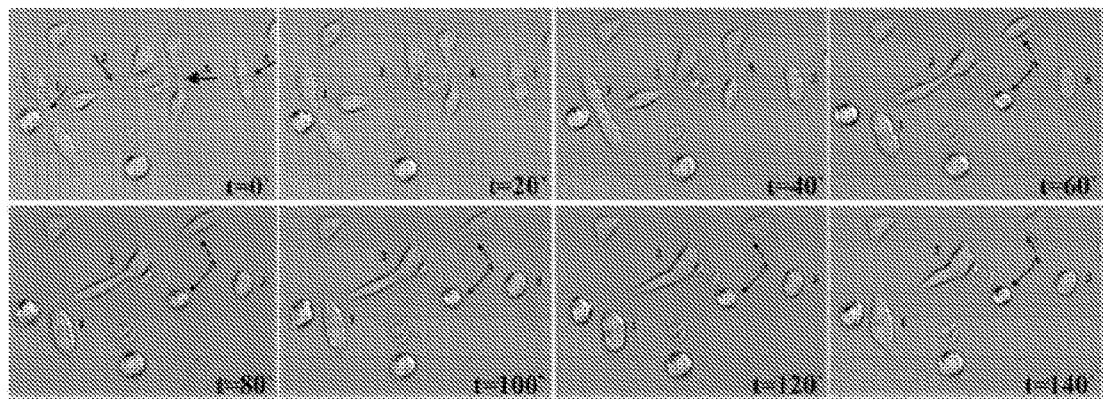

Finally, time-lapse analysis revealed that compared to only 1±0.5% of control uninduced Gem9 cells, 38±4% of induced (96) Gem9 cells attempted to undergo cytokinesis but aborted and became tetraploid/aneuploid (FIG. 4D and see example cells labeled 1, 2 and 3 in FIG. 4E as compared to the cell labeled A in FIG. 4E). Meanwhile, 5±0.5% induced GemY98A, 4±0.5% induced GemY111A and 6±0.5% induced GemY150A aborted cytokinesis (FIG. 4D). Overall, these data indicated that overexpression of Y phosphorylated/ activated geminin induced cytokinesis skipping, centrosome multiplication, multi-nucleation and the production of tetraploid/aneuploid cells.

Example 5

Geminin Overexpression Induces Aneuploidy and Transformation in HME Cells

Figure 4F:
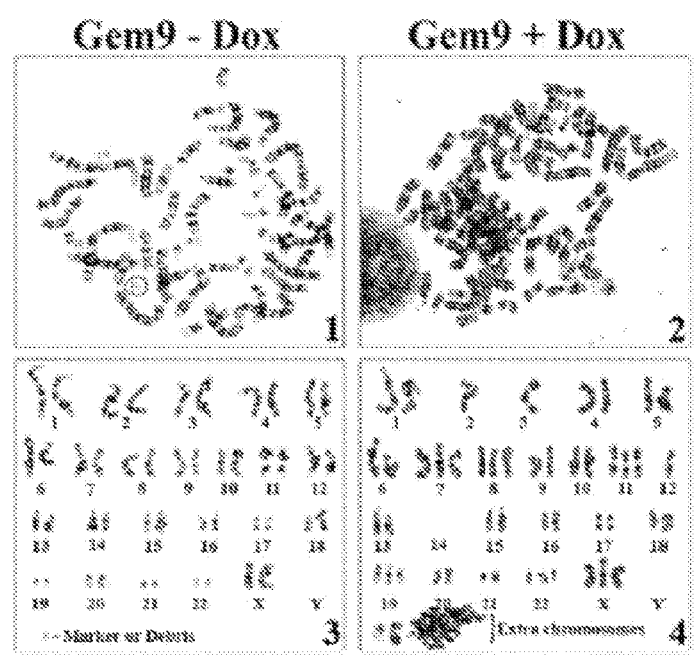
Figure 4G:
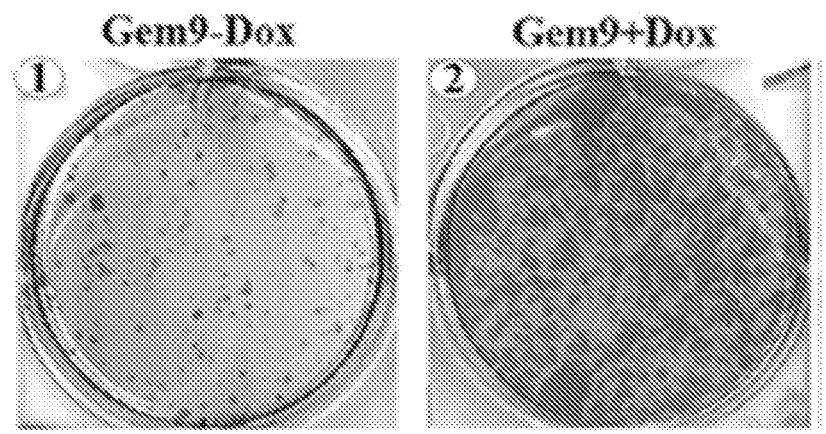
Figure 4H:
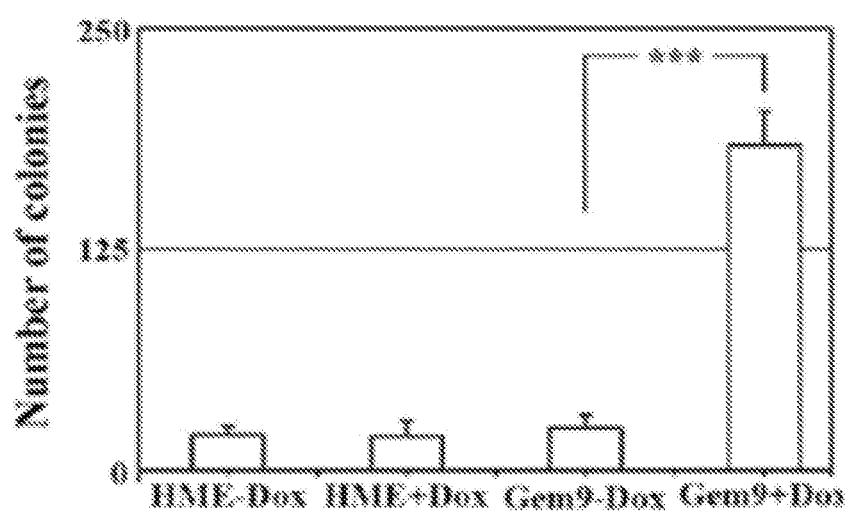

To directly show that geminin overexpression induces aneuploidy in HME cells, metaphase spread analysis was performed on long time (8 weeks) uninduced (Gem9−Dox) or induced (Gem9+Dox) cultures. Giemsa-stained chromosomes were counted in at least 100 cells. Only 1±0.5% of the uninduced Gem9 cells were aneuploid (FIG. 4F/1 and /3), whereas 36±7% of induced Gem9 cells were aneuploid ($p<0.5$, FIGS. 4F/2 and 4). To assess whether this triggers transformation in HME cells, HME and Gem9 cells were grown in the presence or absence of Dox (72 h) before they were layered on soft agar for an additional 14 days also in the presence or absence of Dox. Only few, small colonies were detected in HME and uninduced Gem9 cells at the end of the 14 days (FIGS. 4G/1 and 4H), whereas massive numbers of large size colonies were detected in induced Gem9 cultures (FIGS. 4G/2 and 4H). Taken together, these data indicated that overexpression of Y phosphorylated/activated geminin triggered formation of multiple centrosomes, multi-nucleation, tetraploidy/aneuploidy, and transformation in HME cells.

Example 6

Figure 5A:
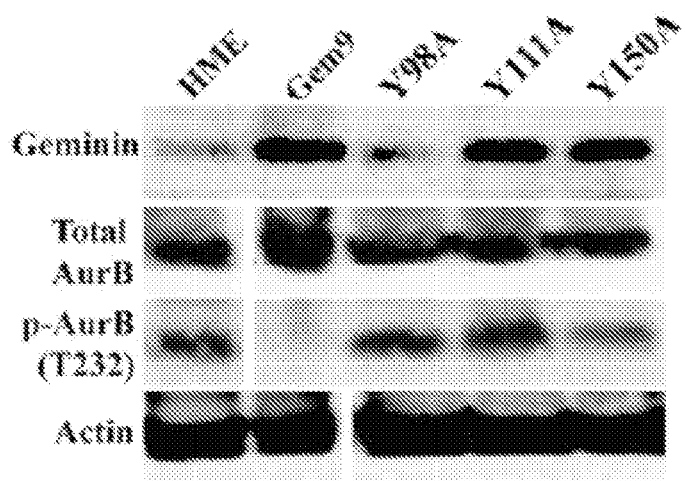
FIG. 5 includes images and graphs showing the inactivation of AurB as a result of geminin overexpression, including: an image of a western blot showing the expression of several proteins in sonicates of HME and induced (96) Gem9, GemY98A, GemY111A and GemY150A cells (FIG. 5A); an image of a western blot showing the expression of several proteins in uninduced (−) or induced (+) Gem9 cells (FIG. 5B, left), and showing the expression of immunoprecipitated AurB from uninduced (−) or induced (+) Gem9 cells (FIG. 5B, right, upper), where the immunoprecipitated AurB was used to in vitro phosphorylate GST-H3 (FIG. 5B, IVK, right); an image showing the phosphorylation of survivin on T117 in uninduced (left) or induced (right) Gem9 cells (right, lower) (FIG. 5C); an image of a western blot showing the results of immunoprecipitation of AurB from HME or induced Gem9 cells using AurB or INCENP specific antibody (FIG. 5D); and image of a western blot showing the results of immunoprecipitation of AurB from $G_1/S$, $G_2/M$ or $M/G_1$ HME cells using AurB or geminin specific antibodies (FIG. 5E); and a graph showing the effect of AurB inhibitor ZM447493 on HME or induced Gem9 cell cycle progression (FIG. 5F)

Analysis of Geminin Overexpression and Formation of Tetraploid/Aneuploid Cells Via AurB Inhibition AurB phosphorylates and activates a large number of proteins involved in chromosome condensation, segregation and cytokinesis, including (S10)-H3. The lack of p-(S10)-H3 in induced Gem9 cells (FIG. 2) led to the question of whether AurB was inactive in geminin-overexpressing cells. Induced (96 h) Gem9, GemY98A, GemY111A and GemY150A were sonicated and total cellular proteins were processed for western analysis. All cell lines showed equally high expression of WT or mutant geminin (3-4 fold above endogenous level when induced, FIG. 5A). While the expression of total AurB was equally high in HME and all induced cell lines, p-T232-AurB was virtually absent from induced Gem9, although HME control and all mutant cell lines showed high levels of it (FIG. 5A). Because these were sonicated extracts (i.e. all cellular proteins were present), it was believed that overexpression of Y phosphorylated/activated geminin inactivates AurB and does not simply mislocalize the protein in the cell.

Figure 5B:
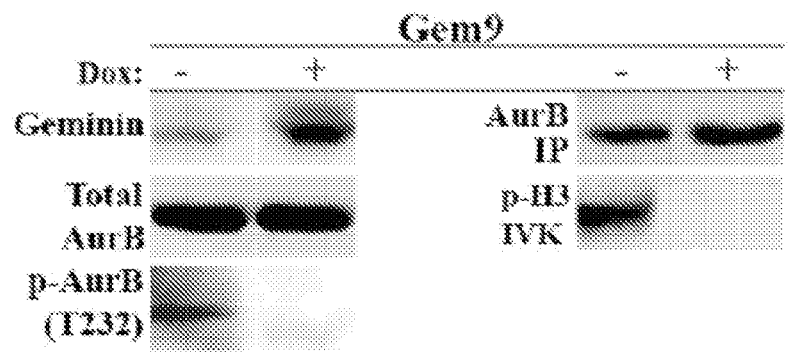
Figure 5C:
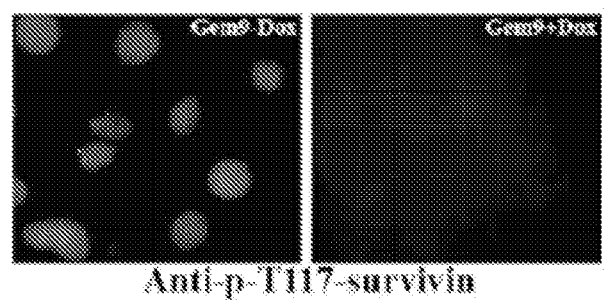

To confirm that finding further, Gem9 cells were grown in the absence or presence of 2 μg/ml Dox for 96 h followed by sonication. Immunoblotting analysis showed 3-4 fold increase in geminin level in induced compared to uninduced Gem9 cells (FIG. 5B, left). Again, while expression of total AurB was not affected by geminin overexpression, virtually no p-T232-AurB was detected in induced compared to uninduced Gem9 cells (FIG. 5B, left). Moreover, using AurB antibody, equal amounts of total AurB were immunoprecipitated from uninduced and induced Gem9 cells (FIG. 5B, right). However, only AurB immunoprecipitated from uninduced Gem9 cells was able to phosphorylate GST-H3 in in vitro kinase (IVK) assay (FIG. 5B, right). In addition, using a phospho-specific antibody, it was found that T117 on survivin (another target of AurB, [25]) was phosphorylated in uninduced (FIG. 5C, left) but not induced Gem9 cells (FIG. 5C, right). Taken together, these data confirmed the hypothesis that AurB was inactivated in cells overexpressing Y phosphorylated/activated geminin.

Example 7

Mechanism for AurB Inactivation in Geminin Overexpressing Cells

Figure 5D:
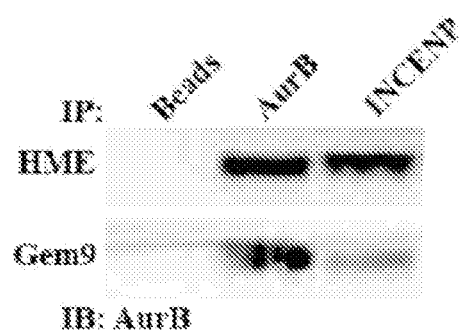
Figure 5E:
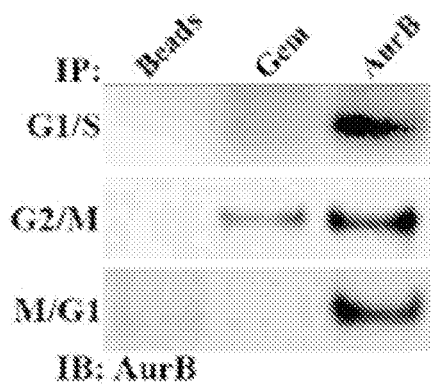

A pre-requisite for AurB autophosphorylation and activation in vivo is the binding to INCENP. To evaluate whether overexpression of Y phosphorylated/activated geminin inactivated AurB by preventing binding to INCENP, experiments were undertaken to immunoprecipitate AurB from HME or induced Gem9 (96 h) $G_2$/M cells using AurB or INCENP specific antibodies. While AurB and INCENP antibodies immunoprecipitated equal levels of AurB from HME $G_2$/M cells (FIG. 5D), from induced Gem9 $G_2$/M cells, only AurB antibody immunoprecipitated AurB. Moreover, geminin antibody immunoprecipitated AurB from $G_2$/M only (FIG. 5E), even-though AurB antibody immunoprecipitated AurB from HME in $G_1$/S, $G_2$/M and M/$G_1$ phase (FIG. 5E). These data indicated that overexpressed Y phosphorylated/activated geminin competes with INCENP for AurB binding, thus preventing AurB autophsophorylation and activation in vivo.

Example 8

Figure 5F:
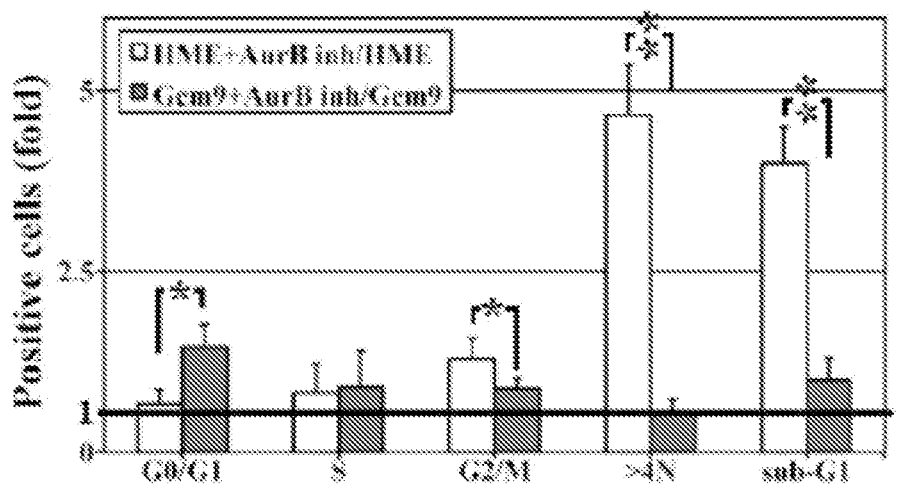

Analysis of Geminin Overexpression and Resistance to AurB Inhibitor, ZM447439 in HME Cells Since AurB is inactive in Y phosphorylated/activated geminin overexpressing cells, it was believed that AurB inhibitors would have no efficacy in geminin overexpressing cells. To evaluate that in detail, HME (or Gem9–Dox) and induced (72 h) Gem9 cells were incubated with 5 µM of ZM447439 (a specific and potent inhibitor of AurB) for an additional 24 h. To measure the effect of ZM447439 on cell cycle progression aliquots from each culture were labeled with PI and analyzed by FACS. Compared to DMSO (control) treated cells, ZM447439 triggered accumulation of normal HME cells in $G_2$/M phase followed by tetraploidy and then cell death (FIG. 5F), whereas the same treatment had little effect on geminin overexpressing cells (FIG. 5F).

Figure 9C:
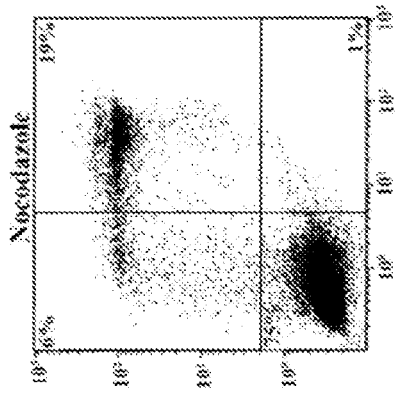
FIGS. 9A-9H are graphs showing the extent to which geminin overexpression triggers nocodazole and taxol resistance in HME cells, including: graphs showing FACS analysis of uninduced (A, B and C) and induced (72 h, D, E and F) Gem9 cells that were exposed to DMSO, 5 µM of ZM446439 or 250 ng/ml of nocodazole for an additional 24 h, where the cells were harvested and after FITC-annexin-V binding and PI staining was analyzed by FACS, and where the lower left quadrants show viable cells (V$^-$/PI$^-$), the lower right quadrants show early apoptotic cells (V$^+$/PI$^-$), the upper left quadrants show necrotic cells (V$^-$/PI$^+$) and the upper right quadrants show non-viable late apoptotic/necrotic cells (V$^+$/PI$^+$) (FIGS. 9A-9F); and graphs showing the effect of nocodazole (FIG. 9G) or taxol (FIG. 9H) on HME or induced Gem9 cell cycle progression.
Figure 9B:
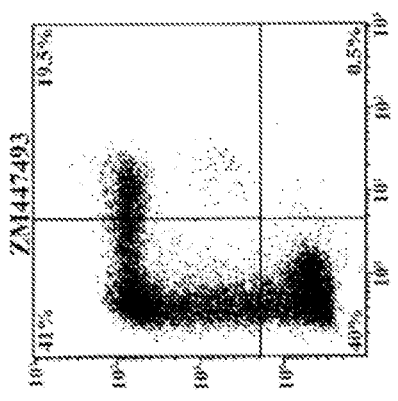
Figure 9A:
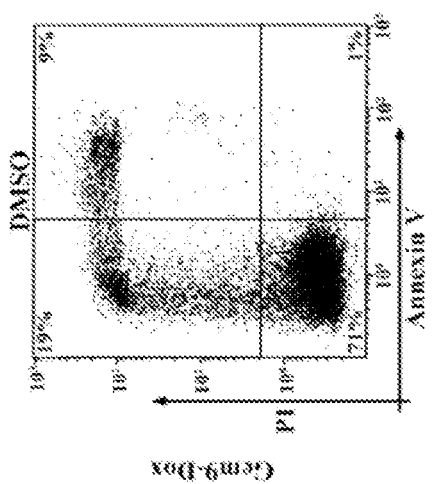

To measure the effect on ZM447439 on cell survival, aliquots from each culture were labeled with PI/annexin V and analyzed by FACS. In DMSO (control) treated Gem9–Dox cells, 71±4% were alive (PI$^-$/V$^-$), 19±5% were necrotic (PI$^+$/V$^-$) and 10±3% were apoptotic (PI$^-$/V$^+$+PI$^+$/V$^+$) cells (FIG. 9A), and ZM447439 treatment significantly increased cell death in the uninduced Gem9 cells. Indeed, in ZM447439 treated cells only 40±5% of the cells were PI$^-$/V$^-$, and 41±7% were PI$^+$/V$^-$ and 20±6% were PI$^-$/V$^+$+PI$^+$/V (FIG. 9B). In contrast, in DMSO treated Gem9+Dox, 79±3% were PI$^-$/V$^-$, 16±2% were PI$^+$/V$^-$ and 5±2% were PI$^-$/V$^+$+PI$^+$/V$^+$ cells, and ZM447439 treatment did not significantly increase cell death in these induced Gem9 cells. Indeed, in ZM447439 treated cells 66±4% of the cells were PI$^-$/V$^-$, 24±3% were PI$^+$/V$^-$ and 10±3% were PI$^-$/V$^+$+PI$^+$/V$^+$ (FIG. 9E). These data, again reinforce the fact that overexpression of Y phosphorylated/activated geminin protects HME cells against cell death induced by AurB inhibitors (i.e. induces AurB drug resistance).

To evaluate whether these effects were restricted to AurB inhibitors or could be seen with drugs that alter the integrity of the microtubules apparatus as well, HME and induced Gem9 cells were treated with DMSO (control), Nocodazole (a microtubules depolymerizing agent) or Taxol (a microtubules stabilizing agent) for another 24 h. FACS analysis showed that Nocodazole (FIG. 9G) or Taxol (FIG. 9H) treatment also triggered accumulation of normal HME cells in $G_2$/M phase, followed by tetraploidy and then cell death. However, both treatments also had modest effect on geminin overexpression cells (FIGS. 9C and 9D).

Figure 9F:
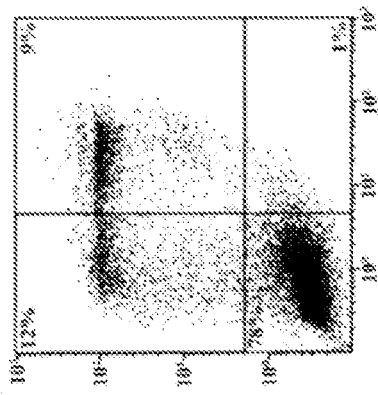
Figure 9E:
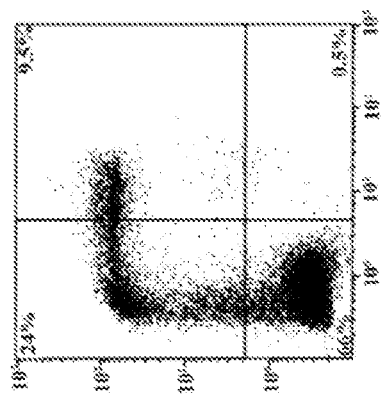
Figure 9D:
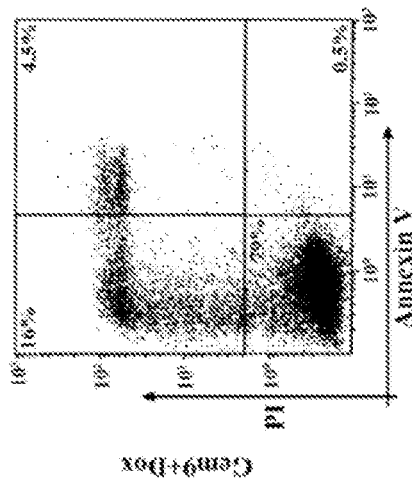
Figure 9G:
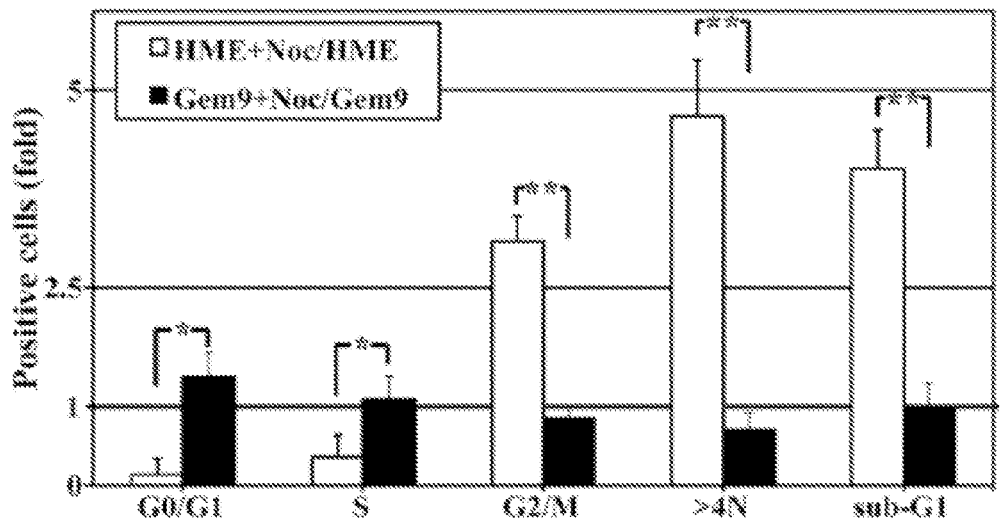
Figure 9H:
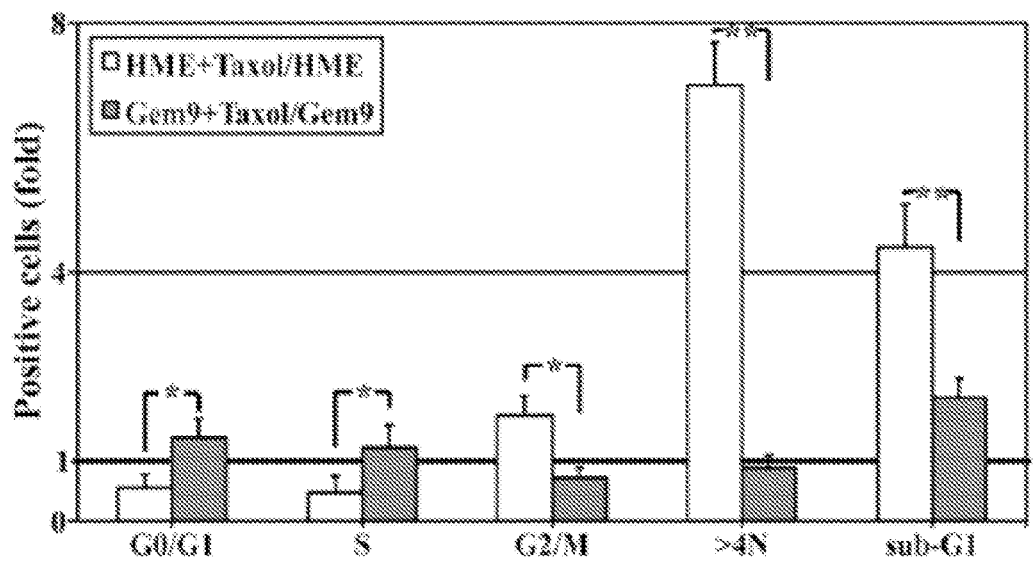

Moreover, FACS analysis of Nocodazole treated uninduced and induced Gem9 cells labeled with PI/annexin V showed that in Nocodazole treated HME cells, 75±5% of the cells were PI$^-$/V$^-$, 6±4% were PI$^+$/V$^-$ and 20±5% were PI$^-$/V$^+$+PI$^+$/V$^+$ (FIG. 9C), whereas in Nocodazole treated induced Gem9 cells 78±6% of the cells were PI$^-$/V$^-$, 12±3% were PI$^+$/V$^-$ and 10±2% were PI$^-$/V$^+$+PI$^+$/V$^+$ (FIG. 9F). Overall, these data indicated that overexpression of Y phosphorylated/activated geminin protects against cell death induced by AurB inhibition, or drugs that alter the fidelity of the microtubules apparatus.

Example 9

Geminin Overexpression Promotes Tumor Formation in SCID Mice

Figure 10:
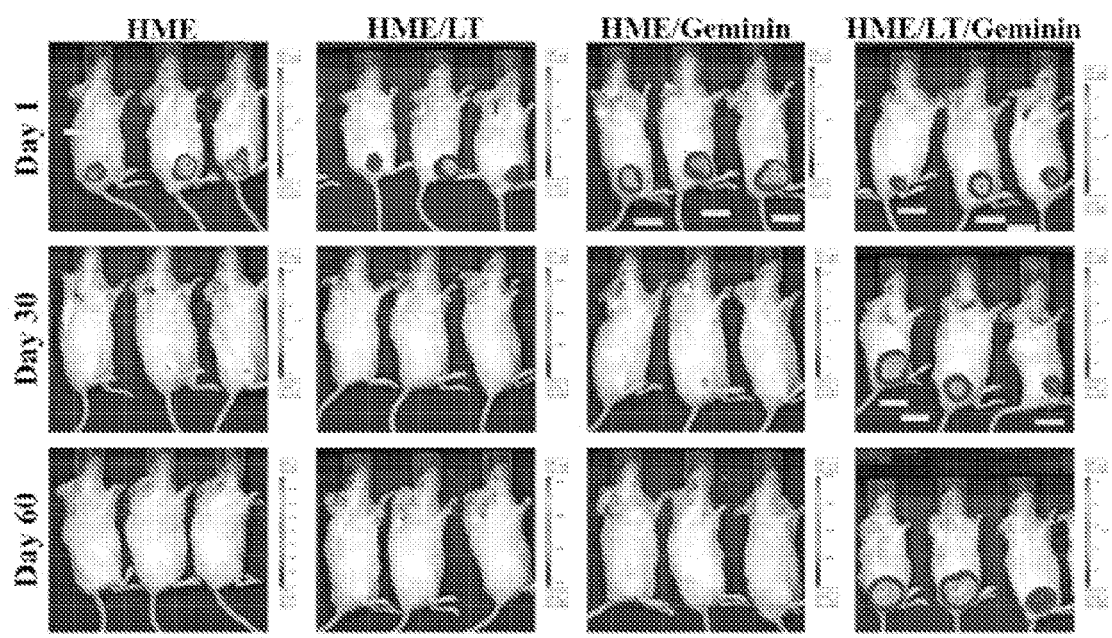
FIG. 10 includes in vivo images showing the effect of geminin on mouse subcutaneous tumor formation, including images of HME/TERT, HME/TERT/LT, HME/TERT/geminin or HME/TERT/LT/geminin cells on days 1, 30 and 60.

To determine the tumorigenic effect of geminin, in vivo, tumors were developed using geminin overexpressing HME cells in SCID mice. Five million luciferase-expressing immortalized HME (with TERT) cells that express SV40-Large T (LT), inducible geminin (i.e. Gem9) or both (i.e. Gem9/LT, see also [26]) were mixed 1:1 with matrigel and injected either subcutaneously or in the mammary fat pad of 10 (per cell line) SCID mice. All mice were maintained on Dox-supplemented drinking water during the duration of the experiments. Tumor development was monitored weekly by Xenogen® imaging and all cell lines were detected in mice on day 1 (FIG. 10, upper panels), but only Gem9/LT cells on day 30 and 60 (49 for mammary tumors, FIG. 10, lower panels).

Figure 6A:
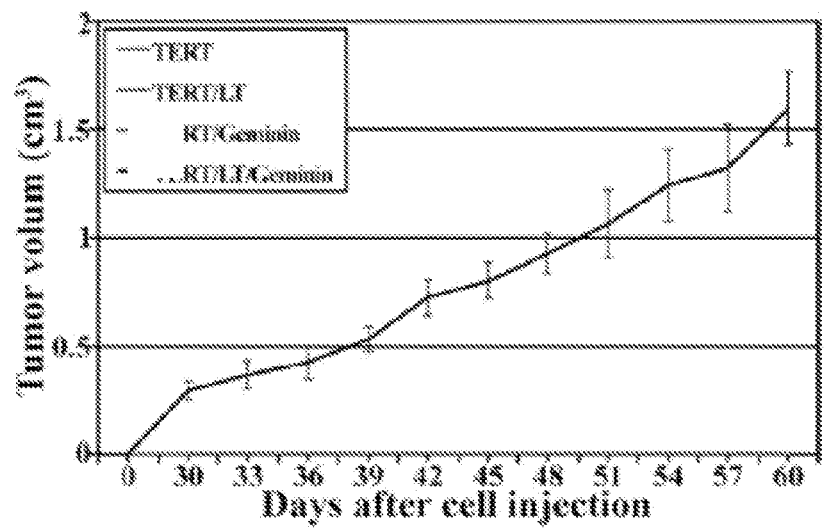
FIGS. 6A-6Q include images and graphs showing the generation and analysis of geminin overexpression-induced tumors; including: a graph showing the volume of subcutaneous tumors developed in mice (10 mice/group) injected with HME/TERT, HME/TERT/LT, HME/geminin (i.e. Gem9), or HME/TERT/LT/geminin (i.e. Gem9/LT) cells (FIG. 6A); images of hematoxylin and eosin (H&E) stained sections showing Gem9/LT tumors invading mouse muscle (M in FIG. 6B), bone (B in FIG. 6C), skin (S in FIG. 6D), nerve (N in FIG. 6E), and sweat glands (SG in FIG. 6F); images of H&E sections from Gem9/LT tumors showing different areas with high necrosis (FIGS. 6G-6H, N=necrotic cells, L=living cells); a graph showing the volume of mammary tumors developed in mice (10 mice/group) injected with HME/TERT, HME/TERT/LT, HME/geminin (i.e. Gem9), or HME/TERT/LT/geminin (i.e. Gem9/LT) cells (FIG. 6I); images showing the size (FIG. 6J) and the bloody appearance (FIG. 6K) of geminin overexpressing mammary tumors, where the arrows show blood vessels; images of sections from geminin overexpressing mammary tumors stained with H&E showing normal (dashed arrows) and large (solid arrows) size nuclei, where the sections also show increased blood vessels in the areas (FIGS. 6L-6N); a graph showing the density of blood vessels in areas containing tumor cells with normal size nuclei versus areas with tumor cells with abnormal (large) size nuclei (FIG. 6O); a graph showing the volume of mammary tumors developed in mice (10 mice/group) injected with parental or geminin silenced MDAMB231 cells, where the mice were kept on a Dox-supplemented water regimen to induce geminin shRNAs (FIG. 6P); and xenogene images at day 20 in subcutaneous tumors developed in mice injected with parental MDAMB231 (left) or MDAMB231/shGem1 (right) cells, where the mice were kept on a Dox-supplemented water to induce geminin shRNA expression (FIG. 6Q).
Figure 6B:
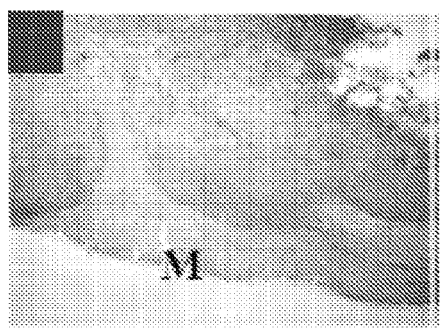
Figure 6C:
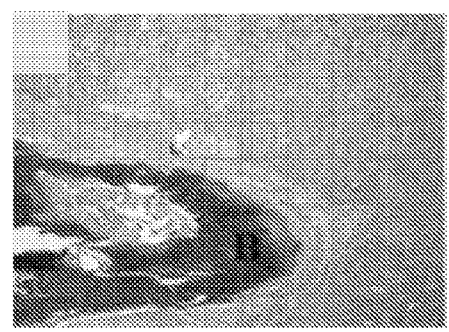
Figure 6D:
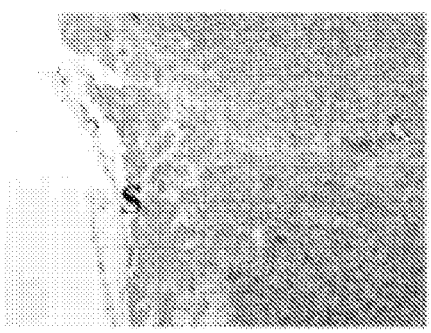
Figure 6E:
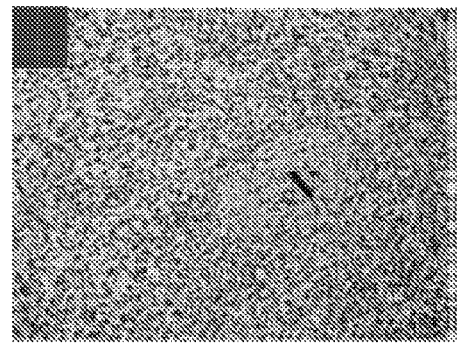
Figure 6F:
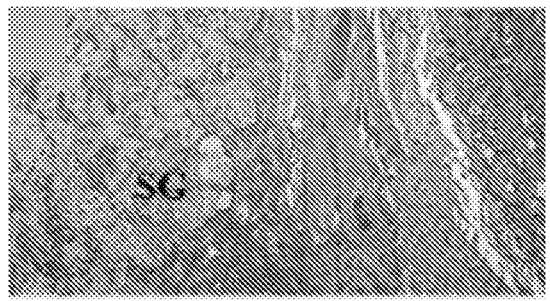
Figure 6G:
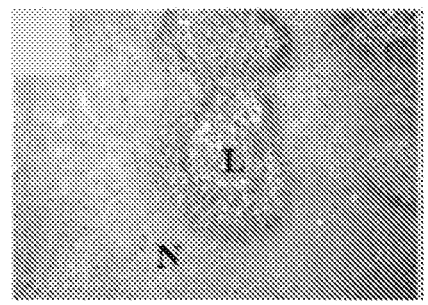
Figure 6H:
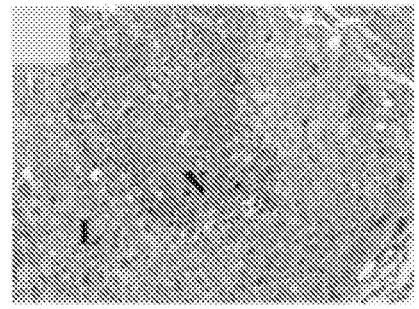

Geminin overexpressing cells formed subcutaneous tumors in 100% of the mice that were palpable at approximately day 30, grow rapidly thereafter to reach approximately 1.5 cm$^3$ (the allowed size) by 9 weeks (FIG. 6A). Dissected tumors were paraffin embedded, sectioned at 4 µm and stained with H&E. Geminin-induced tumors showed signs of aggressiveness. For example, the subcutaneous tumors invaded mouse muscle (see M in FIG. 6B) so much that tumor cells that were injected on the outside of the muscle were detected on the other side of the muscle surrounding the bone (see B in FIG. 6C). These tumors also invaded the skin (see S in FIG. 6D), the nerves (see N in FIG. 6E) and the sweat glands (see SW in FIG. 6F). Necrosis, the sign of aggressiveness and increased cancer cell proliferation, was a prominent component in these tumors as well (FIGS. 6G and 6H).

Figure 6I:
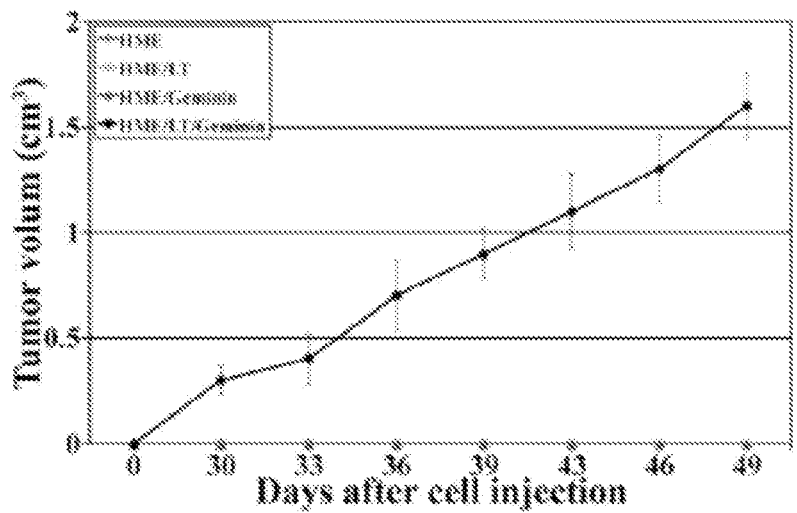
Figure 11:
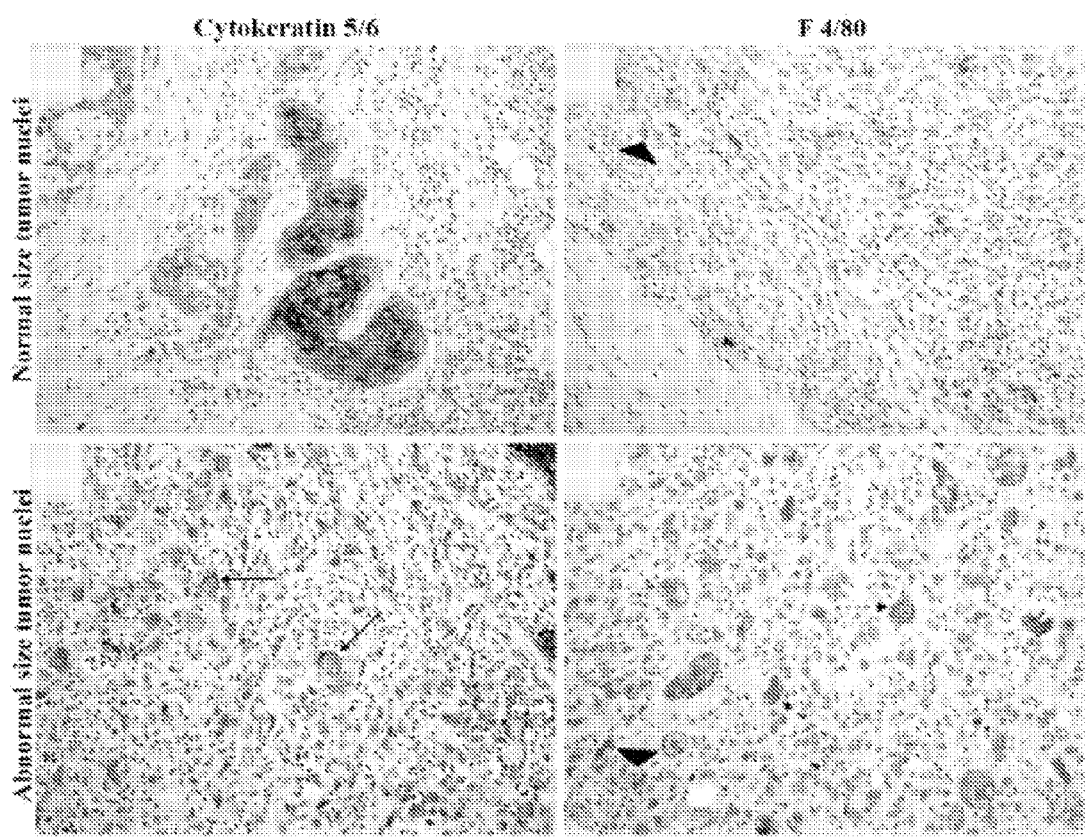
FIG. 11 includes images showing the immunohistochemical analysis of the origin of the cells with abnormally large size nuclei; including images showing sections of tumor cells with normal (upper left) or abnormal (lower left) size nuclei stained with anti-human cytokeratin (CK) 5/6 antibody; and images showing sections of tumor cells with normal (upper right) or abnormal (lower right) size nuclei stained with anti-mouse F 4/80 antibody.

Mammary tumors also formed in 100% of the mice and were more proliferative/aggressive and grew even more rapidly (reached approximately 1.5 cm$^3$ in 7 weeks only, FIG. 6I). Like subcutaneous tumors, mammary tumors also were invasive. More importantly, in both models, the presence of large areas of the tumors containing cells with abnormally large size nuclei (compare cells marked with solid arrows to cells marked with dashed arrows in FIG. 6L to 6N) was noticed. Again without wishing to be bound by any particular theory, it was believed that such cells could form from mouse macrophages infiltrating into the tumors and fuse as in Langerhans giant cells, typical of a tuberculoma [27] or they were aneuploid cells generated by overexpression of Y phosphorylated/activated geminin. To distinguish between the two possibilities, sections were immunohistochemically stained with an anti-human cytokeratin 5/6 (CK5/6) or an anti-mouse F4/80 (recognizes a protein expressed by activated murine macrophages). While, some tumor cells with normal and large size nuclei stained positive for CK5/6 (FIG. 11), none stained positive for F4/80-negative (FIG. 11). The F4/80 antibody, however, stained mouse macrophages infiltrated into the tumors in the same sections (FIG. 11).

Figure 6J:
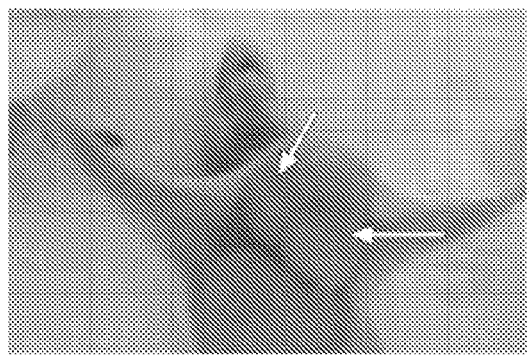
Figure 6K:
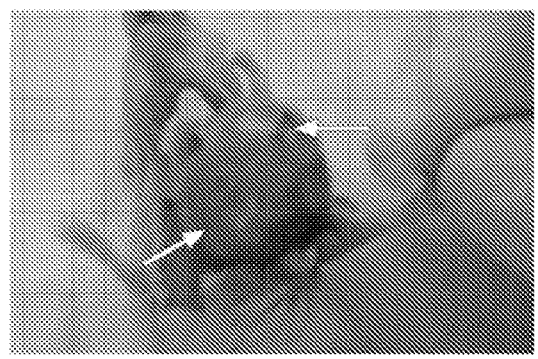
Figure 6L:
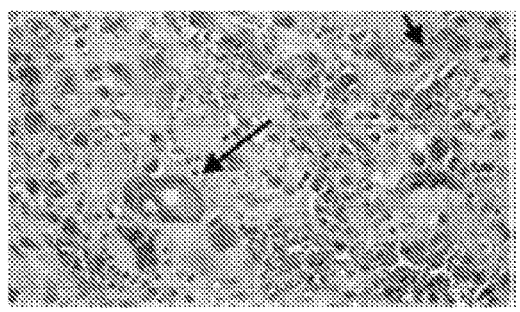
Figure 6M:
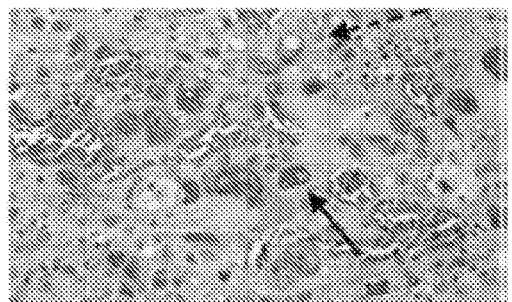
Figure 6N:
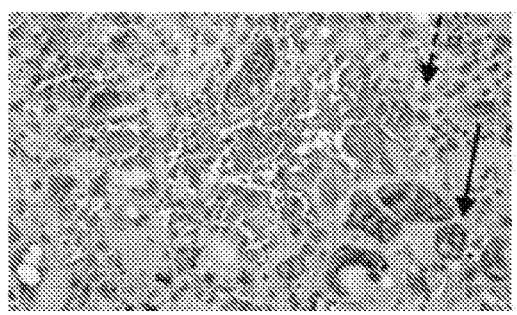
Figure 6O:
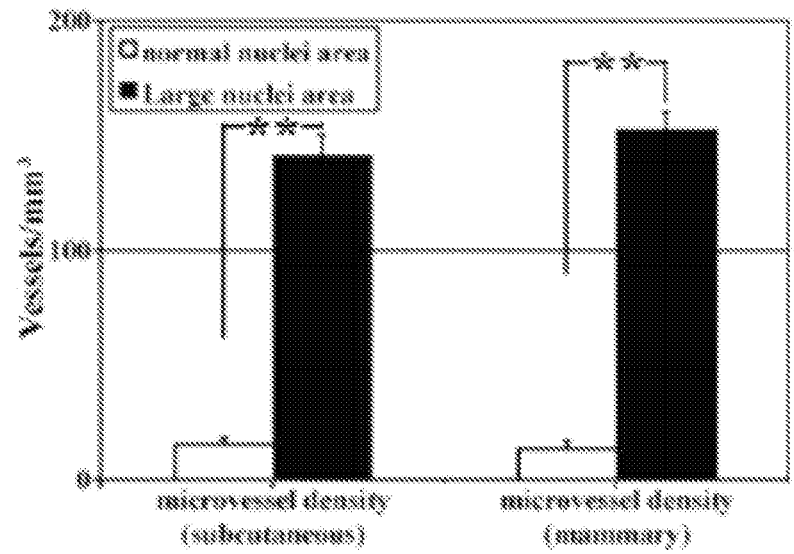

These geminin-induced tumors showed increased angiogenesis (see the bloody appearance denoted by arrows in FIGS. 6J and 6K). Analysis of H&E sections also confirmed increase numbers of blood vessels in these tumors, especially in areas containing cells with abnormally large nuclei (FIG. 6L to 6N). To determine the microvessel density, tumors sections were immunohistochemically stained with anti-mouse CD34 and microvessel density was determined as described previously [28]. In subcutaneous tumors 141±9 vs. 15±3 vessels/mm$^3$ (n=10, p<0.01) and in mammary tumors 152±8 versus 13±2 vessels/mm$^3$ (n=10, p<0.01) of microvessels were detected in areas with tumor cells with large size nuclei versus areas with tumor cells with normal size nuclei (FIG. 6O). These findings indicated that geminin overexpressing cells could induce host stromal cells to produce microvessels, and implied that aneuploid tumor cells attracted more blood vessels than non-aneuploid cells, or that aneuploid cells were formed in areas with abundant blood supply.

Example 10

Figure 7A:
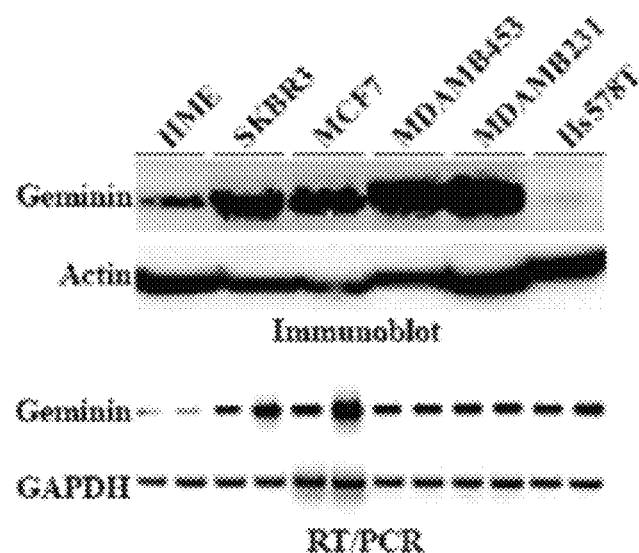
FIGS. 7A-7F include images and graphs showing geminin overexpression in aggressive primary breast cancers, including an image of a western blot and a gel showing the expression of geminin protein (upper) and mRNA (lower) in HME and several breast cancer cell lines (FIG. 7A); a graph showing comparisons of geminin-positive and negative samples in a test cohort using immunohistochemistry analysis (FIG. 7B); images of geminin expression in normal (FIG. 7C) and invasive tumor (FIG. 7D) samples from a confirmation cohort; a graph showing Geminin mRNA levels in breast cancer grade I (n=12) and grade III (n=78) samples (FIG. 7E); and a graph showing Geminin mRNA levels in metastasis occurring less than 5 years and greater than 5 years from diagnosis (FIG. 7F)

Analysis of Geminin Overexpression-Based Maintenance of Growth of Mammary Tumors in SCID Mice To determine whether geminin overexpression also maintained breast tumor growth in vivo, the very aggressive breast cancer cell line, MDAMB231 [29, 30] that endogenously overexpress geminin (see FIG. 7A) was used to generate clones that express 3 different conditional geminin shRNAs or a GFP shRNA (as control). All cell lines including parental MDAMB231 cells were made to express luciferase (hereafter: MDAMB231/Luc, MDAMB231/Luc/shGem1, /shGem2, /shGem3 and /shGFP).

Figure 6P:
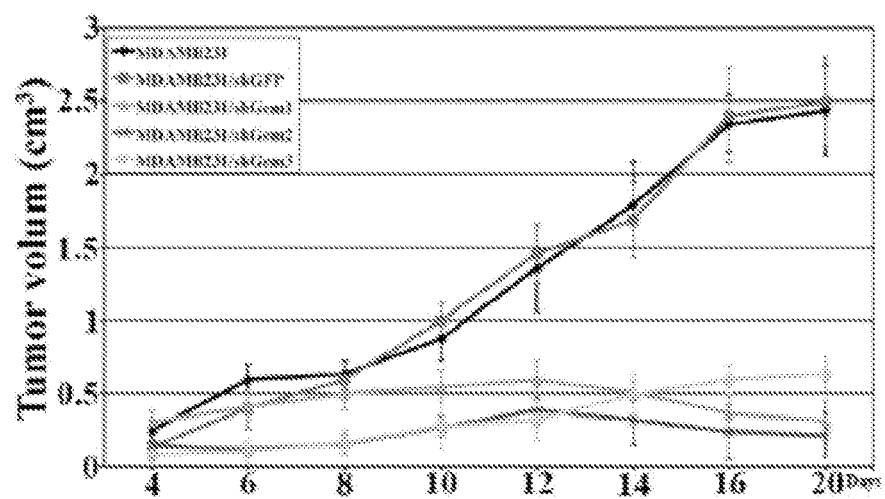
Figure 6Q:
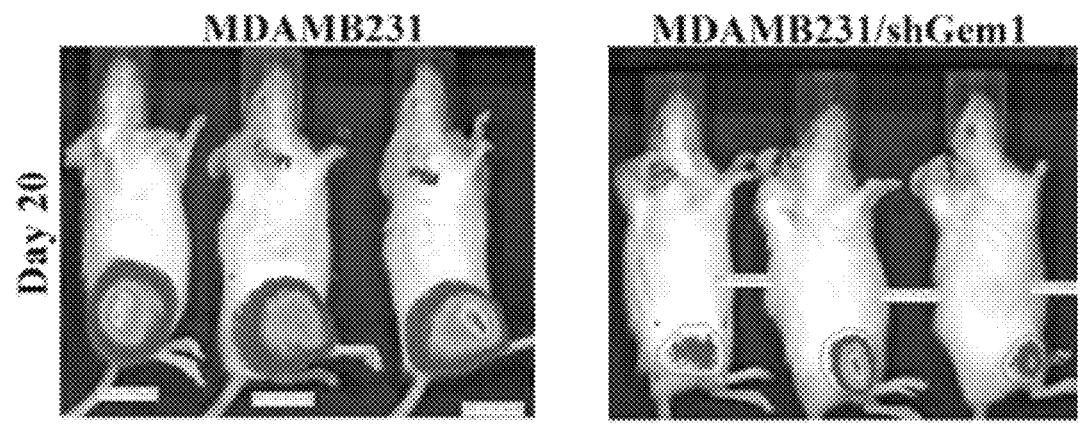

$5 \times 10^6$ cells (mixed 1:1 with matrigel) were injected into of each of these clones either subcutaneously or in the second mammary fat pad of 10 SCID mice/cell line. Mice were maintained on Dox-supplemented drinking water. The MDAMB231 cells were very aggressive cells, and tumors were palpable in all mice whether injected subcutaneously or in the mammary fat pad at day 4 and ranged in size between 0.15-0.25 cm$^3$ (FIG. 6P). By day 20, the size of the subcutaneous or mammary tumors developed by the MDAMB231 or MDAMB231/shGFP cells were so large that the mice were sacrificed (FIGS. 6P and 6Q, left). In contrast, geminin silencing suppressed the growth of the MDAMB231 cells injected in the mammary gland. Tumors either remained at approximately 0.2 cm$^3$ (/shGem2, FIG. 6P) throughout the experiment time (20 days), increased to approximately 0.5 cm$^3$ before regressing to approximately 0.2 cm$^3$ (/shGem1, FIG. 6P), or grew slightly to approximately 0.5 cm$^3$ (/shGem3, FIG. 6P) by day 20. Five extra mice injected with /shGem1 cells were followed for 80 days and tumors remained approximately 0.2 cm$^3$. Moreover, geminin silencing also suppressed the growth of MDAMB231 cells injected subcutaneously, in vivo (FIG. 6Q, right). Taken together, these data indicated that although previous reports suggested a putative tumor suppressor function for geminin [11,12,31], when overexpressed in HME cells, it was found that geminin acted as an oncogene that promoted formation and maintenance of aggressive and aneuploid breast tumors in vivo.

Example 11

Analysis of Geminin Overexpression in Aggressive Human Mammary Tumors

The expression of geminin mRNA protein was examined in breast tumor samples and cancer cell lines. It was found that geminin protein (FIG. 7A, upper) and mRNA (FIG. 7A, lower) were overexpressed in breast cancer cell lines. More importantly, a newly developed mouse monoclonal anti-geminin antibody was used [20] to analyze geminin expression in primary tumor samples by immunohistochemistry. For these analyses, two cohorts of paraffin embedded tissue microarrays (TMA) were used and constructed in quadruplicate with each containing one sample from a different region of the tissue/tumor at 4 μm. The first was a "test cohort," which was a commercial TMA (Biomax) that consisted of 66 normal or cancer adjacent, 180 cases of ductal carcinoma in situ (DCIS), 100 cases of invasive breast cancers and 165 cases of metastatic breast cancers. The second was a "confirmation cohort" consisted of 326 breast cancer tumors of different stages, in addition to several disease-free adult tissues (e.g., kidney, liver, placenta and spleen) and normal breast tissues that were acquired from the Hawaiian *Surveillance, Epidemiology and End Results* (SEER) collection.

Figure 7B:
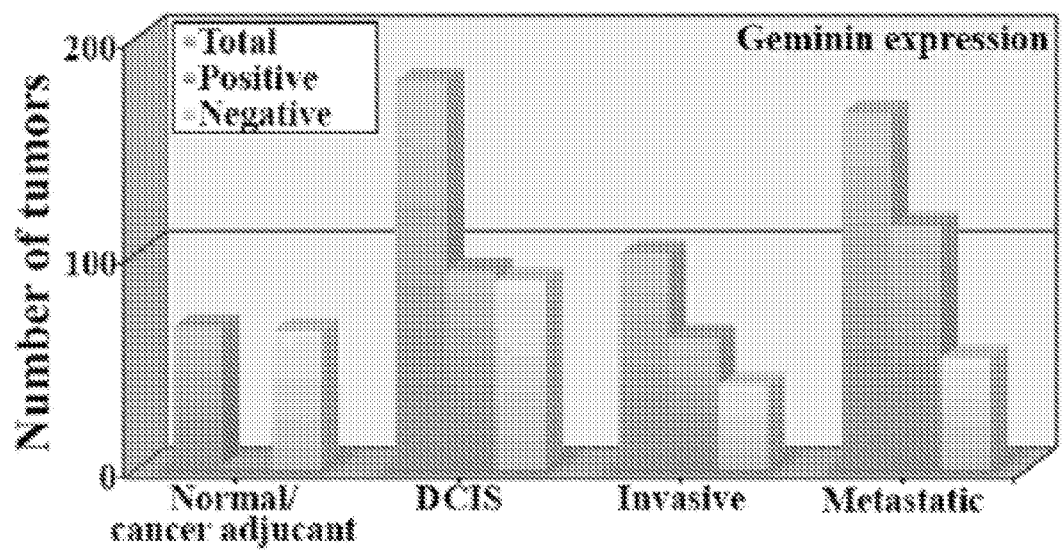
Figure 7C:
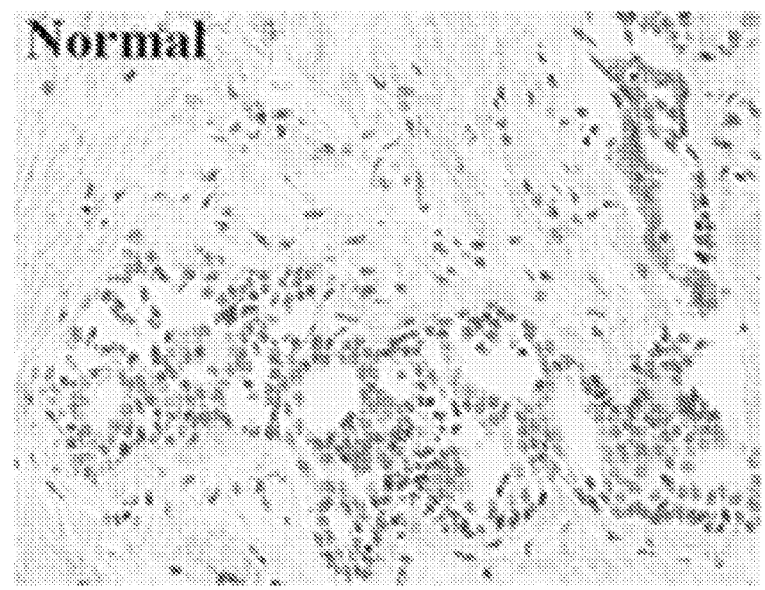
Figure 7D:
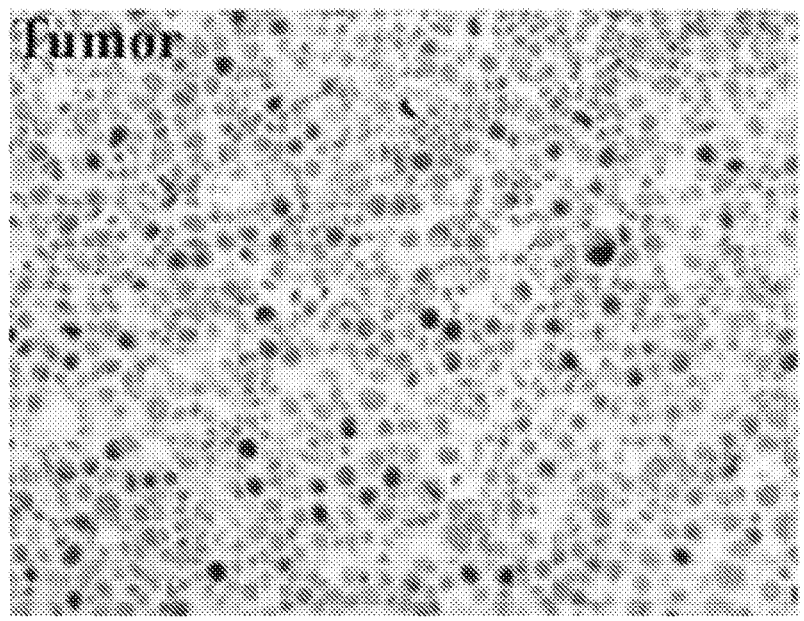

Following immunohistochemical staining, analysis and scoring was done blindly by two pathologists as follows; 0=no staining (<1% of the cells stained), 1+=weak (1-10% of the cells stained), 2+=medium (10-50% of the cells stained), 3+=strong (>50% of the cells stained). Staining scores less than or equal to 10% were considered negative tumors. In the test cohort, only 2 out of the 66 normal/cancer adjacent tissues were geminin-positive (3%, FIGS. 7B and 7C), whereas 92 from the 180 DCIS (51%, FIG. 7B), 61 out the 100 invasive (61%, FIGS. 7B and 7D) and 113 from the 165 metastatic tumors (68%, FIG. 7B) were geminin-positive. These data indicated that geminin expression increased further with disease progression. Furthermore, on the confirmation cohort, several disease-free tissues, e.g., liver, placenta, kidney, and spleen showed high level of geminin. Furthermore, while normal breast tissue was geminin-negative, 188 from the 326 (approximately 52%) of the breast tumor samples in this confirmation cohort stained positive for geminin. A set of 32 Her2$^+$ and 72 triple negative/basal like (TN/BL) tumors was also identified. In these tumors, 21 of the Her2$^+$ tumors (approximately 66%) and 41 of the TN/BL tumors (approximately 57%) were geminin-positive tumors.

Figure 7E:
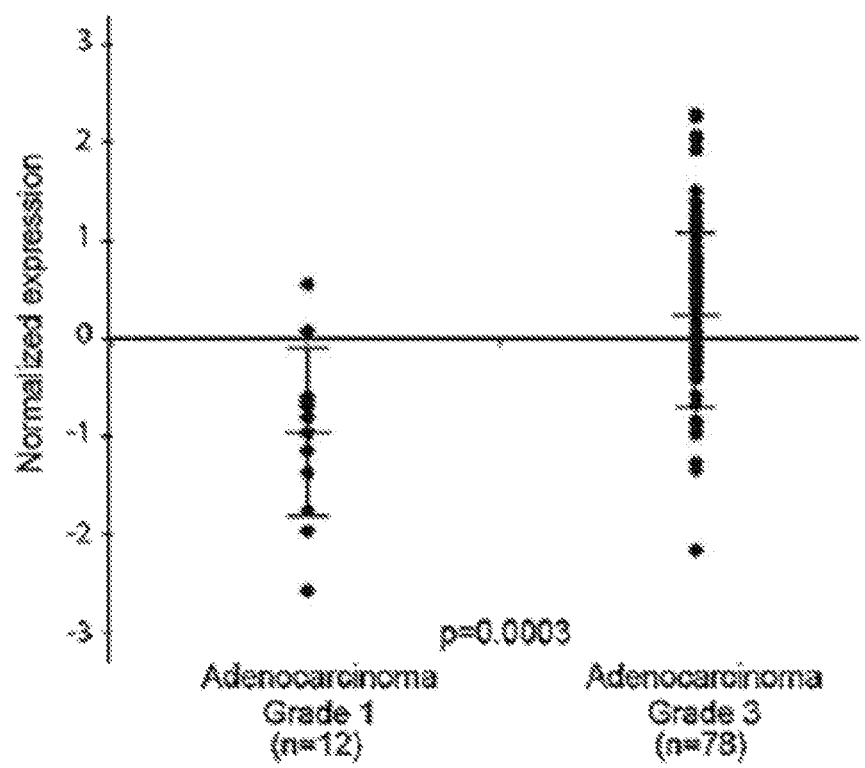
Figure 7F:
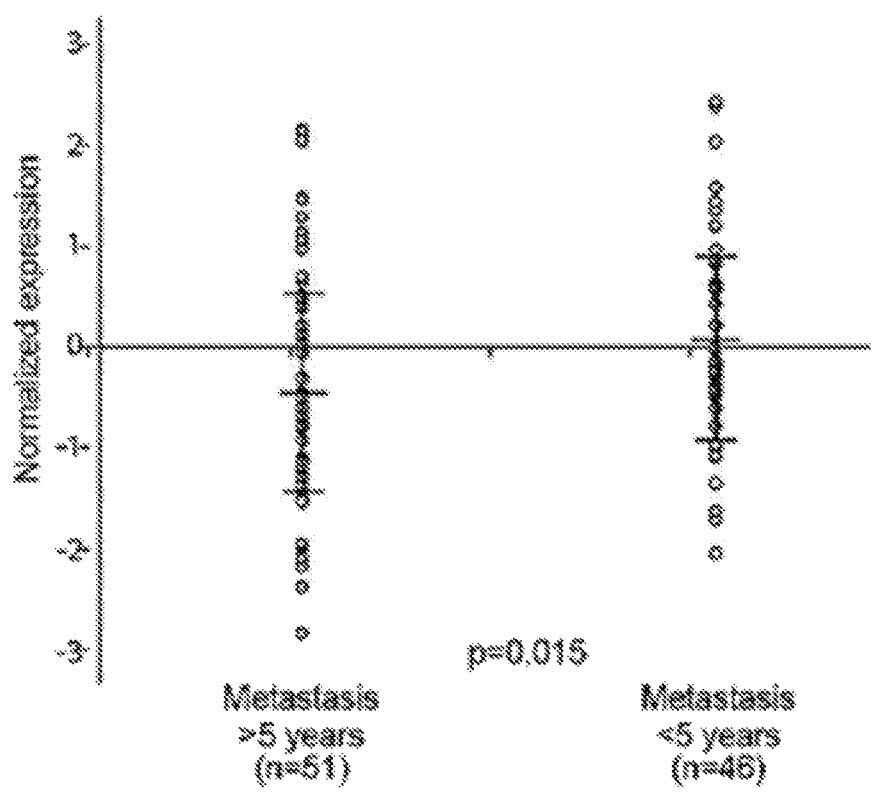

The expression of geminin mRNA was also analyzed in several publicly available gene expression microarray data sets [34-36]. The data revealed that geminin mRNA is expressed at significantly higher levels in high-grade [n=78] compared to low-grade [n=12] breast tumors (p=3×e$^{-4}$, FIG. 7D), as well as in tumors that metastasized greater than 5 years compared to greater than 5 years from diagnosis (p=1.5×e$^{-2}$, FIG. 7E). High geminin mRNA was also detected in estrogen- (p=2.929×e$^{-8}$) and progesterone- (p=2.764×e$^9$) receptor negative tumors, and in tumors carrying mutant BRCA1 (p=1.262×e$^{-3}$). In lymph node-positive (p=4.229×e$^{-5}$) and tumors showing increased angiogenesis (p=1.399×e$^{-3}$) geminin mRNA was also high.

Finally, to evaluate any genomic alteration in the geminin gene in breast cancers, a cohort of 150 breast patients DNA was analyzed with SNP analysis. No mutation, insertion, deletion or any other alterations was found in any of the tumors in this cohort. Overall the data showed that overexpression of wild type geminin induced cytokinesis failure and formation of aneuploid cells, in part, by suppressing AurB kinase. Geminin overexpression also prevented death of the resultant tetraploid/aneuploid cells, thus they can propagate and increase chances for the development of aggressive breast cancer. Indeed, geminin is overexpressed in the most aggressive types of breast cancers, e.g., Her2+ and TN/BL and is associated with adverse prognosis in invasive breast cancer. Thus, inhibiting geminin expression and/or activity could increase the efficacy of these drugs in a clinical setting.

Discussion of Examples 1-11.

In addition to binding to chromosomes in $G_2$/M/early $G_1$ cells [20], we here show that Y phosphorylated (simultaneously on all 3 tyrosine residues)/activated geminin is also localized to centrosomes, spindle, cleavage furrow and midbody during mitosis. Other proteins that show similar distribution during mitosis are mitotic checkpoint proteins, such as Polo kinase (Plk1) and the CPC (AurB, INCENP, survivin, and borealin [7]). Silencing of geminin arrested cytokinesis [20], while its overexpression triggered aneuploidy by inducing cytokinesis skipping. Interestingly, many proteins involved in proper cytokinesis are also required for accurate chromosome segregation [2], and interference with the expression or regulation of these components may lead to both chromosome missegregation and cytokinesis failure. In undertaking the forgoing studies, it was proposed that geminin was a novel chromosome segregation and proper cytokinesis regulator [20,22].

Aneuploidy is a hallmark of aggressive breast cancers [37]. Identification of molecules and mechanisms that lead to aneuploidy are beneficial in designing new therapies against breast cancer metastasis. Tetraploid cells (the precursors of aneuploid cells) can arise from diploid cells through cell fusion, endo-reduplication or cytokinesis failure. AurB plays important roles in both early and late stages of cytokinesis, by phosphorylating a wide variety of proteins essential for different steps of these processes. AurB inhibition even at very late stages of cytokinesis induces furrow regression [38], suggesting that AurB positively regulates abscission in mammalian cells [6,39]. It was thus possible that geminin overexpression generated aneuploid cells by suppressing AurB activity leading to abscission failure and furrow regression. The fact that activation of AurB requires binding to INCENP during mitosis and that geminin also binds to AurB during mitosis indicated that the two proteins perhaps compete for AurB binding. At normal level, INCENP perhaps binds AurB first and induces its autophsophorylation and activation, when geminin is overexpressed it binds AurB first and prevents its binding to INCENP and thus activation.

Intriguingly, AurB activity is also required for disassembly of the merotelic chromosome attachment occurring in DNA damaged cells [5,40]. In a recent study [22], it was shown that geminin overexpression induced TopoIIα-dependent chromosome breakages [22]. It was possible that geminin inactivation of AurB increased the chances for segregation of such damaged, lagging chromosomes, the likelihood of cytokinesis failure, and formation of tetraploid/aneuploid cells. In keeping with this, treating leukemia cells with the AurB kinase specific inhibitor; AZD1152 was shown recently to induce accumulation of cells with greater than 4N DNA content. However, these cells proceeded to die, unlike the greater than 4N cells generated after geminin overexpression (even in tumors) because geminin overexpression also induced expression and activation of several pro-survival factors in these cells.

Because multiple Bcl-2 anti-apoptotic members were found highly overexpressed in geminin overexpressing cells, it was though that geminin played an important role in maintaining survival of aneuploid, chemo-resistant cells and that overcoming geminin overexpression-induced breast cancers, in vivo would require co-antagonism of several Bcl-2 anti-apoptotic proteins. In this regard, it was possible to suggest that in geminin overexpressing tumors a model of co-antagonism has better therapeutic effect than inhibition of each protein individually [41].

Complete loss of the spindle checkpoint is lethal [42-44]. However, partial loss, such as in mice lacking only one copy of checkpoint proteins such as Mad2, BubR1 or CENP-E has no effect [42, 44-46]. Interestingly, reduction of expression of any of these genes triggered aneuploidy and increased rate of tumorigenesis [37]. It was also possible that as yet unidentified spindle checkpoint protein(s) are suppressed in geminin overexpressing aneuploid tumor cells.

The fact that HME cells overexpressing geminin form tumors in SCID mice suggest that unlike what was previously thought, when overexpressed, geminin behaves as a genuine oncogene that induces DNA damage and survival of DNA damaged cells leading to formation of aneuploid cells. Not surprisingly, geminin is overexpressed in approximately 50% of all breast tumors analyzed and to even higher degrees in two of the most aggressive subtypes, Her2+ and TN/BL tumors. In the mouse or in human, geminin overexpressing tumors also showed increased neo-angiogenesis suggesting that these tumors stimulate the surrounding mouse or human stroma to generate blood vessels. The foregoing data supported the view that geminin is a novel breast cancer therapeutic target. Geminin inhibition, in vivo, is also expected to increase the efficacy of existing drugs such as Taxol, doxorubicin and AurB inhibitors. Until specific geminin inhibitor is identified, it is believed that it is possible to treat these tumors with anti-angiogenic drugs.

Example 12 c-Abl Binding of Geminin in $G_2$/M/Early $G_1$ Phase in HME Cells

As described herein above, geminin tyrosine phosphorylation is required for its translocation to chromatin, centrosome, centromere, spindle and midbody in $G_2$/M/early $G_1$ phases in HME cells. Human geminin contains three tyrosine residues at position 98, 111 and 150. Kinases often bind their targets. Thus, to identify geminin tyrosine kinase(s), it was reasoned that it might be possible to co-immunoprecipitate kinases using geminin antibody. HME cells synchronized in S- or $G_2$/M-phase of the cell cycle were sonicated (to isolate all cellular proteins, even those on the chromatin), immunoprecipitated using monoclonal anti-geminin antibody, and immunoprecipitated bands were cut out and micro-sequenced. Geminin antibody co-immunoprecipitated Cdt1 from S phase extracts and c-Abl from $G_2$/M-extracts.

Figure 12A:
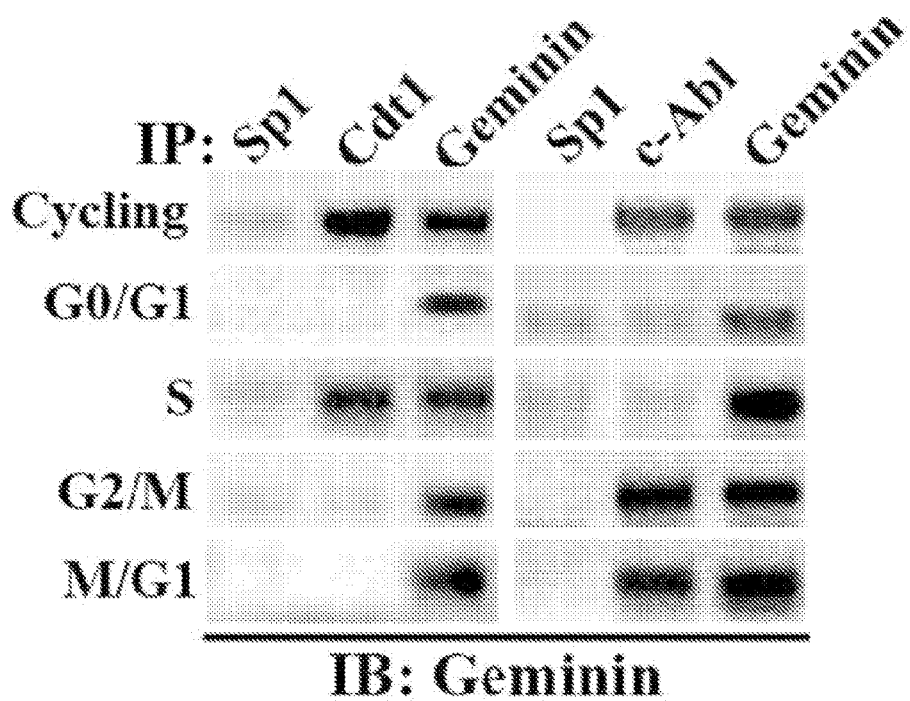
FIGS. 12A-12F showing graphs and images showing the extent to which c-Abl binds and phosphorylates geminin in G2/M cells and the effect of its silencing on inactivation of geminin induced aneuploidy, including: images of western blots where HME cells synchronized in G0/G1, S, G2/M or M/G1 were immunoprecipitated with antibodies against the indicated proteins and immunoprecipitated proteins were immunoblotted with anti-geminin antibody (FIG. 12A); images showing the results of an in vitro kinase assay of geminin by c-Abl, where S or G2/M phase HME cells extracts were immunoprecipitated with anti-c-Abl antibody (upper), and where immunoprecipitated proteins on beads were incubated with radioactive ATP and the indicated GST tagged proteins.

To confirm these data, cycling or $G_0$/$G_1$, S, $G_2$/M and M/$G_1$ synchronized HME cells were sonicated and proteins were immunoprecipitated using anti-Cdt1, -c-Abl, -geminin and -Sp1 (as negative control). Cdt1 antibody co-immunoprecipitated geminin from S-extract only (FIG. 12A, left), whereas with c-Abl antibody, geminin was co-immunoprecipitated from -$G_2$/M and -M/$G_1$ extracts (FIG. 12A, right). This confirmed that c-Abl and geminin form a complex in $G_2$/M/early $G_1$ phases in HME cells.

Example 13 c-Abl Phosphorylation of Geminin in $G_2$/M Phase in HME Cells

Figure 12B:
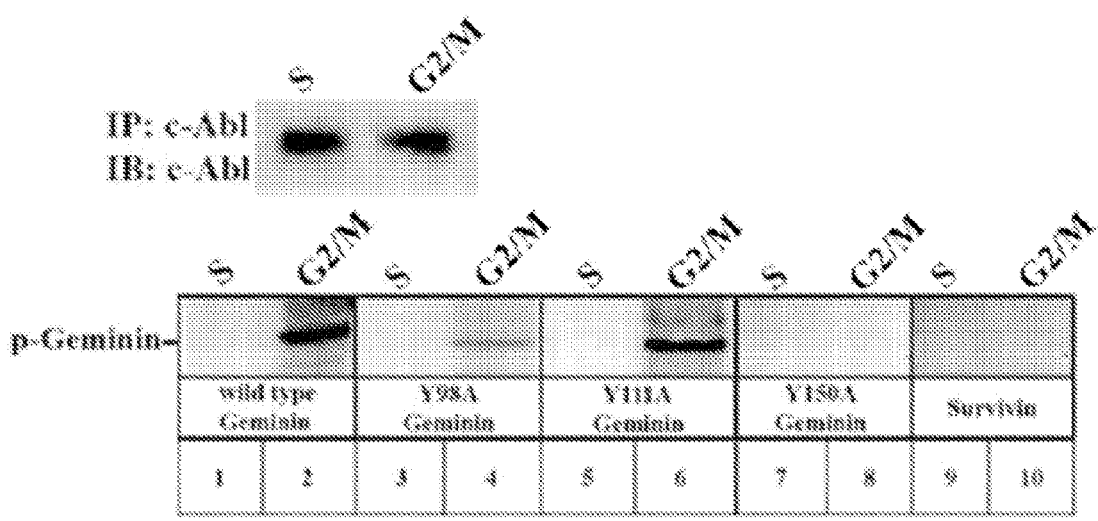

Whether c-Abl phosphorylates geminin was next studied using an in vitro kinase assay. In brief, c-Abl immunoprecipitated from S- or $G_2$/M-phase synchronized HME cells (note equal level of c-Abl immunoprecipitated with this antibody from each phase, FIG. 12B, upper panel) were used. Following immunoprecipitation, equal volume of beads-bound c-Abl was incubated with GST-wild type (wt)-geminin, -GemY98A, -GemY111A or -GemY150A and radioactive ATP. c-Abl isolated from either phase did not phosphorylate GST-survivin (negative control, lane 9 and 10 in FIG. 12B, lower). c-Abl isolated from $G_2$/M- and not S-phase phosphorylated GST-wt-geminin (lanes 1 and 2 in FIG. 12B, lower), GST-GemY98A (lanes 3 and 4 in FIG. 12B, lower) and -GemY111A (lanes 5 and 6 in FIG. 12B, lower), and not -GemY150A (lanes 7 and 8 in FIG. 12B, lower). This indicated that only mitotic c-Abl phosphorylates geminin on Y150.

Figure 12C:
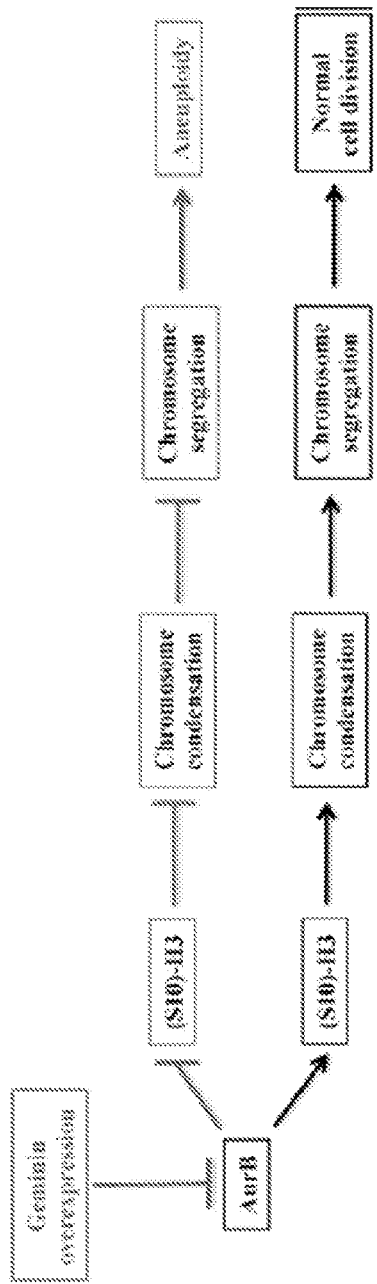
Figure 12D:
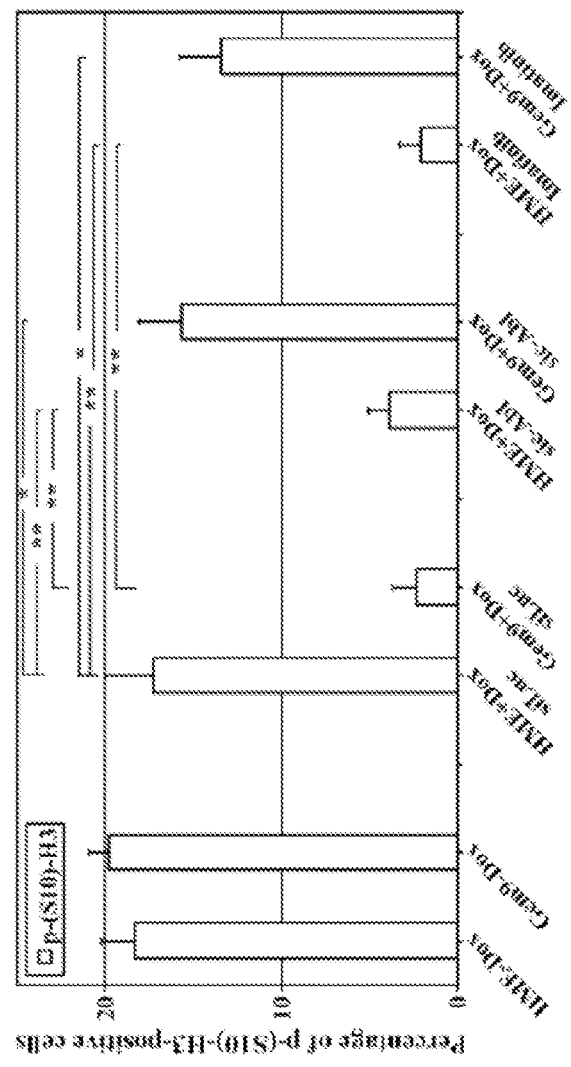

Example 14 c-Abl Silencing or Inactivation Restores Histone H3 (S10) Phosphorylation, Chromosome Condensation and Suppresses Aneuploidy in Geminin Overexpressing HME Cells Diminution of (S10)-H3 phosphorylation leads to chromosome condensation failure, lack of chromosome segregation and induction of aneuploidy (Giet et al., 2001). As shown in experiments described herein above, overexpression of wild type and not single Y-to-A mutant geminin suppresses (S10)-H3 phosphorylation, thus promoting cytokinesis skipping and aneuploidy in HME cells (FIG. 12C). c-Abl was silenced (for 72 h) or inactivated using 10 µM imatinib (for 24 h) in normal or geminin-overexpressing (inducible Gem9) HME cells. Aliquots of each culture were then fixed, labeled with FITC-anti-p-H3-(S10) specific antibody and analyzed by FACS. In the absence of doxycycline (Dox), parental and Gem9 HME cells showed normal levels of p-(S10)-H3-positive cells (approximately 20%, FIG. 12D). Geminin overexpression (i.e. in induced Gem9 cells) significantly reduced that (approximately 2%, FIG. 12D). c-Abl silencing or inactivation restored the level of p-(S10)-H3-positive cells to near normal level (approximately 15% and approximately 13%, respectively, FIG. 12D). The same treatments, reduced the percentage of p(S10)-H3-positive cells in parental HME cells (FIG. 12D).

Figure 12E:
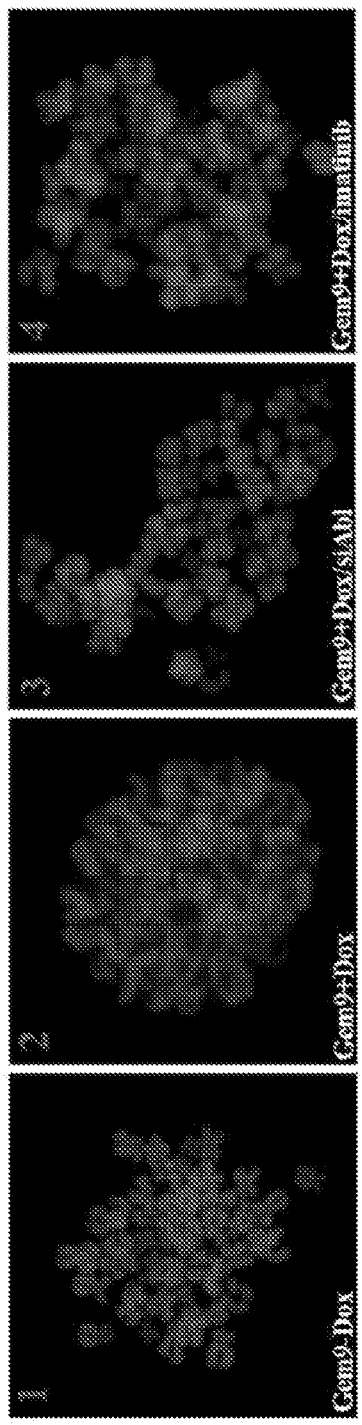

To study the effect of reducing c-Abl expression or activity on chromosome condensation in geminin overexpressing cells, Gem9 cells were grown in the presence or absence of Dox for 7 days, then exposed to 10 µM of the microtubules depolymerizing agent, colcemid (Ruchaud et al., 2007) for 1 h, then processed for metaphase chromosome spread. Colcemid treatment induced condensation of uninduced Gem9 cells chromosomes (FIG. 12E/1), but failed to condense the chromosomes in geminin overexpressing cells (FIG. 12E/2). c-Abl silencing (during the last 72 h) or inactivation with 10 µM imatinib (during the last 24 h) in induced Gem9 cells restored chromosome condensation (FIGS. 12E/3 and 12E/4, respectively).

Figure 12F:
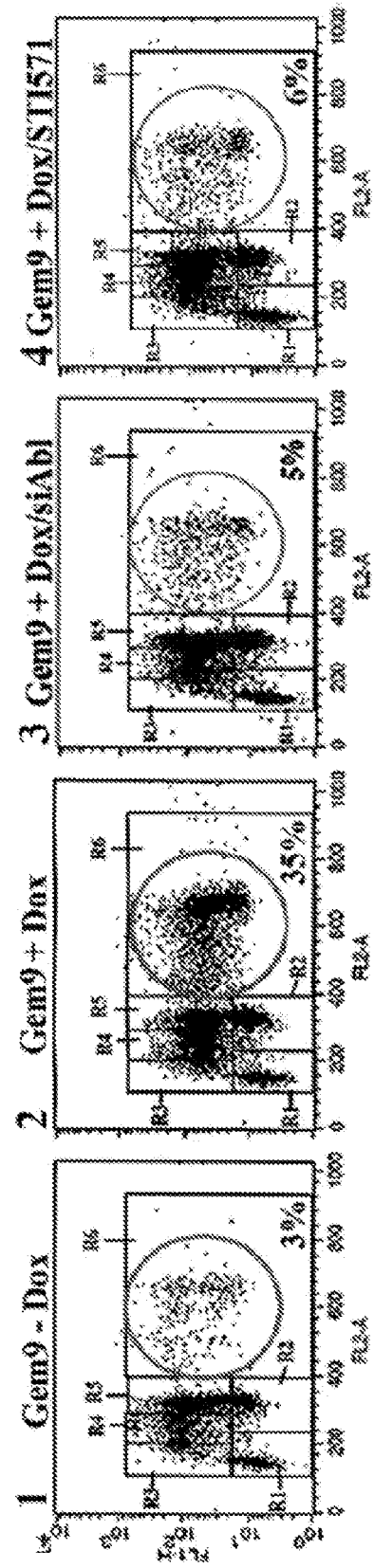

Finally, to study whether inhibiting c-Abl expression or activity in geminin overexpressing cells can prevent aneuploidy, Gem9 cells were grown in the presence or absence of Dox for 72 h. BrdU (20 µM) was added to all cultures during the last 24 h and cultures were collected, labeled with PI and FITC-anti-BrdU antibody and analyzed by FACS. While less than 3% of uninduced cells had greater than 4N DNA content (tetraploid/aneuploid cells, see circle in FIG. 12F/1), approximately 35% of induced Gem9 showed greater than 4N DNA content (see circle in FIG. 12F/2). c-Abl silencing (72 h) or inactivation with 10 µM imatinib (during the last 24 h) in induced Gem9 cells, decreased the percentage of tetraploid/aneuploid cells to approximately 5 and approximately 6%, respectively (FIGS. 12F/3 and 12F/4). These data showed that phosphorylation of geminin Y150 by c-Abl was an important event for overexpressed geminin ability to inhibit (S10)-H3 phosphorylation, chromosome condensation and to induce tetraploidy/aneuploidy in HME cells.

Example 15

Figure 13A:
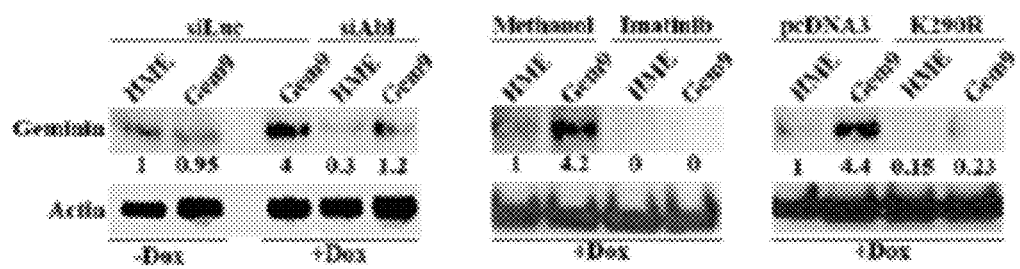
FIGS. 13A-13G are graphs and images showing the stabilization of endogenous and exogenous geminin by c-Abl, including: images of western blots showing geminin levels in cells that were c-Abl silenced (72 h, left), inactivated with 10 µM imatinib (24 h, middle) or expressing a dominant negative c-Abl (K290R, 48 h, right (FIG. 13A); images of western blots showing geminin level in induced Gem9 (72 h), MCF7 or MDAMB231 cells silenced from c-Abl or treated with Gleevec® (FIG. 13B); images of a western blot showing geminin level in HME or induced Gem9 (72 h) cells treated with 10 µM Gleevec® in the presence or absence of 10 µM MG-132 (FIG. 13C); a graph showing the percentage of HME or Gem9 cells transfected with control or si-c-Abl (for 72 hr) or treated with 10 µM of imatinib (during the last 24 h) in the presence or absence of doxycycline (72 h) (FIG. 13D); images showing the effect of c-Abl silencing with sic-Abl (96 h) or inhibition with imatinib (48 h) on the survival of uninduced or induced Gem9 cells as analyzed under light microscope (FIG. 13E); images showing the effect of c-Abl silencing with sic-Abl (96 h) or inhibition with imatinib (48 h) on the survival of uninduced or induced Gem9 cells as analyzed using TUNEL assay (FIG. 13F); and a graph showing the results of an experiment where HME or Gem9 cells were either transfected with control or si-c-Abl (for 72 hr) or treated with 10 µM of imatinib (during the last 48 h) in the presence or absence of doxycycline (96 h), and where cells from all cultures were subsequently labeled with TUNEL and positive cells were counted (FIG. 13G)
Figure 13B:
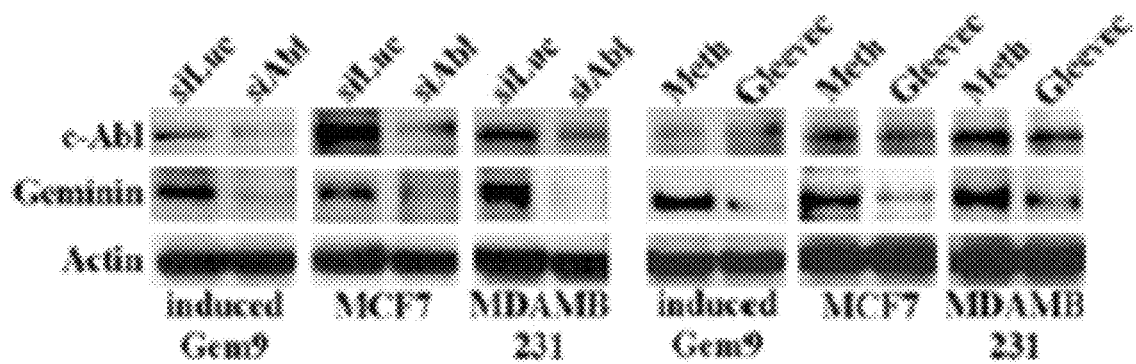
Figure 13C:
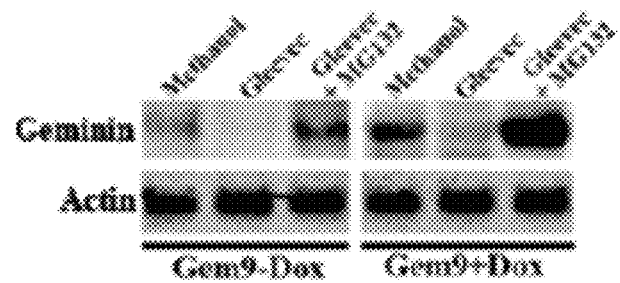

Analysis of c-Abl Silencing or Inactivation on Geminin Protein Degradation and Apoptosis in Geminin Overexpressing Cells To study the consequence of silencing or inactivating c-Abl on geminin overexpressing cells, experiments were first undertaken to analyze what happens to geminin protein following c-Abl silencing or inactivation. HME or Gem9 cells were incubated with 2 µg/ml Dox for 72 h and c-Abl was either silenced during this time, or inactivated with 10 µM imatinib during the last 24 h. Another Dox treated set of cells were transfected with c-Abl dominant negative construct (i.e. K209R, see Srinivasan and Plattner, 2006) during the last 48 h. Sonicated extracts were then prepared from all cultures and geminin level was measured using western blot analysis. Significant reduction in endogenous (in HME) as well as overexpressed (in induced Gem9) geminin protein level following c-Abl silencing (FIG. 13A, left) or inactivation by imatinib treatment (FIG. 13A, middle) or after overexpression of the dominant negative c-Abl ("K209R", FIG. 13A, right) was measured. Similar effects were also observed in cells endogenously overexpressing geminin. Indeed, c-Abl silencing or inactivation (with 10 µM imatinib) in MCF7 (estrogen receptor, ER+) and MDAMB231 (ER−) breast cancer cell lines also significantly reduced the level of geminin protein (FIG. 13B). Moreover, when uninduced or induced Gem9 (72 h) cells were exposed to 10 µM imatinib in the presence of 10 µM of the proteasome inhibitor MG132 during the last 24 h, an increase instead of a decrease in the level of geminin protein in HME as well as induced Gem9 cells was measured (FIG. 13C).

Figure 13D:
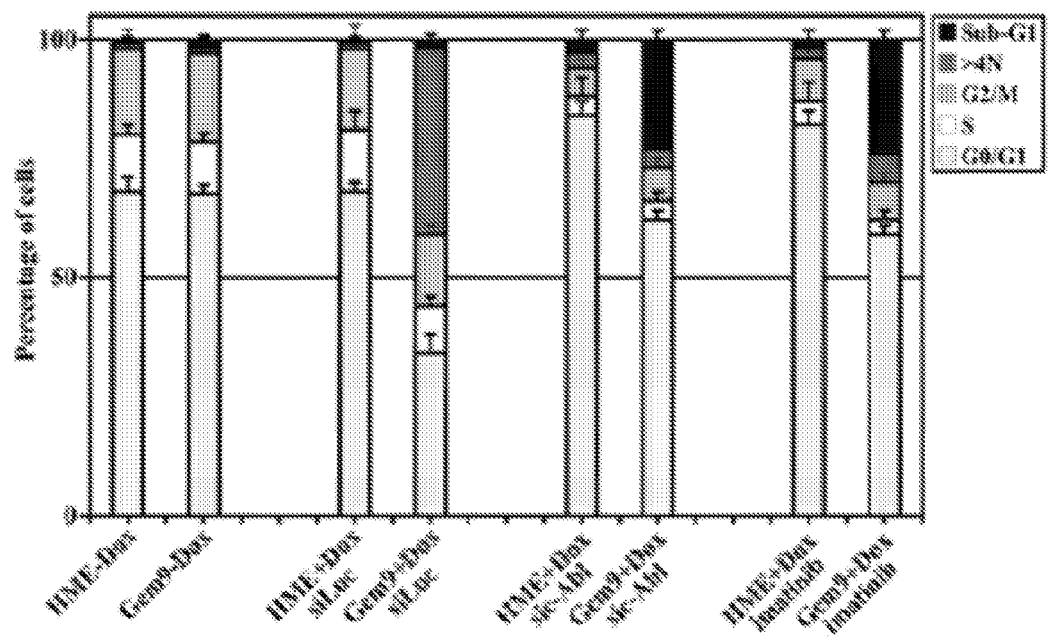
Figure 13E:
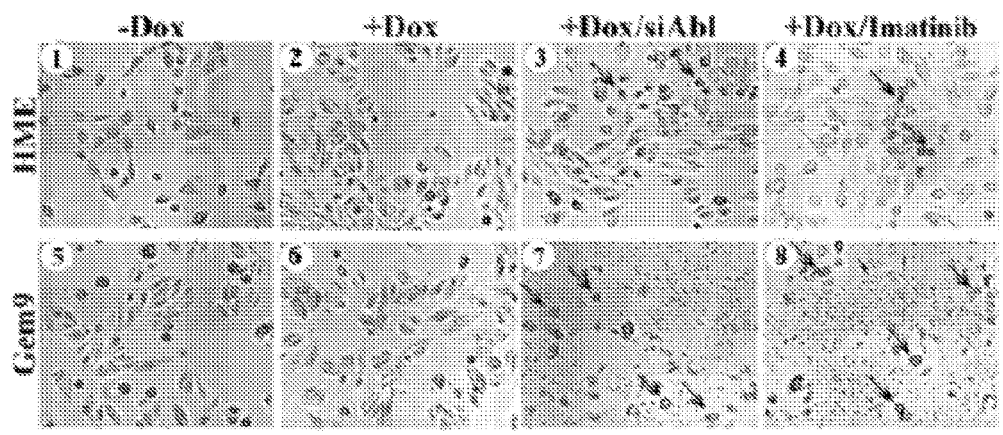
Figure 13F:
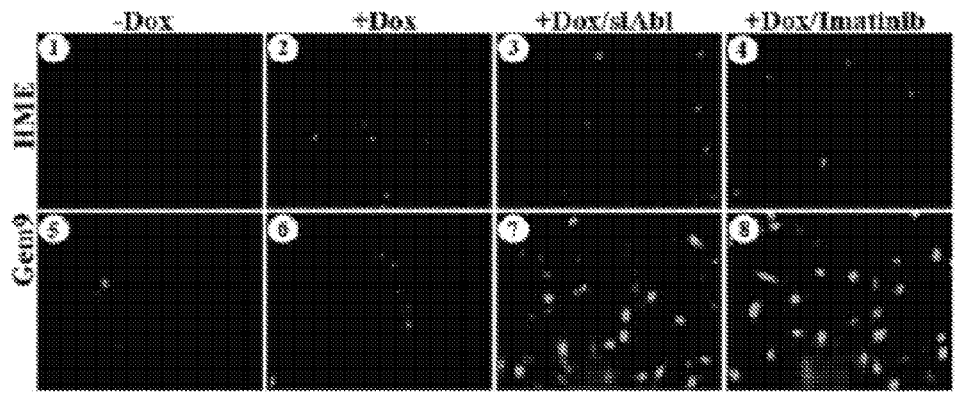
Figure 13:
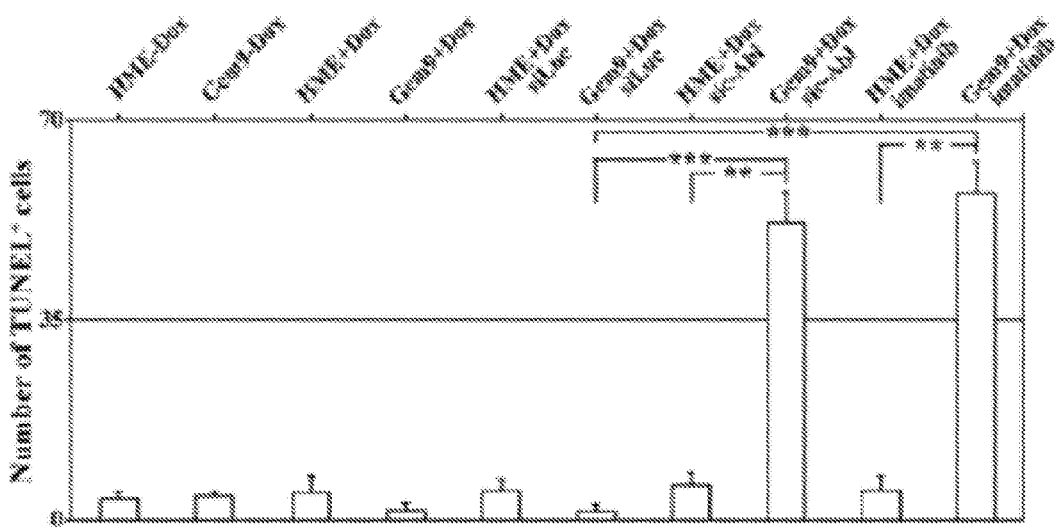

To study the biological consequence of the foregoing findings, HME and Gem9 cells were grown in the absence or presence of Dox (72 h) and c-Abl was silenced (72 h) or inactivated (with 10 µM imatinib, during the last 24 h) in these cells. Cells were then collected, labeled with PI and analyzed by FACS. c-Abl silencing or inactivation induced $G_1$-arrest in HME cells (FIG. 13D). In contrast, the same treatments induced significant increase in sub-G1 and reduced the level of >4N cells in induced Gem9 cells (FIG. 13D). To confirm that further, c-Abl was silenced (96 h) or inactivated (with 10 µM imatinib during the last 48 hrs) in HME or induced Gem9 (96 h), and the number of dying cells was analyzed under light microscope or by counting TUNEL+ cells in 10 high magnification fields of each culture. Low number of dying cells was detected in parental or Gem9 cells in the absence of Dox (FIGS. 13E/1 and 13E/5, 13F/1 and 13F/5 and 13G) or in HME cells in the presence of Dox (FIGS. 13E/2 and 13E/6, 13F/2 and 13F/6 and 13G). Low level of dying cells was also observed in parental HME cells transfected with c-Abl siRNA (FIGS. 13E/3, 13F/3 and 13G) or treated with 10 μM imatinib (FIGS. 13E/4, 13F/4 and 13G). In contrast, high number of dying cells was detected in c-Abl silenced (FIGS. 13E/7, 13F/7 and 13G) or inactivated (FIGS. 13E/8, 13F/8 and 13G) induced Gem9 cells. It was thought that degradation of geminin following c-Abl silencing or inactivation promoted cell death in geminin overexpressing and not normal cells, at least in part, because cells became addicted to high levels of geminin. These data showed that geminin binding to and/or phosphorylation by c-Abl protected geminin protein from proteasome degradation, and indicating that in normal cells, inhibiting c-Abl expression or activity was not crucial for HME cell survival but promoted cell death in geminin overexpressing cells, most likely because cells became addicted to high levels of geminin.

Example 16

Figure 14A:
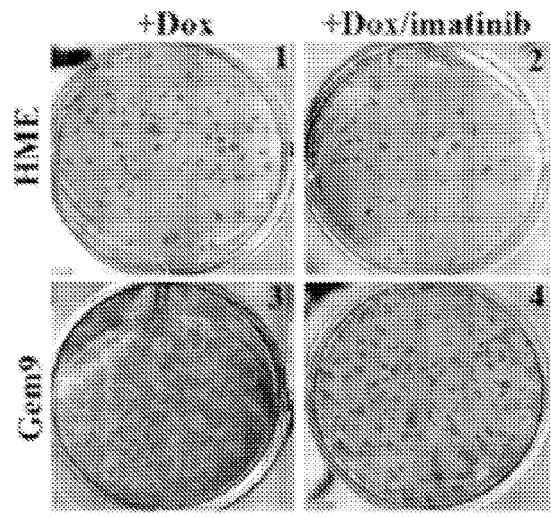
FIGS. 14A-14F include images and graphs showing extent to which geminin overexpression transforms HME cells and is overexpressed with c-Abl in aggressive breast tumors, including images of a soft agar colony formation assay using HME cells in presence of Dox (1) or Dox and 10 μM imatinib (2) or Gem9 in the presence of Dox (3) or Dox and 10 μM imatinib (4) cells (FIG. 14A); a graph showing the quantitative analysis of the soft agar experiment shown in FIG. 14A (FIG. 14B); an image of a western blot showing geminin and c-Abl levels in mammary cancer cell lines (FIG. 14C); a graph showing geminin and c-Abl mRNAs levels in mammary cell lines (left) or breast tumors samples (right) (FIG. 14D); graphs showing the expression of geminin and c-Abl as detected using immunohistochemistery on normal/cancer adjacent, DCIS, invasive, and metastatic breast tumors (FIG. 14E); and images showing the immunohistochemical staining of breast tumor sections with anti-geminin (1 and 3) or anti-c-Abl (2 and 4) antibodies (FIG. 14F)

Analysis of c-Abl Silencing or Inactivation on Geminin Overexpression Ability to Transform HME Cells HME and Gem9 cells were grown in the presence or absence of Dox (72 h) before they were layered in soft agar for another 14 days, in the presence or absence of Dox and imatinib (10 μM). Low number of small size colonies was observed in cultures of HME and Gem9 grown in the absence of Dox (FIGS. 14A/1 and 14B) or HME culture grown in the presence of Dox (FIGS. 14A/1 and 14B). In contrast, large numbers of large size colonies were observed in induced Gem9 cultures (FIGS. 14A/3 and 14B). Imatinib treatment reduced slightly the number of colonies in HME cultures grown in the presence of Dox (FIGS. 14A/2 and 14B), whereas the same treatment dramatically reduced the number and the size of the colonies of induced Gem9 cells (FIGS. 14A/4 and 14B). These data showed that geminin overexpression transformed HME cells in a c-Abl-dependent manner.

Example 17

Figure 14B:
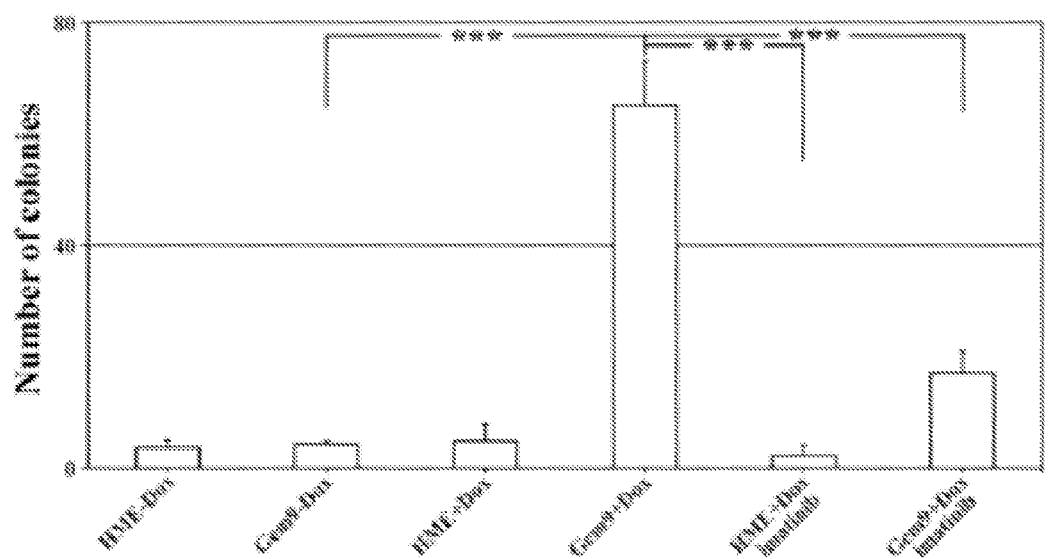
Figure 14C:
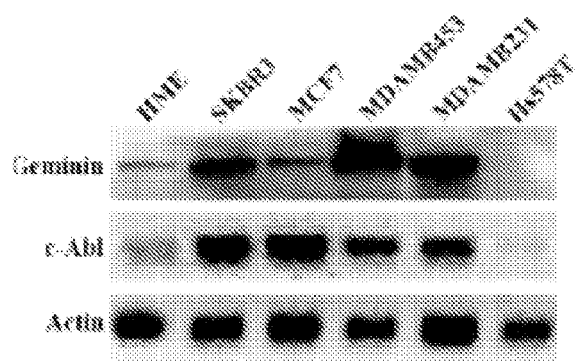
Figure 14D:
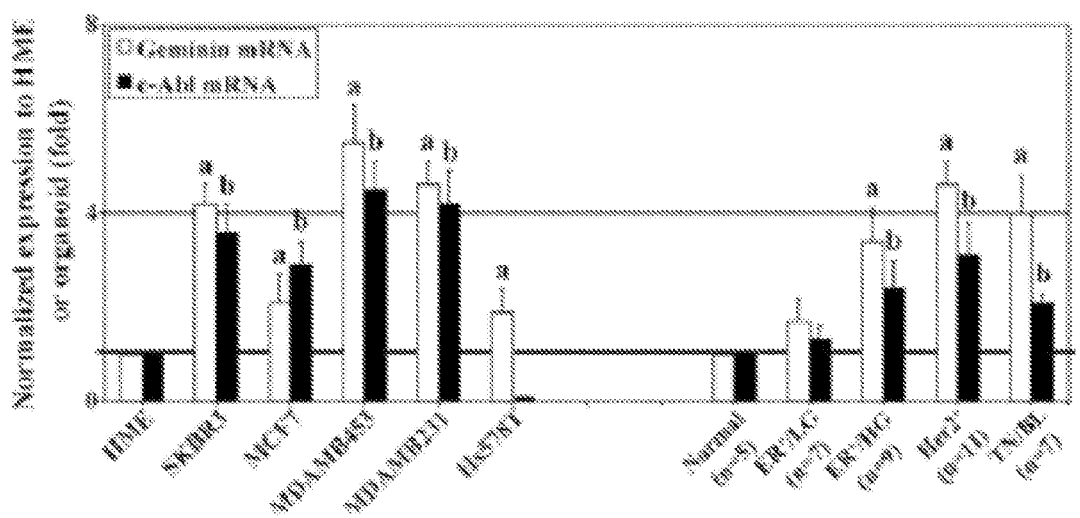

Geminin and c-Abl are Co-Overexpressed in Breast Cancer Cell Lines and Tissue Samples Expression of geminin and c-Abl was next analyzed in breast cancer cell lines and tumor samples. Compared to normal HME cell lines, all breast cancer cell lines except Hs578T showed high levels of geminin and c-Abl proteins (FIG. 14C) and mRNAs (FIG. 14D, left). Intriguingly, Hs578T cells lacked expression of geminin protein, but c-Abl mRNA and protein (FIGS. 14C and 14D, left) reinforcing the notion that binding to and/or phosphorylation by c-Abl promotes geminin protein stability and not its transcription. Moreover, RNA from 39 normal (5 samples) and primary breast tumor samples (7 low-grade $ER^+$ [$ER^+$/LG], 9 high-grade $ER^+$ [$ER^+$/HG], 11 $Her2^+$ and 7 triple negative/basal like [TN/BL]) were analyzed by real time RT/PCR. Geminin and c-Abl mRNAs expression were high in $ER^+$/HG, $Her2^+$ and TN/BL tumors, but low in $ER^+$/LG tumors (FIG. 14B, right). These data showed that c-Abl and geminin proteins and mRNAs were co-overexpressed in aggressive breast cancer cells.

Example 18

Analysis of Geminin-Positive Tumors Expression of Nuclear c-Abl

To establish the foregoing correlation further, two cohorts of paraffin embedded tissue microarrays (TMAs) were acquired. The first was a test cohort; a commercial TMA (Biomax.us) that consisted of 66 normal/cancer adjacent tissues, 180 ductal carcinoma in situ (DCIS), 100 invasive, and 165 metastatic breast tumor samples. The second was a confirmation cohort, consisting of disease-free adult tissues (including; kidney, liver, placenta, spleen, and mammary tissues) and 326 breast tumor samples (different stages) acquired from the Hawaiian *Surveillance, Epidemiology and End Results* (SEER) collection. Both sets were constructed in quadruplicate, each containing one sample from a different region of a tumor at 4 μm. After immunohistochemistry staining of the test cohort with geminin and c-Abl specific antibodies, geminin- and c-Abl-positive cells were counted in at least 10 high power fields of each tumor section and the staining was scored as follows; 0=no staining (<1% of the cells stained); 1+=weak (1-10% of the cells stained); 2+=medium (10-50% of the cells stained); 3+=strong (>50% of the cells stained). Staining scores <10% were considered negative tumors, and >10% were considered positive tumors.

Figure 14E:
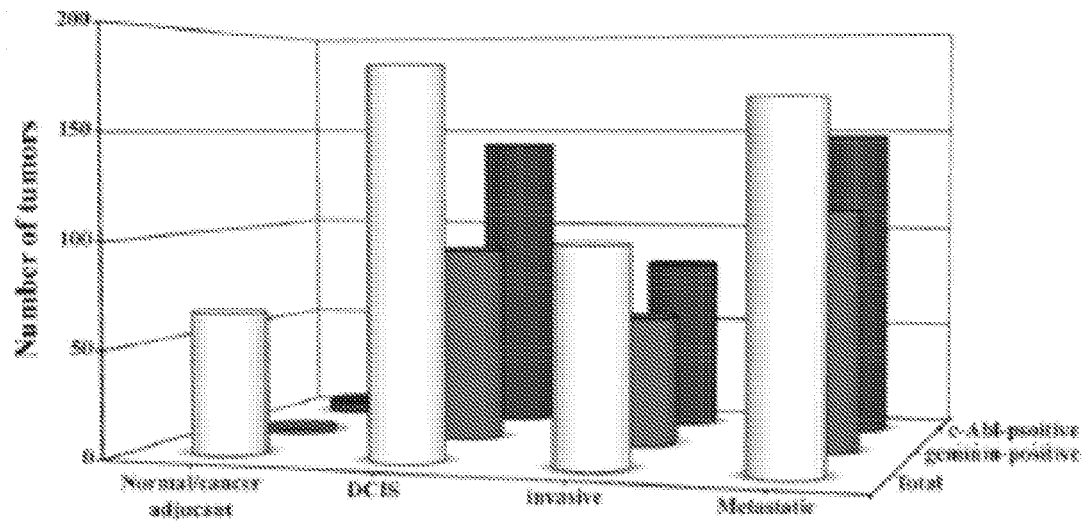
Figure 14F:
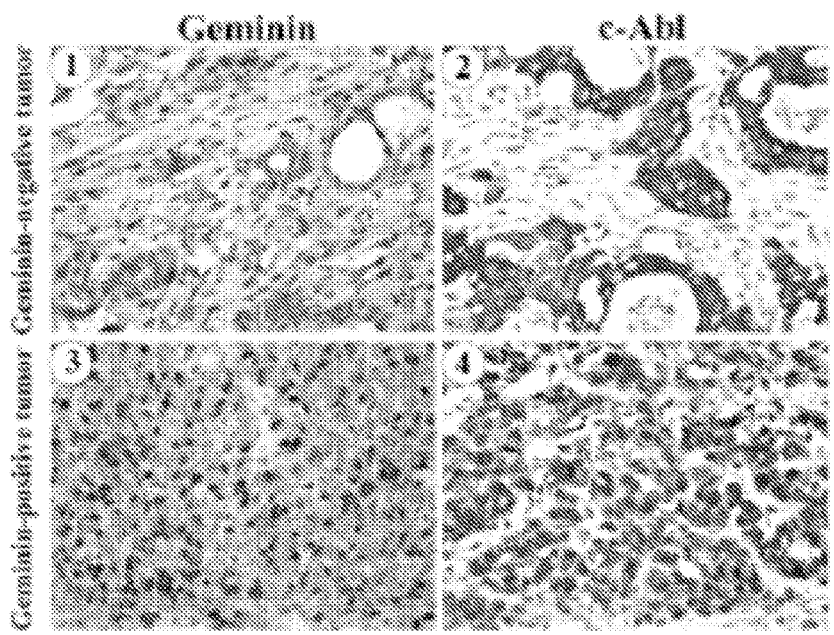

Only few cells in the normal breast tissues were positive for geminin and c-Abl. In particular, only 2/66 (3%), and 6/66 (9%) of the samples were positive for geminin and c-Abl, respectively (FIG. 14E). In contrast, 92/180 (51%) of the DCIS tumors, 61/100 (61%) of the invasive and 113/165 (68%) of the metastatic tumors were geminin positive (FIG. 14E). Similarly, 143/180 (79%) of the DCIS tumors, 82/100 (82%) of the invasive tumors, and 147/165 (89%) of the metastatic tumors were c-Abl-positive (FIG. 14E). Interestingly, geminin-negative tumors expressed c-Abl exclusively in the cytoplasm (FIGS. 14F/1 and 14F/2), whereas geminin-positive tumors expressed nuclear c-Abl exclusively (FIGS. 14F/3 and 14F/4).

To confirm these data, the conformational cohort (n=326) was also stained with anti-geminin and anti-c-Abl antibodies. Disease-free liver, placenta, and spleen tissues stained positive for both proteins. Disease free kidney and normal mammary glands on the other hand were negative. Further, 52% (n=168) of the tumors were geminin-positive, while 91% (n=296) of the tumors were c-Abl-positive. However, 57% (n=168) of these c-Abl-positive tumors expressed c-Abl exclusively in the nucleus, whereas 44% (n=132) expressed cytoplasmic c-Abl. To examine the associations of expression-levels between geminin and c-Abl in geminin-positive tumors, State v.11 to calculate Fisher's exact p values (Table 1) and Spearman correlation coefficients (r, FIG. 14D) were used.

Figure 15A:
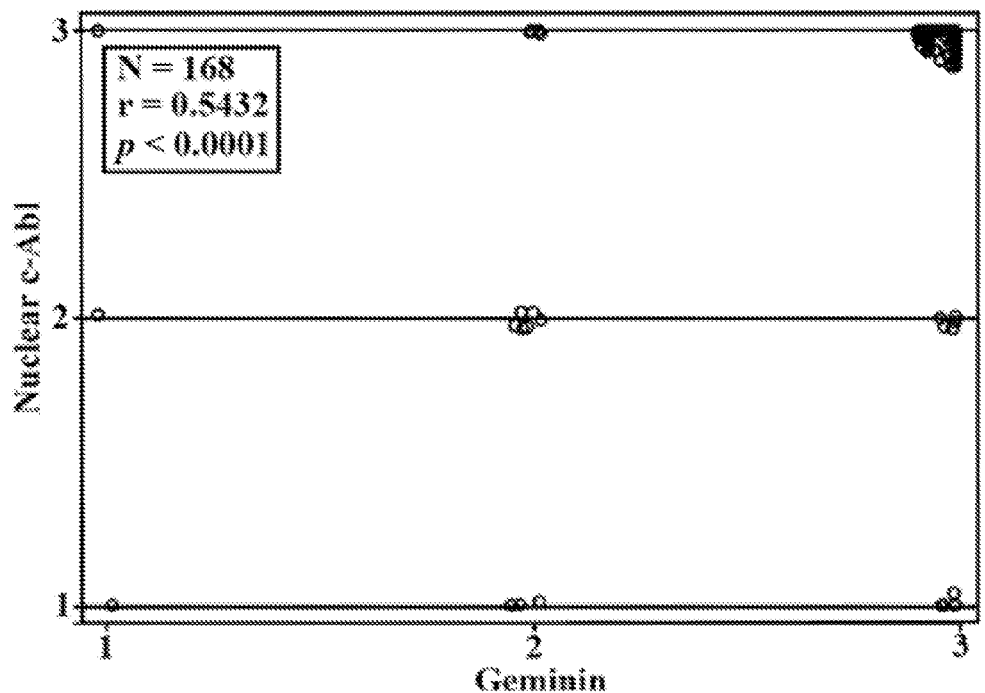
FIGS. 15A-15B include graphs showing the expression of geminin and c-Abl in breast tumor samples, including a graph showing the correlation between geminin and nuclear c-Abl expression in breast cancer tumors samples detected using immunohistochemistry (FIG. 15A); and a graph showing geminin expression in none, cytoplasmic, nuclear or nuclear/cytoplasmic c-Abl expressing Her2$^+$ (n=32) or TN/BL (n=72) tumors (FIG. 15B)

According to the Fisher's exact test, significant associations between geminin and nuclear c-Abl (p-value=0.0006, Table 1) was observed. From the nuclear c-Abl expressing tumors (n=168) all were geminin-positive (Table 1) and approximately 94% (n=142) of these showed strong (3+) geminin and nuclear c-Abl expression (Table 1). On the other hand, none of the 132 tumors expressing high levels of cytoplasmic c-Abl (Table 1) was geminin-positive (Table 1). Spearman correlation coefficient test also confirmed these data. Indeed, highly significant correlation between expression of geminin and nuclear c-Abl (Spearman rank correlation r=0.5432, p=0.0001, FIG. 15) was observed. Taken together, these data showed geminin and nuclear c-Abl overexpression as early as DCIS.

TABLE 1

Association between geminin overexpression and nuclear or cytoplasmic c-Abl in breast tumors.

| Staining Score | Nuclear c-Abl (n = 168) ([a]p < 0.0001) | | | | Cytoplasmic c-Abl (n = 132) (p = 0.9) | | | |
|---|---|---|---|---|---|---|---|---|
| | 0-1 (%) | 2 (%) | 3 (%) | Total (%) | 0-1 (%) | 2 (%) | 3 (%) | Total (%) |
| Geminin 0-1 (%) | 1 (0.60) | 1 (0.60) | 1 (0.60) | 3 (1.79) | 41 (31.06) | 57 (43.18) | 34 (25.75) | 132 (100) |
| 2 (%) | 3 (1.79) | 6 (3.57) | 5 (2.98) | 14 (8.33) | 0 (0) | 0 (0) | 0 (0) | 0 (0) |
| 3 (%) | 4 (2.38) | 5 (2.98) | 142 (84.52) | 151 (89.88) | 0 (0) | 0 (0) | 0 (0) | 0 (0) |
| Total (%) | 8 (4.76) | 12 (7.14) | 148 (88.10) | 168 (100) | 0 (31.06) | 0 (43.18) | 132 (25.75) | 132 (100) |

[a] is Fisher's exact p-value

Example 18

Figure 15B:
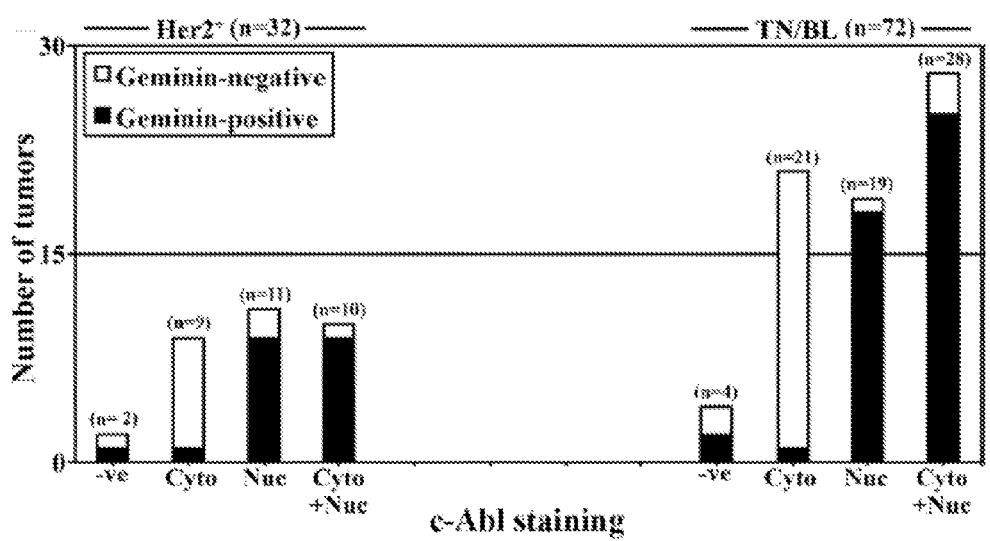

Analysis of High-Expression Geminin and Nuclear c-Abl in HER2+ and TN/BL Breast Tumors HER2+ and TN/BL are the most aggressive breast tumor subtypes, which often acquire resistance to Herceptin (the only targeted therapy for Her2+ tumors), or have no targeted therapies (TN/BL). A cohort of 32 HER2+ and 72 TN/BL tumors was identified and was immunohistochemically stained with geminin and c-Abl antibodies. Some information about these tumor grades and stages were also available. In the HER2+ cohort (n=32), 21 tumors (~66%) were geminin-positive, and only 11 tumors (34%) were geminin-negative (FIG. 15B, left). Only two tumors were c-Abl-negative, and from these one was geminin-positive and one was geminin-negative (FIG. 15B, left). c-Abl was exclusively cytoplasmic in 9 tumors, from these only 1 (11%) was geminin-positive and 8 (89%) were geminin-negative (FIG. 15B, left). c-Abl was exclusively nuclear in 11 tumors, and from these 10 (91%) were geminin-positive and only 1 (9%) was geminin-negative (FIG. 15B, left). Finally, 10 of these Her2+ tumors expressed nuclear c-Abl with some cytoplasmic staining, and from these 9 (90%) were geminin positive, while only 1 (10%) was geminin-negative (FIG. 15B, left). Similarly, in the TN/BL cohort (n=72), 46 (~64%) were geminin-positive, while only 26 (36%) were geminin-negative. Only 4 tumors were c-Abl-negative, and from these 2 were geminin-positive and 2 were geminin-negative (FIG. 15B, right). c-Abl was exclusively cytoplasmic in 21 tumors, and from these 1 (5%) was geminin-positive, whereas 20 (95%) were geminin-negative (FIG. 15B, right). c-Abl was exclusively nuclear in 19 TN/BL tumors, and from these 18 (95%) were geminin-positive and only 1 (5%) was geminin-negative (FIG. 15B, right). Finally, from the 28 tumors that expressed nuclear c-Abl, but also showed some cytoplasmic staining, 25 (89%) were geminin-positive, and only 3 (11%) were geminin-negative (FIG. 15B, right). These data showed that even in the most aggressive breast cancer subtypes, geminin was overexpressed specifically in nuclear c-Abl overexpressing tumors.

Example 19

Analysis of High-Geminin Expression and Aggressive Phenotypes in HER2+ and TN/BL Tumors All HER2+/geminin-negative tumors (n=11) were grade 2 (p=0.0723, Table 2). Seven (64%) of these HER2+/geminin-negative tumors were localized tumors, while 4 (36%, p=0.0503) were lymph node positive tumors (Table 2). In contrast, 5 (24%) HER2+/geminin-positive tumors were grade 2 and 16 (76%) were grade 3 tumors (p=0.0012, Table 2). Eight (38%) of these HER2+/geminin-positive tumors were localized tumors, 4 (19%) were lymph-node positive tumors, whereas 9 (43%) showed distant metastases (p=0.0109, Table 2). Further, from the TN/BL/geminin-negative tumors (n=26), 21 (81%) were grade 2 tumors, while only 5 were grade 3 (19%, p=0.0525, Table 2). Sixteen (62%) of these TN/BL/geminin-negative tumors were localized tumors and 10 (38%) were lymph-node positive tumors (p=0.0042, Table 2). In contrast, 13 (28%) TN/BL/geminin-positive tumors were grade 2 tumors, while 33 (72%) were grade 3 tumors (p=0.0056, Table 2). Eighteen of these TN/BL/geminin-positive tumors (39%) were localized tumors, 15 (33%) were lymph-node positive tumors, and 13 (28%) showed distant metastasis (p=0.0022, Table 2). These data show that geminin positivity correlates with adverse breast tumor status.

TABLE 2

Relationships between geminin expression and tumor characteristics in Her2+ and TN/BL breast cancer tumor sample.

| Characteristics | Her2+ ( n = 32) | | TN/BL (n = 72) | |
|---|---|---|---|---|
| | geminin-positive (%) (n = 21) | geminin-negative (%) (0 = 11) | geminin-positive (%) (n = 46) | geminin-negative (%) (a = 26) |
| Tumor Grade (as modified nuclear grade) | | | | |
| 1 | 0 (0) | 0 (0) | 0 (0) | 0 (0) |
| 2 | 5 (25) | 12 (100) | 13 (28) | 21 (81) |
| 3 | 16 (75) | 0 (0) | 33 (72) | 5 (19) |
| *p-value | 0.0012 | 0.0723 | 0.0056 | 0.0525 |
| Tumor Stage | | | | |
| In situ | 0 (0) | 0 (0) | 0 (0) | 0 (0) |
| Localized | 8 (40) | 7 (67) | 18 (39) | 16 (62) |
| Lymph-node | 4 (20) | 4 (33) | 15 (33) | 10 (38) |
| Distant Mets | 9 (40) | 0 (0) | 13 (28) | 0 (0) |
| p-value | 0.0109 | 0.0503 | 0.0022 | 0.0042 |

*To compare multiple groups with one control group, anaylsis of variance (ANOVA) was used. p-values (two-sided) <0.05 were considered statistically significant

Example 20

Figure 16:
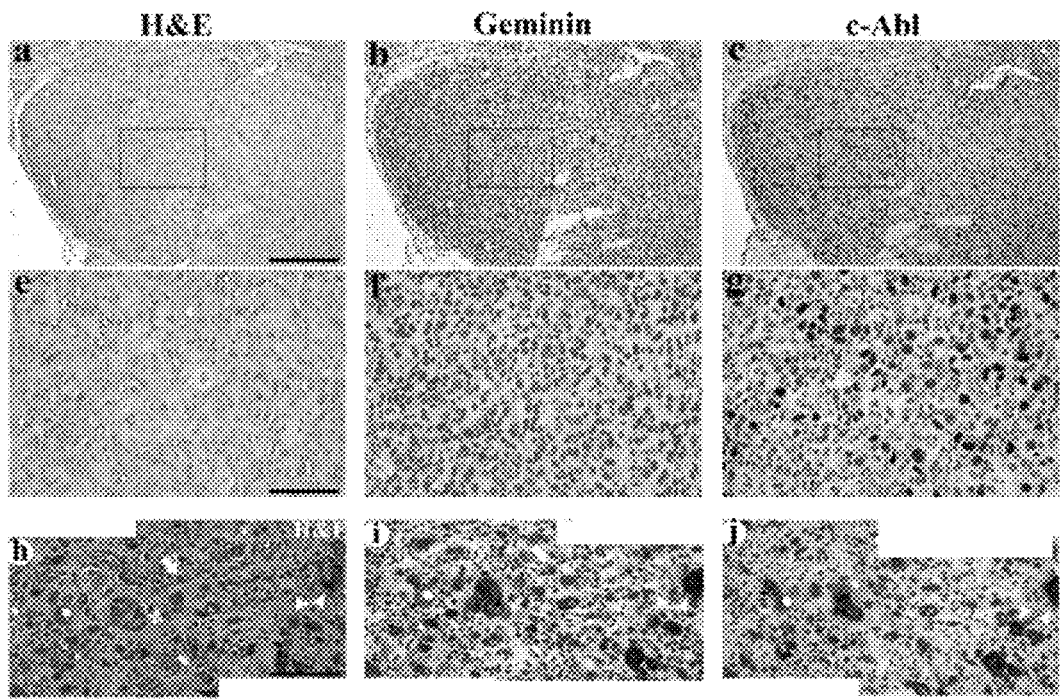
FIG. 16 includes images showing the histological and immunohistochemical analysis of geminin overexpressing mammary tumors.

Analysis of Geminin Induction of Aggressive Mammary Tumors Expressing High Levels of Nuclear c-Abl As described in the examples provided herein above, HME clones expressing TERT, TERT/SV40-large T antigen (TERT/LT) or TERT/geminin (i.e. induced Gem9) did not form tumors when injected in SCID mice ($5 \times 10^6$ cells mixed 1:1 with matrigel). However, clones expressing TERT/LT/geminin (i.e. induced Gem9/LT n=10 mice) formed subcutaneously or orthotopically aggressive, invasive and aneuploid tumors. To analyze expression of c-Abl in these geminin-driven tumors, tumor sections containing normal as well as abnormal size (aneuploid) tumor cell nuclei (see hematoxylin and eosin (H&E) stained sections, FIGS. 16/a, 16/e and 16/h) were immunohistochemically stained with anti-geminin and -c-Abl antibodies. Whether tumor cells showed normal size nuclei (FIGS. 16/a to 16/g) or abnormal size nuclei (see arrow and arrowheads in FIGS. 16/h-16/j), these geminin-driven tumors (FIGS. 16/b, 16/f, and 16/i) also expressed exclusively nuclear c-Abl (FIGS. 16/c, 16/g, and 16/j). These data showed that nuclear c-Abl expression was geminin-driven.

Example 21

Geminin Overexpressing Mammary Tumors are Imatinib Sensitive

Figure 17A:
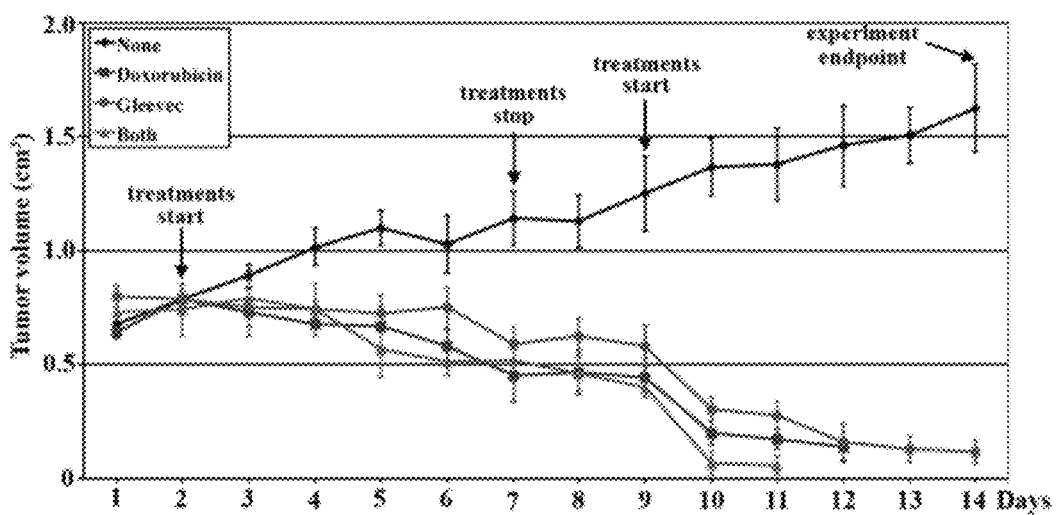
FIGS. 17A-17C include a graph and images showing the effect of imatinib on geminin overexpressing tumors, including a graph showing the results of an experiment where geminin overexpressing tumors were untreated, treated with 5 mg/kg/day doxorubicin, 50 mg/kg/day imatinib, or both when tumors reached approximately 0.5 cm$^3$ (FIG. 17A); images of mice with subcutaneous geminin-driven tumors untreated (left) or treated with imatinib (right) at day 12 (FIG. 17B); and images of mice mammary tumors untreated (left) or treated with imatinib (right) (FIG. 17C).
Figure 17B:
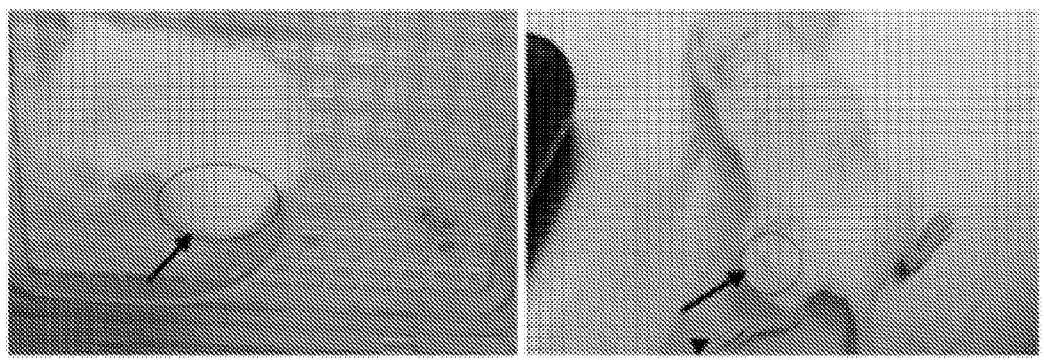
Figure 17C:
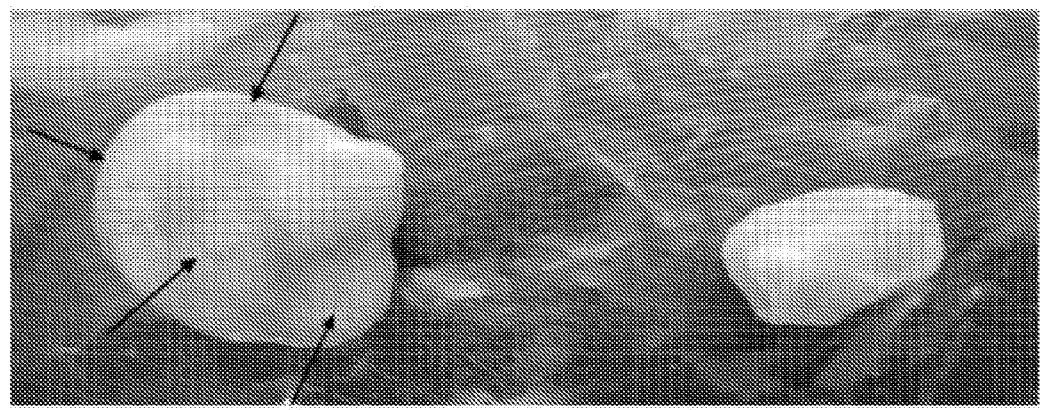

To evaluate the efficacy of the c-Abl inhibitor imatinib on geminin-driven tumors, two sets of 40 SCID mice were injected subcutaneously or orthotopically with $5 \times 10^6$ Gem9/LT cells each and mice were maintained on doxycycline-supplemented water. At approximately 30 days post-injection, tumors were 0.5 to 0.7 cm³ in size, at which time mice in each set were divided into 4 groups, one received no treatment, one received 5 mg/kg/day of doxorubicin, one received 50 mg/kg/day of imatinib and the last group received doxorubicin and imatinib at the same concentrations. Tumors were monitored weekly using Xenogen in vivo imaging, and tumor size was measured daily with a caliper. From FIGS. 17A-17C (orthotoptically injected mice data are shown), it is clear that imatinib was as effective in killing geminin-driven tumors as doxorubicin (FIG. 17A). Unlike doxorubicin, however, imatinib treatment was much less toxic to the mice. Indeed, while doxorubicin treatment at this concentration led to adverse side effects including death (FIG. 17A), all but 1 mouse survived imatinib treatment at the dose used until the experiment termination (14 days later, FIG. 17A). Furthermore, subcutaneously injected mice retained massive tumors on their left thighs when received no treatment (see circle, FIG. 17B, left). In contrast, subcutaneous tumors in mice treated with imatinib were barely detectable (see circle, FIG. 17B, right). Also orthotopically injected mice retained massive mammary tumors when received no treatment (FIG. 17C, left). Conversely, mammary tumors in mice treated with imatinib were at least 5-10 fold smaller (FIG. 17C, right). Noteworthy, the combination treatment "doxorubicin+imatinib" had a slight additive effect (FIG. 17A). These data show that imatinib can be used to treat geminin-overexpressing tumors.

Discussion of Examples 12-21.

Cytokinesis failure leads to aneuploidy and cause cancer progression (Duesberg et al., 1999; Margolis, 2005). Geminin overexpression induces cytokinesis skipping (failure) and leads to aneuploidy, in vitro (Gardner et al., 2011) and to formation of invasive and aneuploid tumors, in vivo (Blanchard et al., 2011). Overexpression of tyrosine-phosphorylated geminin only can induce aneuploidy by premature inhibition of topoisomerase II alpha (TopoIIα) and Aurora B kinase functions (AurB, Gardner et al., 2011; Blanchard et al., 2011). Mitotic chromosome condensation, segregation, and subsequently cytokinesis in mammalian cells are regulated, in part, by (S10)-H3 phosphorylation by Aurora B kinase (Giet et al., 2001; Ruchaud et al., 2007). Dephosphorylation and chromosome decondensation in $G_1$, on the other hand, is regulated by PP1-dependent mechanism (Sistayanarian et al., 2006).

Geminin is tyrosine phosphorylated in $G_2$/M/early $G_1$ cells (Nakuci et al., 2006). The fact that silencing of c-Abl or inhibiting its activity (also mutating Y150 into A, Blanchard et al., 2011) leads to cell death specifically in cells overexpressing geminin supports the conclusion that tyrosine 150 phosphorylation is important for the stability of geminin protein and cell survival when geminin is overexpressed. The simplest explanation is that geminin overexpressing cells become addicted to high-level geminin, perhaps to maintain their ability to propagate in an aneuploid fashion. In fact, the suppression of DNA damage signals (Gardner et al., 2011) and/or induction of expression of survival factors, such as Bcl2 and Bcl-xL (Blanchard et al., 2011) in geminin overexpressing cell support that assumption.

The fact that only $G_2$/M c-Abl was able to phosphorylate geminin, in vitro indicates that c-Abl itself is differentially modified in $G_2$/M in a way that allows it to bind and/or phosphorylate geminin. Previous data showed that cyclin A/ or B/Cdk1 complex phosphorylates and activates c-Abl (Lover et al., 1994). In keeping with that, an increase in cyclin A and cdk1 expression in geminin overexpressing cells was recently observed (Gardner et al., 2011).

One of the unexpected results from the foregoing studies was that geminin was only overexpressed in breast tumors expressing nuclear c-Abl. Normally, the monopolar spindle 1 kinase (Mps1/TTK) phosphorylates c-Abl on T735 (Yoshida et al., 2005), inducing its binding to 14-3-3 (most likely σ) and the retention in the cytoplasm (Mancini et al., 2009). Upon mitogenic stimulation or geno-/cell-toxic stressing of cells, JNK is activated, which phosphorylates 14-3-3σ leading to the release of c-Abl and its translocation to the nucleus (Yoshida et al., 2005). For c-Abl to be retained in the nucleus, it is possible that it is mutated on T735 in geminin overexpressing breast tumors. It is also possible that Mps1/TTK is inactive or that 14-3-3σ expression is decreased in these tumors. In fact, hypermethylation of the 14-3-3σ promoter and decrease expression has been reported in breast cancers (Zurita et al., 2010). Finally, JNK could be over-activated in geminin overexpressing cells.

Collectively, the foregoing data indicate a novel role for p-Y150-geminin by nuclear c-Abl as a novel breast cancer oncogene that causes genomic instability when overexpressed through an aberration of its normal cytokinetic function and that c-Abl has an important role in breast cancer development and progression (Lin and Arlinghaus, 2008), especially those overexpressing geminin. In this regard, the foregoing studies further indicate that c-Abl inhibitors, such as imatinib, can be effectively used to treat cancer patients, including breast cancer patients, with geminin and/or nuclear c-Abl overexpressing aggressive/metastatic cancers.

Throughout this document, various references are mentioned. All such references are incorporated herein by reference, including the references set forth in the following list:

REFERENCES

1. Storchova Z, Pellman D. From polyploidy to aneuploidy, genome instability and cancer. Nat Rev Mol Cell Biol. 2004; 5: 45-54.

2. Eggert U, Mitchison T, Field C. Animal cytokinesis: from parts list to mechanisms Ann Rev Biochem. 2006; 75: 543-566.
3. Ganem N, Storchova Z, Pellman D. Tetraploidy, aneuploidy and cancer. Curr Opin Genet Dev. 2007; 17: 157-162.
4. Guizetti J, Gerlich D. Cytokinetic abscission in animal cells. Semin Cell Dev Biol. 2010; 21(9): 909-916.
5. Cimini D, Wan X, Hirel C, Salmon E. Aurora kinase promotes turnover of kinetochore microtubules to reduce chromosome segregation errors. Curr Biol. 2006; 16: 1711-1718.
6. Norden C, Mendoza M, Dobbelaere J, Kotwaliwale C, Biggins S, Barral Y. The NoCut pathway links completion of cytokinesis to spindle midzone function to prevent chromosome breakage. Cell. 2006; 125: 85-98.
7. Ruchaud S, Carmena M, Earnshaw C. Chromosomal passengers: conducting cell division. Nat Rev Mol Cell Biol. 2007; 8: 798-812.
8. Xu Z, Ogawa H, Vagnarelli P, Bergmann J, Hudson D, Ruchaud S, Fukagawa T, Earnshaw W, Samejima K. INCENP-aurora B interactions modulate kinase activity and chromosome passenger complex localization. J Cell Biol. 2009; 187(5): 637-653.
9. Wheatley S. Chromosome 'by-Aurora-ientation' during mitosis. Cell Biol Int. 2011; 35(6): 575-578.
10. Ahonen L, Kukkonen A, Pouwels J, Bolton M, Jingle C, Stukenberg P, Kallio M. Perturbation of Incenp function impedes anaphase chromatid movements and chromosomal passenger protein flux at centromeres. Chromosoma. 2009; 118(1): 71-84.
11. Wohlschlegel J, Dwyer B, Dhar S, Cvetic C, Walter J, Dutta A Inhibition of eukaryotic DNA replication by geminin binding to Cdt1. Science. 2000; 290: 2309-2312.
12. McGarry T, Kirschner M. Geminin, an inhibitor of DNA replication, is degraded during mitosis. Cell. 1998; 93(6): 1043-5321.
13. Del Bene F, Tessmar-Raible K, Wittbrodt J. Direct interaction of geminin and Six3 in eye development. Nature. 2004; 427(6976): 745-749.
14. Luo L, Yang X, Takihara Y, Knoetgen H, Kessel M. The cell-cycle regulator geminin inhibits Hox function through direct and Polycomb mediated interactions. Nature. 2004; 427(6976): 749-753.
15. Seo S, Herr A, Lim J, Richardson G, Richardson H, Kroll K. Geminin regulates neuronal differentiation by antagonizing Brgl activity. Genes Dev. 2005; 19(14): 1723-1734.
16. Karamitros D, Kotantaki P, Lygerou Z, Kioussis D, Taraviras S. T cell proliferation and homeostasis: an emerging role for the cell cycle inhibitor geminin. Crit Rev Immunol. 2011; 31(3): 209-231.
17. Wong P, Glozak M, Cao T, Vaziri C, Seto E, Alexandrow M. Chromatin unfolding by Cdt1 regulates MCM loading via opposing functions of HBO1 and HDAC11-geminin. Cell Cycle. 2010; 9(21): 4351-4363.
18. Yang V, Carter S, Hyland S, Tachibana-Konwalski K, Laskey R, Gonzalez M. Geminin escapes degradation in G1 of mouse pluripotent cells and mediates the expression of Oct4, Sox2, and Nanog. Curr Biol. 2011; 21(8): 692-699.
19. McGarry T. Geminin deficiency causes a Chk1-dependent $G_2$ arrest in *Xenopus*. Mol Biol Cell. 2002; 13(10): 3662-3671.
20. Nakuci E, Xu M, Pujana M, Valls J, ElShamy W M. Geminin is bound to chromatin in G2/M phase to promote proper cytokinesis. Int J Biochem Cell Biol. 2006; 38(7): 1207-1220.
21. Hara K, Nakayama K, Nakayama K. Geminin is essential for the development of preimplementation mouse embryos. Genes Cells. 2006; 11(11): 1281-1293.
22. Gardner L, Malik R, Shimizu Y, ElShamy, WM. Geminin overexpression prevents the completion of topoisomerase IIα chromosome decatenation leading to aneuploidy in human mammary epithelial cells. Breast Cancer Res. 2011; 13(53).
23. Montanari M, Boninsegna A, Faraglia B, Coco C, Giordano A, Cittadini A, Sgambato A. Increased expression of geminin stimulates the growth of mammary epithelial cells and is a frequent event in human tumors. J Cell Physiol. 2005; 202(1): 215-22.
24. Wei Y, Yu L, Bowen J, Gorovsky M, Allis C. Phosphorylation of histone H3 is required for proper chromosome condensation and segregation. Cell. 1999; 97(1): 99-109.
25. Delacour-Larose M, Thi M, Dimitrov S, Molla A. Role of survivin phosphorylation by aurora B in mitosis. Cell Cycle. 2007; 6(15): 1878-1885.
26. Elenbaas B, Spirio L, Koerner F, Fleming M, Zimonjic D, Donaher J, Popescu N, Hahn W, Weinberg R. Human breast cancer cells generated by oncogenic transformation of primary mammary epithelial cells. Genes Dev. 2001; 15(1): 50-65.
27. Mirzai M. Tuberculoma of the cervical spinal canal mimicking en plaque meningioma. J Spinal Disord Tech. 2005; 18(2): 197-199.
28. Yaccoby S, Johnson C, Mahaffey S, Wezeman M, Barlogie B, Epstein, J. Antimyeloma efficacy of thalidomide in the SCID-hu model. Blood. 2002 100: 4162-4168.
29. Barnes N, Warnberg F, Farnie G, White D, Jiang W, Anderson E, Bundred N. Cyclooxygenase-2 inhibition: effects on tumour growth, cell cycling and lymphangiogenesis in a xenograft model of breast cancer. Br J Cancer. 2007; 96(4): 575-582.
30. Lamszus K, Jin L, Fuchs A, Shi E, Chowdhury S, Yao Y, Polverini P, Laterra J, Goldberg I, Rosen E. Scatter factor stimulates tumor growth and tumor angiogenesis in human breast cancers in the mammary fat pads of nude mice. Lab Invest. 1997; 76(3): 339-353.
31. Tada S, Li A, Maiorano D, Mechali M, Blow J. Repression of origin assembly in metaphase depends on inhibition of RLF-B/Cdt1 by geminin. Nat Cell Biol. 2001; 3: 107-113.
32. Gonzalez M, Tachibana K, Chin S, Callagy G, Madine M, Vowler S, Pinder S, Laskey R, Coleman N. Geminin predicts adverse clinical outcome in breast cancer by reflecting cell-cycle progression. J Pathol. 2004; 204(2): 121-130.
33. Wohlschlegel J, Kutok J, Weng A, Dutta A. Expression of geminin as a marker of cell proliferation in normal tissues and malignancies. Am J Pathol. 2002; 161(1): 267-273.
34. Chang H, Nuyten D, Sneddon J, Hastie T, Tibshirani R, Sørlie T, Dai H, He Y D, van't Veer L J, Bartelink H, van de Rijn M, Brown P O, van de Vijver M J. Robustness, scalability, and integration of a wound-response gene expression signature in predicting breast cancer survival. Proc Natl Acad Sci USA. 2005; 102: 3738-3743.
35. Chin K, DeVries S, Fridlyand J, Spellman P, Roydasgupta R, Kuo W L, Lapuk A, Neve R M, Qian Z, Ryder T, Chen F, Feiler H, Tokuyasu T, Kingsley C, Dairkee S, Meng Z, et al. Genomic and transcriptional aberrations linked to breast cancer pathophysiologies. Cancer Cell. 2006. 10: 529-541.
36. van't Veer L, Dai H, van de Vijver H, He Y, Hart A, Mao M, Peterse H, van der Kooy K, Marton M, Witteveen A. Schreiber G J, Kerkhoven R M, Roberts C, Linsley P S, Bernards R, Friend S. Gene expression profiling predicts clinical outcome of breast cancer. *Nature*. 2002; 415: 530-536.
37. Weaver B, Silk A, Montagna C, Verdier-Pinard P, Cleveland D. Aneuploidy acts both oncogenically and as a tumor suppressor. *Cancer Cell*. 2007; 11: 25-36.
38. Guse A, Mishima M, Glotzer M. Phosphorylation of ZEN-4/MKLP1 by aurora B regulates completion of cytokinesis. *Curr Biol*. 2005; 15: 778-786.
39. Meraldi P, Honda R, Nigg E. Aurora-A overexpression reveals tetraploidization as a major route to centrosome amplification in p53-/-cells. *EMBO J*. 2002; 21: 483-492.
40. Lampson M, Renduchitala K, Khodjakov A, Kapoor T. Correcting improper chromosome-spindle attachments during cell division. *Nat Cell Biol*. 2004; 6: 232-237.
41. Lang J-Y, Hsu J, Maric-Bernstam F, Chang C-J, Wang Q, Bao Y, Yamaguchi H, Xie X, Woodward W, Yu D, Hortobagyi G N, Hung M C. BikDD eliminates Breast Cancer Initiating Cells and Synergize with Lapatinib for Breast Cancer Treatment. *Cancer Cell*. 2011; 20: 341-356.
42. Dobles M, Liberal V, Scott M, Benezra, Sorger R. Chromosome missegregation and apoptosis in mice lacking the mitotic checkpoint protein Mad2. *Cell*. 2000; 101: 635-645.
43. Wang Q, Liu T, Fang Y, Xie S, Huang X, Mahmood R, Ramaswamy G, Sakamoto K-M, Darzynkiewicz Z, Xu M, Dai W. BUBR1 deficiency results in abnormal megakaryopoiesis. *Blood*. 2004; 103: 1278-1285.
44. Baker D, Jeganathan K, Cameron J, Thompson M, Juneja S, Kopecka A, Kumar R, Jenkins R, de Groen P, Roche P, van Deursen J. BubR1 insufficiency causes early onset of aging-associated phenotypes and infertility in mice. *Nat Genet*. 2004; 36: 744-749.
45. Michel L, Liberal V, Chatterjee A, Kirchwegger R, Pasche B, Gerald W, Dobles M, Sorger P, Murty V, Benezra R. MAD2 haplo-insufficiency causes premature anaphase and chromosome instability in mammalian cells. *Nature*. 2001; 409: 355-359.
46. Dai W, Wang Q, Liu T, Swamy M, Fang Y, Xie S, Mahmood R, Yang Y, Xu M. Rao C. Slippage of mitotic arrest and enhanced tumor development in mice with BubR1 haploinsufficiency. *Cancer Res*. 2004; 64: 440-445.
47. Aoyama K, Fukumoto Y, Ishibashi K, Kubota S, Morinaga T, Horiike Y et al. (2011). Nuclear c-Abl-mediated tyrosine phosphorylation induces chromatin structural changes through histone modifications that include H4K16 hypoacetylation. *Exp Cell Res* 317: 2874-2903.
48. Baskaran R, Wood L, Whitaker L, Canman C, Morgan S, Xu Y et al. (1997). Ataxia telangiectasia mutant protein activates c-Abl tyrosine kinase in response to ionizing radiation. *Nature* 387: 516-519.
49. Blanchard Z, Malik R, Mullins N, Maric C, Luk H, Horio D et al. (2011). Geminin overexpression induces mammary tumors via suppressing cytokinesis. *Oncotarget* 2(12): 1011-1027.
50. Colicelli J. (2010). ABL tyrosine kinases: evolution of function, regulation, and specificity. *Sci Signal* 3(139): re6.
51. DeMatteo R P. Nanoneoadjuvant therapy of gastrointestinal stromal tumor (GIST). (2009). *Ann Surg Oncol* 16: 799-800.
52. Druker B J, Talpaz M, Resta D J, Peng B, Buchdunger E, Ford J et al. (2001). Efficacy and safety of a specific inhibitor of the BCR-ABL tyrosine kinase in chronic myeloid leukemia. *N Engl J Med* 344: 1031-1037.
53. Duesberg P, Rasnick D, Li R, Winters L, Rausch R, Hehlmann R. (1999). How aneuploidy may cause cancer and genetic instability. *Anticancer Res* 19(6A): 4887-4906.
54. ElShamy W M, Livingston D M. (2004). Identification of BRCA1-IRIS, a BRCA1 locus product. *Nat Cell Biol* 6(10): 954-967.
55. Ganguly S, Fiore L, Sims L, Friend J, Srinivasan D, Thacker M et al. (2012). c-Abl and Arg are activated in human primary melanomas, promote melanoma cell invasion via distinct pathways, and drive metastatic progression. *Oncogene* 31(14): 1804-1816.
56. Giet R, Glover M. (2001). *Drosophila* Aurora B kinase is required for histone H3 phosphorylation and condensing recruitment during chromosome condensation and to organize the central spindle during cytokinesis. *J Cell Biol* 152: 669-681.
57. Kadam S, McAlpine G, Phelan M, Kingston R, Jones K, Emerson B. (2004). Functional selectivity of recombinant mammalian SWI/SNF subunits. *Genes Dev* 14: 2441-2451.
58. Kroll K, Salic A, Evans L, Kirschner M. (1998). Geminin, a neutralizing molecule that demarcates the future neural plate at the onset of gastrulation. *Development* 125: 3247-3258.
59. Lin J, Sun T, Ji L, Deng W, Roth J, Minna J et al. (2007). Oncogenic activation of c-Abl in non-small cell lung cancer cells lacking FUS 1 expression: inhibition of c-Abl by the tumor suppressor gene product Fusl. *Oncogene* 26: 6989-6996.
60. Lin J, Arlinghaus R. (2008). Activated c-Abl tyrosine kinase in malignant solid tumors. *Oncogene* 27: 4385-4391.
61. Loyer P, Glaise D, Cariou S, Baffet G, Meijer L, Guguen-Guillouzo C. (1994). Expression and activation of cdks (1 and 2) and cyclins in the cell cycle progression during liver regeneration. *J Biol Chem* 269(4): 2491-2500.
62. Mancini M, Veljkovic N, Corradi V, Zuffa E, Corrado P et al. (2009). 14-3-3 ligand prevents nuclear import of c-ABL protein in chronic myeloid leukemia. *Traffic* 10(6): 637-647.
63. Margolis R. (2005). Tetraploidy and tumor development. *Cancer Cell* 8(5): 353-354.
64. Melo L. (1996). The diversity of BCR-ABL fusion proteins and their relationship to leukemia phenotype. *Blood* 88: 2375-2384.
65. Nakuci E, Xu M, Pujana M, Valls J, ElShamy W M. (2006). Geminin is bound to chromatin in G2/M phase to promote proper cytokinesis. *Int J Biochem Cell Biol* 38(7): 1207-1220.
66. Plattner R, Kadlec L, DeMali K, Kazlauskas A, Pendergast A. (1999). c-Abl is activated by growth factors and Src family kinases and has a role in the cellular response to PDGF. *Genes Dev* 13: 2400-2411.
67. Santos F P, Ravandi F. (2009). Advances in treatment of chronic myelogenous leukemia—new treatment options with tyrosine kinase inhibitors. *Leuk Lymphoma* 50(Suppl 2): 16-26.
68. Shaul Y, Ben-Yehoyada M. (2005). Role of c-Abl in the DNA damage stress response. *Cell Res* 15: 33-35.
69. Sirvent A, Benistant C, Roche S. (2008). Cytoplasmic signaling by the c-Abl tyrosine kinase in normal and cancer cells. *Biol Cell* 100: 617-631.
70. Sistayanarain A, Tsuneyama K, Zheng H, Takahashi H, Nomoto K et al. (2006). Expression of Aurora-B kinase and phosphorylated histone H3 in hepatocellular carcinoma. *Anticancer Res* 26(5A): 3585-3593.
71. Srinivasan D, Plattner P. (2006). Activation of Abl tyrosine kinases promotes invasion of aggressive breast cancer cells. *Cancer Res* 66: 5648-5655.

72. Srinivasan D, Kaetzel D M, Plattner R. (2009). Reciprocal regulation of Abl and receptor tyrosine kinases. *Cell Signal* 21: 1143-1150.
73. Taagepera S, McDonald D, Loeb J, Whitaker L, McElroy A, Wang J et al. (1998). Nuclear-cytoplasmic shuttling of c-Abl tyrosine kinase. *Proc Natl Acad Sci USA* 95: 7457-7462.
74. Thépaut M, Maiorano D, Guichou J F, Augé M T, Dumas C, Médiali M et al. (2004). Crystal structure of the coiled-coil dimerization motif of geminin: structural and functional insights on DNA replication regulation. *J Mol Biol* 342(1): 275-287.
75. Van Etten R, Jackson P, Baltimore D, Sanders M, Matsudaira P, Janmey P. (1994). The COOH terminus of the c-Abl tyrosine kinase contains distinct F- and G-actin binding domains and bundling activity. *J Cell Biol* 124: 325-340.
76. Wang W, Xue Y, Zhou S, Kuo A, Cairns B R, Crabtree G R. (1996). Diversity and specialization of mammalian SWI/SNF complexes. *Genes Dev* 10: 2117-2130.
77. Yoshida K, Yamaguchi Y, Natsume T, Kufe D, Miki Y. (2005). JNK phosphorylation of 14-3-3 proteins regulates nuclear targeting of c-Abl in the apoptotic response to DNA damage. *Nat Cell Biol* 7(3): 278-285.
78. Zurita M, Lara P, del Moral R, Torres B, Linares-Fernandez J, Arrabal S et al. (2010). Hypermethylated 14-3-3-sigma and ESR1 gene promoters in serum as candidate biomarkers for the diagnosis and treatment efficacy of breast cancer metastasis. *BMC Cancer* 10: 217.

It is understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for diagnosing a cancer treatable with a c-Abl inhibitor in a subject, comprising:
   (a) providing a biological sample from the subject including one or more cells;
   (b) immunohistochemically staining the one or more cells in the sample with an antibody against geminin and with an antibody against c-Abl;
   (c) determining an amount in the one or more cells in the sample of geminin and nuclear c-Abl;
   (d) comparing the amount of geminin and nuclear c-Abl, in the one or more cells in the sample, if present, to a control level of geminin and nuclear c-Abl; and
   (e) diagnosing the subject as having a cancer treatable with a c-Abl inhibitor if there is a measurable increase in the amount of geminin and nuclear c-Abl in the one or more cells in the sample as compared to the control level.

2. The method of claim 1, wherein the cancer treatable with a c-Abl inhibitor is selected from the group consisting of breast cancer, liver cancer, ovarian cancer, colon cancer, brain cancer, lung cancer, and prostate cancer.

3. The method of claim 2, wherein the breast cancer is a human epidermal growth factor receptor 2-positive (HER2+) breast cancer or a triple negative breast cancer.

4. The method of claim 1, wherein the biological sample comprises a tissue biopsy.

5. The method of claim 1, wherein the subject is human.

6. The method of claim 1, wherein the subject has a cancer treatable with a c-Abl inhibitor.

7. The method of claim 1, further comprising selecting a treatment or modifying a treatment for the cancer based on the determined amount of geminin and nuclear c-Abl.

8. A method for determining whether to initiate or continue treatment of a cancer treatable with a c-Abl inhibitor in a subject, comprising:
   (a) providing a series of biological samples including one or more cells over a time period from the subject;
   (b) immmunohistochemically staining the one or more cells in the series of biological samples with an antibody against geminin and with an antibody against c-Abl;
   (c) analyzing the one or more cells in the series of biological samples to determine an amount in each of the one or more cells in the biological samples of geminin and nuclear c-Abl; and
   (d) comparing any measurable change in the amounts of geminin and nuclear c-Abl, in each of the one or more cells in the biological samples to thereby determine whether to initiate or continue the therapy of the cancer with an effective amount of a c-Abl inhibitor.

9. The method of claim 8, wherein the cancer treatable with a c-Abl inhibitor is selected from the group consisting of breast cancer, liver cancer, ovarian cancer, colon cancer, brain cancer, lung cancer, and prostate cancer.

10. The method of claim 9, wherein the breast cancer is a human epidermal growth factor receptor 2-positive (HER2+) breast cancer or a triple negative breast cancer.

11. The method of claim 8, wherein the biological sample comprises a tissue biopsy.

12. The method of claim 8, wherein the series of biological samples comprises a first biological sample collected prior to initiation of the prophylaxis or treatment for the cancer and a second biological sample collected after initiation of the prophylaxis or treatment.

13. The method of claim 8, wherein the series of biological samples comprises a first biological sample collected prior to onset of the cancer and a second biological sample collected after the onset of the cancer.

14. A method for treating a cancer in a subject in need thereof, comprising:
   identifying a subject as having a cancer treatable with a c-Abl inhibitor if there is a measurable increase in the amount of geminin and nuclear c-Abl, in one or more cells in a biological sample obtained from the subject; and
   administering an effective amount of a c-Abl inhibitor to the subject.

15. The method of claim 14, wherein the cancer treatable with a c-Abl inhibitor is selected from the group consisting of breast cancer, liver cancer, ovarian cancer, colon cancer, brain cancer, lung cancer, and prostate cancer.

16. The method of claim 14, wherein the breast cancer is a human epidermal growth factor receptor 2-positive (HER2+) breast cancer or a triple negative breast cancer.

17. The method of claim 14, wherein the c-Abl inhibitor is imatinib.

18. The method of claim 17, wherein administering an effective amount of the c-Abl inhibitor comprises orally administering the c-Abl inhibitor.

19. A method for diagnosing a cancer treatable with a c-Abl inhibitor in a subject, comprising:
   (a) providing a biological sample including one or more cells from the subject;
   (b) determining an amount in the one or more cells in the sample of geminin and nuclear c-Abl;

(c) comparing the amount of both geminin and nuclear c-Abl in the one or more cells in the sample, if present, to a control level of geminin and nuclear c-Abl; and
(d) administering an effective amount of a c-Abl inhibitor to the subject if there is a measurable increase in the amount of geminin and nuclear c-Abl in the one or more cells in the sample as compared to the control level.

20. The method of claim 19, wherein the c-Abl inhibitor is selected from the group consisting of imatinib and nilotinib.

\* \* \* \* \*